United States Patent
Biedermann et al.

(10) Patent No.: US 7,192,967 B1
(45) Date of Patent: Mar. 20, 2007

(54) CYCLIC IMIDE-SUBSTITUTED PYRIDYLALKANE, ALKENE, ALKINE CARBOXAMIDES USEFUL AS CYTOSTATIC AND IMMUNOSUPPRESSIVE AGENTS

(75) Inventors: Elfi Biedermann, Vaterstetten (DE); Max Hasmann, Neuried (DE); Roland Löser, Feldafing (DE); Benno Rattel, Munich (DE); Friedemann Reiter, Putzbrunn (DE); Barbara Schein, Neufahrn (DE); Klaus Seibel, Gräfelfing (DE); Klaus Vogt, Munich (DE); Katia Wosikowski, Poing (DE); Isabel Schemainda, Munich (DE)

(73) Assignee: Astellas Pharma GmbH, Munich (DE)

( * ) Notice: Subject to any disclaimer, the term of this patent is extended or adjusted under 35 U.S.C. 154(b) by 1168 days.

(21) Appl. No.: 09/595,218

(22) Filed: Jun. 16, 2000

Related U.S. Application Data

(63) Continuation of application No. PCT/EP98/08267, filed on Dec. 16, 1998.

(30) Foreign Application Priority Data

Dec. 17, 1997 (DE) ................ 197 56 212

(51) Int. Cl.
C07D 401/01 (2006.01)
C07D 211/02 (2006.01)
A61K 31/44 (2006.01)

(52) U.S. Cl. .......... 514/290; 514/318; 514/336; 514/338; 514/339; 514/340; 514/341; 514/342; 514/343; 546/79; 546/193; 546/268.1; 546/269.7; 546/277.4; 546/278.7

(58) Field of Classification Search ........ 514/318, 514/336, 338, 339, 340, 341, 342, 343, 290; 546/193, 268.1, 269.7, 277.4, 278.7, 79
See application file for complete search history.

(56) References Cited

U.S. PATENT DOCUMENTS

| 4,283,541 A | 8/1981 | Shroff et al. ........... 546/336 |
| 5,169,856 A | 12/1992 | Goto et al. ........... 514/331 |
| 5,260,323 A | 11/1993 | Baader et al. .......... 514/356 |
| 5,326,772 A | 7/1994 | Klemm et al. ......... 514/318 |

FOREIGN PATENT DOCUMENTS

| CA | 2085954 | 6/1993 |
| DE | 4020570 | 1/1992 |
| EP | 048045 | 3/1982 |
| EP | 210782 | 2/1987 |
| EP | 271023 | 6/1988 |
| EP | 330026 | 8/1989 |
| EP | 343307 | 11/1989 |
| EP | 416581 | 3/1991 |
| EP | 471236 | 2/1992 |
| EP | 479601 | 4/1992 |
| EP | 522606 | 1/1993 |
| EP | 530444 | 3/1993 |
| EP | 548883 | 6/1993 |
| EP | 512902 | 4/1994 |
| EP | 428434 | 5/1994 |
| GB | 2304714 | 11/1998 |
| JP | 57136518 | 8/1982 |
| JP | 63179869 | 7/1988 |
| WO | WO89/07443 | 8/1989 |
| WO | WO91/15484 | 10/1991 |
| WO | WO91/15485 | 10/1991 |
| WO | WO93/14113 | 7/1993 |
| WO | WO95/10514 | 4/1995 |
| WO | WO95/10515 | 4/1995 |
| WO | WO95/10516 | 4/1995 |
| WO | WO95/24894 | 9/1995 |
| WO | WO93/14070 | 9/1996 |
| WO | WO96/31478 | 10/1996 |
| WO | WO94/01402 | 3/1997 |

(Continued)

OTHER PUBLICATIONS

Allgemeine Pathologie und Pathologische Anatomie.

(Continued)

Primary Examiner—Zinna N. Davis
(74) Attorney, Agent, or Firm—Scully, Scott, Murphy & Presser, PC

(57) ABSTRACT

The invention relates to new pyridylalkane, alkene, and alkine carboxamides substituted with an imide with a saturated or one or several-fold unsaturated hydrocarbon residue in the carboxylic acid group according to general formula (I), wherein the residue E is a cyclic imide, methods for the production of these compounds, medicaments containing these and their production as well as their therapeutic use, especially as cytostatic agents and immunosuppressive agents, for example in the treatment or prevention of various types of tumors, inhibition of abnormal cell growth and control of immune reactions, for example autoimmune diseases.

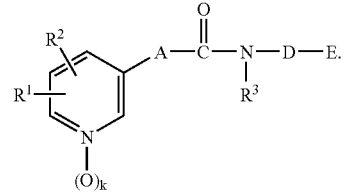

(I)

24 Claims, No Drawings

FOREIGN PATENT DOCUMENTS

| WO | WO93/13083 | 4/1997 |
| WO | WO97/48397 | 12/1997 |
| WO | WO96/31477 | 1/1998 |
| WO | WO97/48695 | 1/1998 |

OTHER PUBLICATIONS

Chemical Abstracts, vol. 124, No. 13, 1996.
Chemical Abstracts, vol. 115, 1994.
Chemcial Abstracts, vol. 114, 1991.
Nishikawa et al., "Acrylamide Derivatives as Antiallergic Agents. 2. Synthesis and Structure-Activity Relationships of N-[4-[4-(Diphenylmethyl)-1-piperazinyl]butyl]-3-(3-pyridyl)acrylamides" Chem. Pharm. Bull. 37(1) 100-105 (1989).
Nishikawa et al., "Acrylamide Derivatives as Antiallergic Agents. 2. Synthesis and Structure-Activity Relationships of N-[4-[4-(Diphenylmethyl)-1-piperazinyl]butyl]-3-(3-pyridyl)acrylamides" J. Med. Chem. 1989, 32, 583-593.
Ishihara et al., "Central Cholinergic Agents. II. Synthesis and Acetylcholinesterase Inhibitory Activities of N-[w- [N-Alkyl-N-(phenylmethyl) amino]alkyl]-3-arylpropenamides" Chem. Pharm. Bull. 39(12) 3236-3234 (1991).
Ross, "The Preparation of Some 4-Substituted Nicotinic Acids and Nicotinamides" J. Chem. Soc. (C), 1966, 1816-1820.
Rote Liste, 1997.

CYCLIC IMIDE-SUBSTITUTED PYRIDYLALKANE, ALKENE, ALKINE CARBOXAMIDES USEFUL AS CYTOSTATIC AND IMMUNOSUPPRESSIVE AGENTS

This application is a continuation application of International Application No. PCT/EP98/08267, filed on Dec. 16, 1998, which claims priority to German Application No. 19756212.4, filed Dec. 17, 1997.

The invention relates to new pyridylalkane, alkene and alkine carboxamides substituted with a cyclic imide and with a saturated or one or several-fold unsaturated hydrocarbon residue in the carboxylic acid group, methods for the synthesis of these compounds, medicaments containing these and their production as well as their therapeutic use especially as cytostatic agents and immunosuppresive agents, for example, in the treatment or prevention of various types of tumors inhibition of abnormal cell growth and control of immune reactions, for example of autoimmune diseases.

A pressing need exists for new pharmaceuticals and/or medicaments for cytostatic therapy which not only possess a strong activity, but also exert diminished side effects in comparison to many classical cancerostatic agents, whereby treatment of a broad as possible spectrum of tumors should be made accessible. Furthermore, effective cytostatic agents for an efficient therapy should be made available. Active ingredients of this type should also be exceptionally suitable in the mentioned indications for a combination therapy, be it in connection with other cytostatic agents or with radiation (for example X-rays, radioactive elements, such as cobalt, or linear accelerator, etc.), with operative procedures, heat treatment, etc.

Additionally, from another point of view, there exists a strong need in the field of tumor therapy for new compounds, for example for overcoming or avoiding resistances, which enrich the pallet of cancerostatics based on new modes of action in the ideal case.

This object was successfully solved by the creation of the pyridylalkane, -alkene and -alkine carboxamide derivatives substituted with a cyclic imide as defined in detail in the claims and medicaments containing these as well as the use of these compounds optionally in combination with other suitable active ingredients and adjuvants, especially for cytostatic and immunosuppressive therapy or prevention.

It is known from the art that various pyridine compounds substituted in a specific manner have pharmacologically useful properties; however, in contrast to the actions of the compounds according to the invention, these lie in completely different fields of indication.

Thus, ω-pyridyl alkane and/or alkene amides with antiallergic activity are described in EP 0 210 782 which are referred to as having a 5-lipoxygenase-inhibiting and antihistamine action, wherein the amide components of these compounds contain a piperizine or homopiperizine ring and the pyridine ring can be linked together in the 2-, 3- or 4-position.

JP 63,179,869 describes further pyridyl amides, ω-pyridyl alkane and alkene amides as anti-allergic effective substances containing a substituted piperidine ring in the amine component. Similarly structured compounds with the same properties are mentioned in Chem. Pharm. Bull 37, 100–105 (1989) as well as in J. Med. Chem. 1989, 583–593.

The synthesis and pharmacological evaluation of heterocyclic carboxamides which can be substituted at an end of the molecule by completely different heterocycles such as thiophene, guinoline, indole, benzimidazole or indazole as well as pyridine are described in J. Med. Chem., 1996, pages 4692–4706. However, these compounds possess an activity directed against psychoses.

Pyridyl ureas, pyridyl thioureas and pyridyl carbonamides, wherein the amide portion is bound over an aryl-substituted alkyl chain with a piperidine ring or piperidine ring or piperazine ring, are described for example in EP-A-0 428 434 or in EP-A-0 512 902 as antagonists of the neurokinin receptor and substance P. Furthermore, pyridyl (alkyl)carbonamides, pyridyl(alkyl)sulfonamides and analogous ureas, wherein the pyridine ring is bound directly or over a methylene bridge with the amide group are disclosed in EP-A-0 479 601 as active ingredients with anti-arrhythmic properties.

Further structurally closely related compounds are represented by the piperidine compounds described in EP-A-0 330 026. These known compounds are distinguished by an anti-cholinesterase activity, an anti-amnesia activity as well as activities directed against hyperkinesia, senile dementia, mania and Alzheimer's disease.

In WO 91/15 485, the production of pyridine-3,5-dicarboxylic acid esters and amides as well as their use for the treatment of tumor conditions is described. These compounds differ from the compounds according to the invention described below with the pharmaphoric cyclic imide group in very important structural features, for example by their dicarboxyl grouping on the pyridine ring or the absence of the hydrocarbon chain between the pyridine ring and the amide grouping. The compounds disclosed in WO 89/07 443 in the form of optically pure R(−)-niguldipin and further analogous dihydropyridines with cytotoxic activity have larger structural differences. However, as compared to these known compounds, the compounds according to the invention unexpectedly possess a better activity and a wider spectrum of action despite the large structural differences.

In the international PCT patent applications WO 95/10516, WO 96/31477, WO 96/31478 or for example in WO 95/10515, tricyclic amide compounds are described which possess an anti-proliferative activity. All of these compounds described therein are distinguished in that they must imperatively possess a tricyclic anellated ring system with at least one nitrogen atom, for example 6, 11-dihydro-5H-benzo[5,6]cyclohepta[1,2-b]pyridinyl ring system as a pharmaphoric group, whereby the molecule portion opposite this tricyclic anellated system is uncommonly variable and represents one of numerous variation possibilities among numerous substitution possibilities of the given pyridyl substitution. A further meaningful difference in the substitution of these molecules in comparison to the compounds according to the invention is to be seen in the lack of the present structural element D as well as the absence of the cyclic imide group which must be present.

A further essential difference of the compounds according to the invention in comparison to these tricyclic compounds is to be recognized in the presence of the terminal 3-pyridyl-substitution which must be present. The presence of this particular type of imide required according to the invention as well as the particular bond in the 3-position of the pyridine ring according to the substitution of the invention in comparison to the above mentioned anti-proliferative compounds of the state of the art indicates that this 3-pyridyl substitution as well as the cyclic imide group can be a factor for the anti-tumor action.

In fact, the compounds according to the invention cover a different tumor spectrum from those named in the PCT/WO publications with this necessarily present tricyclic anellated ring system. In the mentioned PCT/WO publications of the state of the art, a treatment possibility in tumors is merely mentioned which is made in connection with a potential inhibition of the farnesyl protein transferase, whereby this mechanism relates to the expression of the activated ras-oncogene. In contrast to this, the compounds according to the invention with the 3-pyridyl-substitution required according to the invention are not limited to the therapy of tumor cells of this type with abnormal production of the ras-oncogene; rather, the therapy possibilities with the new compounds according to the invention extend to the combat of numerous other types of tumors with different causal mechanisms as well as immunosuppressive treatment possibilities such as autoimmune diseases.

In view of this art, the finding that the compounds according to the general formula (I) with the particular substitutions defined below have superior pharmacological activities which make them particularly suitable in an excellent manner for the therapy of tumor illnesses over a broad anti-proliferative spectrum, was completely unexpected. The pharmacological finding that, aside from the cytostatic effectiveness, especially with different tumor spectra, the compounds according to the invention also possess immunosuppressive properties and additionally favorable abortive properties without harmful mutagenic effects is to be considered as equally surprising.

As a result of this particular molecular structure now found, a further class of compounds with, among others, pronounced cancerostatic activity with a novel mode of action is offered.

The new pyridyl carboxamides substituted with cyclic imide correspond to the following general formula:

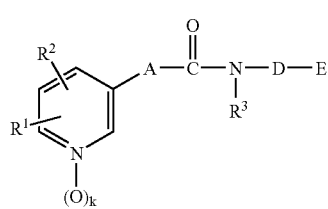

(I)

wherein

E represents a cyclic imide of the general formula

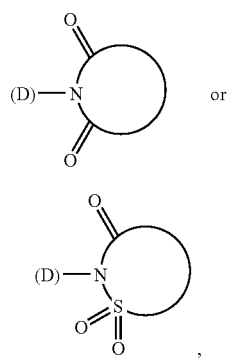

(E1)

or (E2)

bound over the imide nitrogen atom to D selected from
saturated or unsaturated monocyclic imides with 5 to 7 ring atoms whereby in this imide ring, aside from the essential imide nitrogen atom, one or two further hetero-atoms can be present selected from N and/or S and/or O;

saturated unsaturated or aromatic anellated bi-, tri- or tetracyclic imides with 8 to 18 ring atoms of which, aside from the essential imide nitrogen atom, one to three further hetero-atoms can be present selected from N and/or S and/or O;

saturated or unsaturated, bridged bi-, tri-, tetra- or pentacyclic imides with 8 to 22 ring atoms, among which, aside from the essential imide nitrogen atom, one to three further hetero-atoms can be present selected from N and/or S and/or O;

saturated or unsaturated spirocyclic imides, optionally anellated once or twice, and with a total of 9 to 23 ring atoms among which, aside from the essential imide nitrogen atom, one to three further hetero-atoms can be present selected from N and/or S and/or O;

whereby these cyclic imides can be substituted independently of each other by one to five of the same or different groups as described in detail below:

Subject matter of the invention are further pharmacologically acceptable acid addition salts of the compounds of Formula (I) with inorganic or organic acids. Preferable examples for addition salts with suitable inorganic acids are hydrochlorides, hydrobromides, hydroiodides, sulfates and phosphates. Addition salts of organic acids are preferably acetates, benzoates, citrates, fumarates, gluconates, malates, maleates, methanesulfonates, lactates, oxalates, succinates, tartrates and tosylates.

Compounds of Formula (I) as well as their acid addition salts can also be optionally present as hydrates or other solvates. The invention includes such hydrates and solvates.

In the compounds of Formula (I) which are defined below and in detail in the claims, the definitions for their atoms or atomic groups preferably have the following meanings:

Halogen means fluorine, chlorine, bromine or iodine;

Alkyl can be straight chained or branched and preferably signifies a $C_1$–$C_6$-alkyl residue, especially a methyl-, ethyl-, propyl-, isopropyl-, butyl-, isobutyl-, sec-butyl-, tert-butyl-, cyclopropylmethyl-, pentyl-, isopentyl-, tert-pentyl-, neo-pentyl-, cyclopropylethyl-, cyclobutylmethyl- or hexyl group.

Alkylene signifies for example methylene, ethylene, propylene, tetramethylene, pentamethylene, hexamethylene, heptamethylene, octamethylene, nonamethylene or decamethylene.

Alkenyl preferably signifies $C_3$–$C_6$-alkenyl and can be straight chained or branched and preferably signifies an allyl-, 2-butenyl-, 3-butenyl-, 2-methyl-2-propenyl-, 2-pentenyl-, 4-pentenyl-, 2-methyl-2-butenyl-, 3-methyl-2-butenyl-, 2-hexenyl-, 5-hexenyl-, 4-methyl-3-pentenyl- or 2,2-dimethyl-3-butenyl-group.

Alkenylene signifies for example ethenylene, propenylene, butenylene, pentenylene, hexenylene, hexadienylene, heptenylene, octenylene, nonenylene or decenylene.

Alkinyl preferably signifies $C_2$–$C_6$-alkinyl which can be straight chained or branched and can preferably signify an ethinyl-, propargyl-, 2-butinyl-, 3-butinyl-, 4-pentinyl-, 5-hexinyl- or 4-methyl-2-pentinyl group.

Alkinylene signifies for example propinylene, butinylene, pentinylene, hexinylene, hexeninylene, heptinylene, octinylene, noninylene or decinylene.

Cycloalkyl is preferably a $C_3$–$C_8$-cycloalkyl residue, especially a cyclopropyl-, cyclobutyl-, cyclopentyl-, cyclohexyl-, cycloheptyl- or cyclooctyl group.

Hydroxyalkyl contains a hydroxyl group in one of the above mentioned alkyl residues, especially in a $C_1$–$C_6$-alkyl residue, whereby among the $C_1$–$C_6$-hydroxyalkyl residues, the hydroxymethyl- and the hydroxyethyl residue are preferred.

Aside from the oxygen atom, alkoxy residues, preferably $C_1$–$C_6$-alkoxy or $C_3$–$C_8$-cycloalkyloxyl contain one of the above mentioned preferred $C_1$–$C_6$-alkyl-, or $C_3$–$C_8$-cycloalkyl residues. Particularly preferred groups for this are the methoxy-, ethoxy-, isopropoxy-, tert-butoxy-, cyclopentyloxy- and cyclohexyloxy groups.

Alkoxy, especially $C_1$–$C_6$-alkoxy, entirely or partially replaced by fluorine is for example difluoromethoxy, trifluoromethoxy or 2,2,2-trifluoroethoxy.

Aralkyl such as phenylalkyl, especially phenyl-$C_1$–$C_3$-alkyl and/or diarylalkyl such as diphenyl-$C_1$–$C_3$-alkyl contain one and/or two phenyl groups on a methyl-, ethyl-, propyl- or isopropyl group at any position.

Alkylidene residues, especially $C_1$–$C_6$-alkylidene, $C_3$–$C_8$-cycloalkylidene, phenyl-$C_1$–$C_3$-alkylidene and diphenyl-$C_1$–$C_3$-alkylidene correspond to the above named preferred $C_1$–$C_6$-alkyl-, $C_3$–$C_8$-cycloalkyl-, phenyl-$C_1$–$C_3$-alkyl- and diphenyl-$C_1$–$C_3$-alkyl groups, but are respectively bound over a double bond.

Aside from the sulphur atom, alkylthio residues contain one of the above mentioned preferred $C_1$–$C_6$-alkyl groups. Particularly preferred groups are the methylthio-, ethylthio-, isopropylthio- and tert-butylthio groups.

Cyclopentyloxy- and cyclopentylthio- and/or cyclohexyloxy- and cyclohexylthio residues represent preferred $C_3$–$C_8$-cyclo-alkyloxy and $C_3$–$C_8$-cycloalkylthio.

Aside from the oxygen atom, alkanoyloxy residues preferably contain an aliphatic acyl group with 1 to 7 carbon atoms. Among preferred alkanoyloxy groups are the acetoxy-, propionyloxy- and pivaloyloxy groups.

Alkoxycarbonyl groups, preferably $C_2$–$C_7$-alkoxycarbonyl groups contain, aside from the carbonyl group, one of the above mentioned alkoxy groups, especially $C_1$–$C_6$-alkoxy groups. Preferred alkoxycarbonyl groups are the methoxycarbonyl-, ethoxycarbonyl-, isopropoxycarbonyl-, isobutoxycarbonyl- and tert-butoxycarbonyl groups.

Aside from the carbonyl group, alkylaminocarbonyl, especially $C_2$–$C_7$-alkylaminocarbonyl and dialkylaminocarbonyl groups, preferably $C_3$–$C_{13}$-dialkylaminocarbonyl groups, contain an alkylamino- and/or dialkylamino residue whose alkyl groups correspond especially to the $C_1$–$C_6$-alkyl groups of the above description. Preferred groups are the dimethylaminocarbonyl-, diethylaminocarbonyl- and diisopropylaminocarbonyl groups.

$C_2$–$C_7$-carboxyalkyl and $C_3$–$C_7$-carboxyalkenyl contain a carbonyl group on one of the above named $C_1$–$C_6$-alkylene and/or $C_2$–$C_6$-alkenylene residues. Preferred are the carboxymethyl-, carboxyethyl-, carboxyethenyl-, carboxybutyl- and carboxybutadienyl groups.

$C_1$–$C_6$-aminoalkyl contains an amino group in one of the above named $C_1$–$C_6$-alkyl residues. Preferred are the aminomethyl- and the aminoethyl residues.

Aside from the unsubstituted amino group, amino groups of the Formula $NR^4R^5$ are one of the below mentioned alkylamino groups, especially $C_1$–$C_6$-alkylamino groups and/or dialkyl-amino groups, especially di-($C_1$–$C_6$-alkyl) amino groups.

Alkylamino especially contains one of the above mentioned $C_1$–$C_6$-alkyl groups. Preferred groups are the methylamino-, ethylamino-, propylamino-, isopropylamino-, butylamino-, and the tert-butylamino groups.

Phenyl-$C_1$–$C_3$-alkylamino contains a phenyl group on a methylamino-, ethylamino-, propylamino- or isopropylamino residue on any carbon atom.

The preferred di-($C_1$–$C_6$-alkyl)amino residue carries two of the same or different of the above mentioned $C_1$–$C_6$-alkyl groups on the nitrogen atom. Preferred groups are the dimethylamino-, diethylamino-, dipropylamino-, diisopropylamino-, isopropyl-, methylamino-, dibutylamino- or tert-butylmethylamino groups.

Acyl, especially $C_1$–$C_6$-acyl, signifies the residue of an aliphatic saturated or unsaturated, straight chained, branched or cyclic carboxylic acid. Preferred acyl residues are formyl-, acetyl-, propionyl-, acryloyl-, butyryl-, isobutyryl-, methacryloyl-, cyclopropylcarbonyl-, pentanoyl-, pivaloyl-, cyclobutylcarbonyl-, hexanoyl- and dimethylacryloyl groups.

Alkanesulfonyl, especially $C_1$–$C_6$-alkanesulfonyl is preferably the methanesulfonyl-, ethanesulfonyl-, propanesulfonyl-, butanesulfonyl-, pentanesulfonyl- or hexanesulfonyl groups.

Saturated or unsaturated monocyclic imides with 5 to 7 ring atoms among which, aside from the essential imide nitrogen atom, one or two further hetero-atoms can be present are for example pyrrol-2,5-dione, pyrrolidin-2,5-dione, imidazolidin-2,4-dione, oxazolidin-2,4-dione, thiazolidin-2,4-dione, imidazolidin-2,4,5-trione, 1,2,4-oxadiazolidin-3,5-dione, piperidin-2,6-dione, 3H-pyridin-2,6-dione, piperazin-2,6-dione, morpholin-3,5-dione, thiomorpholin-3,5-dione, azepin-2,7-dione, 3,6-dihydroazepin-2,7-dione, hexahydroazepin-2,7-dione, hexahydro-1,3-diazepin-2,4-dione, 1,2-dihydro-1,4-diazepin-2,7-dione, hexahydro-1,4-diazepin-2,7-dione, 3,7-dihydro-1,2,5-triazepin-4,6-dione or hexahydro-1,2,5-triazepin-4,6-dione.

Saturated or unsaturated or aromatic anellated, bi-, tri- or tetracyclic imides with 8 to 18 ring atoms among which, aside from the essential imide nitrogen, one to three further hetero-atoms can be present, are for example dihydrocyclopentapyrrol-1,3-dione, tetrahydrocyclopentapyrrol-1,3-dione, pyrrolo[3,4-c]pyrrol-1,3-dione, dihydropyrrolo[3,4-c]pyrrol-1,3-dione, tetrahydropyrrolo[3,4-c]pyrrol-1,3-dione, pyrrolo[3,4-b]pyrrol-4,6-dione, dihydropyrrolo[3,4-b]pyrrol-4,6-dione, tetrahydropyrrolo[3,4-b]pyrrol-4,6-dione, pyrrolo[1,2-c]imidazol-1,3-dione, tetrahydropyrrolo[1,2-c]imidazol-1,3-dione, thieno-[2,3-c]pyrrol-4,6-dione, thieno[3,4-c]pyrrol-4,6-dione, tetrahydrothieno[3,4-c]pyrrol-4,6-dione, furo[3,4-c]pyrrol-4,6-dione, tetrahydrofuro[3,4-c]pyrrol-4,6-dione, pyrrolo[3,4-d]thiazol-4,6-dione, isoindol-1,3-dione, tetrahydroisoindol-1,3-dione, hexahydroisoindol-1,3-dione, pyrrolo[3,4-b]pyridin-5,7-dione, pyrrolo[3,4-c]pyridin-1,3-dione, pyrrolo[3,4-c]pyridazin-5,7-dione, 1,1-dioxo-benzo[d]isothiazol-3-one, dihydropurin-2,6-dione, 4H-isoquinolin-1,3-dione, 8H-[1,6]naphthyridin-5,7-dione, 5H-[1,7]naphthyridin-6,8-dione, 4H-[2,6]naphthyridin-1,3-dione, 4H-[2,7]naphthyridin-1,3-dione, 1H-quinazolin-2,4-dione, 1H-pyrido-[2,3-d]pyrimidin-2,4-dione, 1H-pyrido[3,2-d]pyrimidin-2,4-dione, 1H-pyrido[3,4-d]pyrimidin-2,4-dione, benzo[4,5]thieno(2,3-c]-pyrrol-1,3-dione, furoisoindol-1,3-dione, thienoisoindol-1,3-dione, benzoisoindol-1,3-dione, dihydrobenzoisoindol-1,3-dione, tetrahydrobenzoisoindol-1,3-dione, pyrrolo[3,4-g]quinolin-6,8-dione, dihydroimidazo[1,5-b]isoquinolin-1,3-dione, dihydropyrrolo[3,4-g]quinazolin-6,8-dione, tetrahydropyrrolo[3,4-g]quinazolin-6,8-dione, 1,2,4-triazolo[1,2-a]cinnolin-7,9-dione, dihydrocarbolin-1,3-dione, 4H-benzo[4,5]thieno[2,3-c]pyridin-1,3-dione, 1H-benzo[f]isoquinolin-2,4-dione, 4H-benzo[h]isoquinolin-1,3-dione, benzo[de]isoquinolin-1,3-dione, dibenzo[c,e]

azepin-5,7-dione, 4H-naphtho[1,8-c,d]azepin-1,3-dione, dihydro-4H-ace-naphtho[1,8-a,c]pyrrol-1,3,10-trione, 6H-pyrrolo[3,4-c]carbazol-1,3-dione, dibenzoisoindol-1,3-dione, dihydrodibenzoisoindol-1,3-dione, naphthoisoindol-1,3-dione, dihydronaphthoisoindol-1,3-dione, tetrahydronaphthoisoindol-1,3-dione, dibenzo[de,h]isoquinolin-1,3-dione, 6H-2-azapyren-1,3-dione, dihydro-12H-2-azapleia-den-1,3-dione, 1H-anthraceno[1,9-c,d]azepin-2,4-dione or 4H-anthraceno[9,1-c,d]azepin-1,3-dione.

Saturated or unsaturated, bridged bi-, tri-, tetra- or pentacyclic imides with 8 to 22 ring atoms among which, aside from the essential imide nitrogen atom, one to three further hetero-atoms can be present, are for example 3-aza-bicyclo[3.1.1]heptan-2,4-dione, 3-aza-bicyclo[3.2.1)octan-2,4-dione, 3-aza-bicyclo[3.2.1]oct-6-en-2,4-dione, 3-aza-bicyclo-[3.2.2]nonan-2,4-dione, 3-aza-bicyclo[3.2.2]non-6-en-2,4-dione, 4-aza-tricyclo[5.1.1.0 2,6]nonan-3,5-dione, 4-aza-tricyclo-[5.2.1.0 2,6]decan-3,5-dione, 4-aza-tricyclo[5.2.1.0 2,6]dec-8-en-3,5-dione, 10-oxa-4-aza-tricyclo[5.2.1.0 2,6] dec-8-en-3,5-dione, 4-aza-tricyclo[5.2.2.0 2,6]undecan-3,5-dione, 4-aza-tricyclo[5.2.2.0 2,6]undec-8-en-3,5-dione, 4-aza-benzo[8,9]tricyclo[5.2.2.0 2,6]undecan-3,5-dione, 4-aza-dibenzo[8,9:10,11]tricyclo[5.2.2.0 2,6]undecan-3,5-dione, 4-aza-dibenzo[9,10:11,12]-tricyclo[6.2.2.0 2,7]duodecan-3,5-dione, or 5-aza-dibenzo-[10,11:12,13]tricyclo [7.2.2.0 2,8]tridecan-3,5-dione.

Saturated or unsaturated spirocyclic imides, optionally anellated once or twice, and with a total of 9 to 23 ring atoms among which, aside from the essential imide nitrogen atom, one to three further hetero-atoms can be present are for example 2-azaspiro[4.4]nonan-1,3-dione, 2,7-diazaspiro[4.4]nonan-1,3-dione, 1,3-diazaspiro[4.4]nonan-2,4-dione, 1-thia-3-azaspiro[4.4]nonan-2,4-dione, 1-oxa-3-azaspiro[4.4]nonan-2,4-dione, 1,3,7-triazaspiro[4.4]nonan-2,4-dione, 1-oxa-3,7-diazaspiro-[4.4]nonan-2,4-dione, 2-azaspiro[4.5]decan-1,3-dione, 2,8-di-azaspiro(4.5)decan-1,3-dione, 1,3,7-triazaspiro[4.5]decan-2,4-dione, 1,3,8-triazaspiro[4.5]decan-2,4-dione, 1-oxa-3,8-diaza-spiro[4.5]decan-2,4-dione, 8-azaspiro[4.5]decan-7,9-dione, 7-azaspiro[4.5]decan-6,8-dione, 3-azaspiro[5.5]undecan-2,4-dione, 2-azaspiro[5.5]undecan-1,3-dione, as well as spiro[dioxoimidazolidin-indanes], spiro[oxoindolin-dioxoimidazolidines], spiro[dioxoimid-azolidin-tetrahydronaphthalines], spiro[dioxoimidazolidinpiperidines], and spiro[2,6-dioxopiperidin-tetrahydronaphthalines].

Saturated or unsaturated four- to seven-membered heterocycles with one or two hetero-atoms are for example azetidine, tetrahydrofuran, tetrahydrothiophene, pyrrolidine, tetrahydropyran, tetrahydropyridine, piperidine, tetrahydroazepine, hexahydroazepine, pyrazolidine, piperazine, morpholine, thiomorpholine, thiomorpholin-1,1-dioxide, hexahydrodiazepine or hexahydrooxazepine.

Monocyclic aromatic five- or six-membered heterocycles with one to three hetero-atoms are for example furyl, thienyl, pyrrolyl, oxazolyl, isoxazolyl, thiazolyl, isothiazolyl, imidazolyl, pyrazolyl, oxadiazolyl, thiadiazolyl, triazolyl, pyridinyl, pyrazinyl, pyridazinyl, pyrimidinyl or triazinyl.

Anellated bicyclic aromatic or partially hydrated carbocyclic ring systems with 8 to 12 ring atoms are preferably benzocyclobutyl, indanyl, indenyl, naphthyl, dihydronaphthyl, tetrahydronaphthyl, benzocycloheptenyl, tetrahydrobenzocycloheptenyl, benzocyclooctenyl or hexahydrobenzocyclooctenyl. Among partially hydrated carbocyclic ring systems, their mono- or dioxo-derivates also included, i.e. for example, the indanone, tetralone, benzocycloheptenone or tetrahydrobenzocycloheptenone groups.

Anellated bicyclic aromatic or partially hydrated heterocyclic ring systems with 8 to 12 ring atoms are for example imidazothiazolyl, benzofuryl, dihydrobenzofuryl, benzothienyl, dihydrobenzothienyl, indolyl, indolinyl, isoindolinyl, benzoimidazolyl, indazolyl, benzooxazolyl, benzoisoxazolyl, benzothiazolyl, benzoisothiazolyl, benzothiadiazolyl, benzotriazolyl, chromanyl, benzopyranyl, quinolinyl, isoquinolinyl, dihydroquinolinyl, tetrahydroquinolinyl, benzodioxanyl, quinoxalinyl, quinazolinyl, tetrahydrobenzooxepinyl, tetrahydrobenzothiepinyl, benzoazepinyl, and tetrahydrobenzoazepinyl.

Among partially hydrated heterocyclic ring systems, their mono- or dioxo derivates and/or optionally their possible tautomers are additionally included, i.e. for example, ring systems such as indolinone, isatin, benzooxazolone and/or its tautomer hydroxybenzooxazole, as well as benzoisoxazolone, benzothiazolone, benzoisothiazolone and benzoimidazolone and/or their tautomers hydroxybenzoisoxazole, as well as hydroxybenzothiazole, hydroxybenzoisothiazole and hydroxybenzoimidazole, indazolinone, and chromanone, chromone, quinolinone, dihydroquinolinone and tetrahydrobenzoazepinones.

Hence, the invention concretely relates to new imide-substituted pyridylalkane, pyridylalkene and pyridylalkine acid amides of the general Formula (I)

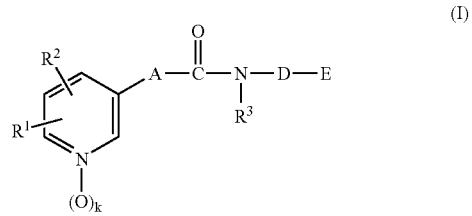

wherein the substituents have the following meanings:

$R^1$ is selected from
hydrogen, halogen, cyano, alkyl, alkenyl, alkinyl, trifluoromethyl, cycloalkyl, hydroxyalkyl, hydroxy, alkoxy, cycloalkyloxy, aralkyloxy such as benzyloxy, alkanoyloxy, alkylthio, alkoxycarbonyl, alkanoyloxy, alkylthio, alkoxycarbonyl, aminocarbonyl, alkylaminocarbonyl, dialkylaminocarbonyl, carboxy, aryl such as phenyl, aryloxy such as phenoxy, arylthio such as phenylthio, heteroaryloxy such as pyridyloxy, heteroarylthio such as pyridylthio, and $NR^4R^5$, whereby $R^4$ and $R^5$ are selected independently from each other from hydrogen, alkyl, alkenyl, alkinyl, aralkyl such as benzyl and aryl such as phenyl;

$R^2$ is selected from
hydrogen, halogen, cyano, alkyl, trifluoromethyl, hydroxy, alkoxy and aralkyloxy such as benzyloxy;

$R^3$ is selected from
hydrogen, alkyl, alkenyl, alkinyl, hydroxy, alkoxy and aryloxy such as benzyloxy;

k is 0 or 1,

A is selected from
alkylene, optionally substituted one to three-fold by alkyl, hydroxy, alkoxy, fluorine, or aryl such as phenyl,
alkylene, wherein a methylene unit is isosterically replaced by O, S, $NR^6$, CO, SO or $SO_2$, whereby, with the exception of CO, the isosteric substitution cannot be adjacent to the amine group and $R^6$ is selected from hydrogen, alkyl, alkenyl, acyl or alkanesulfonyl;

1,2-cyclopropylene;

alkenylene, optionally substituted once or twice by alkyl, hydroxy, alkoxy, fluorine, cyano or aryl such as phenyl;

alkadienylene, optionally substituted once or twice by alkyl, fluorine, cyano or aryl such as phenyl;

hexatrienylene, optionally substituted by $C_1$–$C_3$-alkyl, fluorine, cyano or phenyl; as well as ethinylene;

D is selected from alkylene, optionally substituted once or twice by alkyl, hydroxy, or alkoxy;

alkenylene, optionally substituted once or twice by alkyl, hydroxy, or alkoxy;

alkinylene, optionally substituted once or twice by alkyl, hydroxy, or alkoxy; as well as alkylene, alkenylene or alkinylene, in which one to three methylene units are isosterically replaced by O, S, $NR^7$, CO, SO or $SO_2$, whereby $R^7$ is synonymous with $R^6$, but is selected independently thereof;

E is a cyclic imide of the general formula

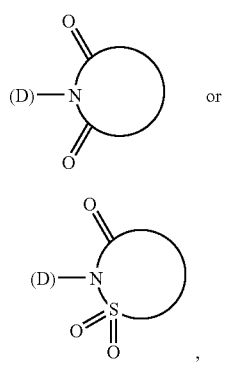

bound over the imide nitrogen atom to D selected from saturated or unsaturated monocyclic imides with 5 to 7 ring atoms, whereby, aside from the essential imide nitrogen atom, one or two further hetero-atoms can be present selected from N and/or S and/or O in this imide ring;

saturated, unsaturated or aromatic anellated bi-, tri- or tetracyclic imides with 8 to 18 ring atoms of which, aside from the essential imide nitrogen atom, one to three further hetero-atoms can be present selected from N and/or S and/or O;

saturated or unsaturated, bridged bi-, tri- tetra- or pentacyclic imides with 8 to 22 ring atoms of which, aside from the essential imide nitrogen atom, one to three further hetero-atoms can be present selected from N and/or S and/or O;

saturated or unsaturated spirocyclic imides, optionally anellated once or twice, and with a total of 9 to 23 ring atoms of which, aside from the essential imide nitrogen atom, one to three further hetero-atoms can be present selected from N and/or S and/or O;

whereby these cyclic imides can be substituted by one to five of the same or different groups selected independently from from each other from halogen, cyano, alkyl, alkylidene, trifluoromethyl, cycloalkyl, cycloalkylidene, phenylalkyl, phenylalkylidene, diphenylalkyl, diphenylalkylidene, triphenylmethyl, aryl such as phenyl, hydroxy, hydroxyalkyl, alkoxy, alkoxy entirely or partially substituted by fluorine, aralkyloxy such as benzyloxy, aryloxy such as phenoxy, naphthyloxy, mercapto, alkylthio, arylthio such as phenylthio or naphthylthio, heteroarylthio such as pyridylthio, alkanesulfonyl, arylsulfonyl such as phenylsulfonyl or naphthylsulfonyl, heteroarylsulfonyl such as pyridylsulfonyl, sulfo, carboxy, carboxyalkyl, carboxyalkenyl, alkoxycarbonyl, aralkyloxycarbonyl such as benzyloxycarbonyl, nitro, amino, aminoalkyl, mono-alkylamino, di-(alkyl)amino, arylamino such as phenylamino, arylalkylamino such as phenylalkylamino, heteroarylamino such as pyridylamino, saturated or unsaturated, four- to seven-membered heterocycles which can contain one or two hetero-atoms selected from N and/or S and/or O and are either bound directly or bound over a methylene group or a methine group, monocyclic aromatic five- or six-membered heterocycles which can contain one to three hetero-atoms selected from N and/or S and/or O and are either bound directly or bound over a methylene group or a methine group, anellated bicyclic, aromatic or partial hydrated carbocyclic ring systems with 8 to 12 ring atoms which are either bound directly or bound over a methylene or a methine group, anellated bicyclic aromatic or partially hydrated heterocyclic ring systems with 8 to 12 ring atoms, whereby one to three ring atoms can be selected from N and/or S and/or O and are either bound directly or bound over a methylene or a methine group, and whereby aryl and heteroaryl residues as substituents of the cyclic imides can be substituted themselves by one to three of the same or different groups selected from halogen, cyano, alkyl, trifluoromethyl, cycloalkyl, aralkyl such as benzyl, aryl such as phenyl, hydroxy, hydroxyalkyl, alkoxy, alkoxy entirely or partially substituted by fluorine, aralkyloxy such as benzyloxy, aryloxy such as phenoxy, mercapto, alkylthio, arylthio such as phenylthio, carboxy, carboxyalkyl, carboxyalkenyl, alkoxycarbonyl, aralkyloxycarbonyl such as benzyloxycarbonyl, nitro, amino, aminoalkyl, mono-alkylamino, di-(alkyl)amino and, for two adjacent residues, methylenedioxy;

their cis- and trans-isomers, E- and Z-isomers of the above defined compounds, especially in the case that A is a cyclopropane ring or D contains one or more double bonds, including the enantiomers, diastereomers and other isomers of the above defined compounds, as well as their racemic and/or non-racemic mixtures, as well as the pure endo- and/or exo-isomers of the above defined compounds in the case that the imide ring system is bicyclic, as well as their mixtures;

their tautomeric compounds in the optimal case that E contains a heterocyclic aromatic ring with simultaneous substitution by free hydroxy, mercapto or amino groups as well as the acid addition salts of the above defined compounds including their hydrates and solvates.

According to a preferred embodiment, the imide-substituted pyridylalkane, pyridylalkene and pyridylalkine acid amides of formula (I)

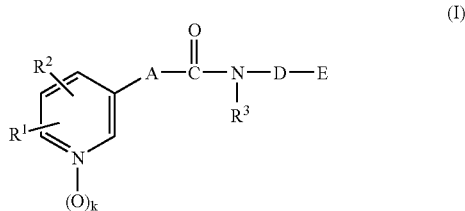

(I)

have the following substituent meanings:

$R^1$ is selected from
hydrogen, halogen, cyano, $C_1$–$C_6$-alkyl, $C_3$–$C_6$-alkenyl, $C_2$–$C_6$-alkinyl, trifluoromethyl, $C_3$–$C_8$-cycloalkyl, $C_1$–$C_6$-hydroxyalkyl, hydroxy, $C_1$–$C_6$-alkoxy, $C_3$–$C_8$-cycloalkyloxy, benzyloxy, $C_1$–$C_7$-alkanoyloxy, $C_1$–$C_6$-alkylthio, $C_2$–$C_7$-alkoxycarbonyl, aminocarbonyl, $C_2$–$C_7$-alkylaminocarbonyl, $C_3$–$C_{13}$-dialkylaminocarbonyl, carboxy, phenyl, phenoxy, phenylthio, pyridyloxy, pyridylthio, and $NR^4R^5$, whereby $R^4$ and $R^5$ are selected independently from each other from
hydrogen, $C_1$–$C_6$-alkyl, $C_3$–$C_6$-alkenyl, $C_3$–$C_6$-alkinyl, benzyl and phenyl;

$R^2$ is selected from
hydrogen, halogen, cyano, $C_1$–$C_6$-alkyl, trifluoromethyl, hydroxy, $C_1$–$C_6$-alkoxy and benzyloxy;

$R^3$ is selected from
hydrogen, $C_1$–$C_6$-alkyl, $C_3$–$C_6$-alkenyl, $C_3$–$C_6$-alkinyl, hydroxy, $C_1$–$C_6$-alkoxy and benzyloxy;

k is 0 or 1,

A is selected from
$C_1$–$C_6$-alkylene, optionally substituted one to three-fold by $C_1$–$C_3$-alkyl, hydroxy, $C_1$–$C_3$-alkoxy, fluorine, or phenyl;
$C_2$–$C_6$-alkylene, in which a methylene unit is isosterically replaced by O, S, $NR^6$, CO, SO or $SO_2$;
whereby, with the exception of CO, the isosteric substitution cannot be adjacent to the amide group and $R^6$ is selected from hydrogen, $C_1$–$C_6$-alkyl, $C_3$–$C_6$-alkenyl, $C_1$–$C_6$-acyl or $C_1$–$C_6$-alkanesulfonyl;
1,2-cyclopropylene;
$C_2$–$C_6$-alkenylene, optionally substituted once or twice by $C_1$–$C_3$-alkyl, hydroxy, $C_1$–$C_3$-alkoxy, fluorine, cyano or phenyl;
$C_4$–$C_6$-alkadienylene, optionally substituted once to twice by $C_1$–$C_3$-alkyl, fluorine, cyano or phenyl;
1,3,5-hexatrienylene, optionally substituted by $C_1$–$C_3$-alkyl, fluorine, cyano or phenyl; as well as
ethinylene;

D is selected from
$C_2$–$C_{10}$-alkylene, optionally substituted once or twice by $C_1$–$C_6$-alkyl, hydroxy, or $C_1$–$C_6$-alkoxy;
$C_4$–$C_{10}$-alkenylene, optionally substituted once or twice by $C_1$–$C_6$-alkyl, hydroxy, or $C_1$–$C_6$-alkoxy;
$C_4$–$C_{10}$-alkinylene, optionally substituted once or twice by $C_1$–$C_6$-alkyl, hydroxy, or $C_1$–$C_6$-alkoxy; as well as
$C_2$–$C_{10}$-alkylene, $C_4$–$C_{10}$-alkenylene or $C_4$–$C_{10}$-alkinylene, in which one to three methylene units is isosterically replaced by O, S, $NR^7$, CO, SO or $SO_2$, whereby $R^7$ is synonymous with $R^6$, but is selected independently thereof;

E is a cyclic imide of the general formula

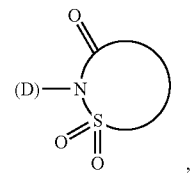

bound over the imide nitrogen atom to D selected from
saturated or unsaturated monocyclic imides with 5 to 7 ring atoms of which, aside from the essential imide nitrogen atom, one or two further hetero-atoms can be present selected from N and/or S and/or O;

saturated, unsaturated or aromatic anellated, bi-, tri- or tetracyclic imides with 8 to 18 ring atoms of which, aside from the essential imide nitrogen atom, one to three further hetero-atoms can be present selected from N and/or S and/or O;

saturated or unsaturated, bridged bi-, tri- tetra- or pentacyclic imides with 8 to 22 ring atoms of which, aside from the essential imide nitrogen atom, one to three further hetero-atoms can be present selected from N and/or S and/or O;

saturated or unsaturated spirocyclic imides, optionally anellated once or twice, and with a total of 9 to 23 ring atoms of which, aside from the essential imide nitrogen atom, one to three further hetero-atoms can be present selected from N and/or S and/or O;

whereby these cyclic imides can be substituted by one to five of the same or different groups selected independently from each other from halogen, cyano, $C_1$–$C_6$-alkyl, $C_1$–$C_6$-alkylidene, trifluoromethyl, $C_3$–$C_8$-cycloalkyl, $C_3$–$C_8$-cycloalkylidene, phenyl-$C_1$–$C_3$-alkyl, phenyl-$C_1$–$C_3$-alkylidene, diphenyl-$C_1$–$C_3$-alkyl, diphenyl-$C_1$–$C_3$-alkylidene, triphenylmethyl, phenyl, hydroxy, $C_1$–$C_6$-hydroxyalkyl, $C_1$–$C_6$-alkoxy, $C_1$–$C_6$-alkoxy entirely or partially substituted by fluorine, benzyloxy, phenoxy, naphthyloxy, mercapto, $C_1$–$C_6$-alkylthio, phenylthio, naphthylthio, pyridylthio, $C_1$–$C_6$-alkanesulfonyl, phenylsulfonyl, naphthylsulfonyl, pyridylsulfonyl, sulfo, carboxy, $C_2$–$C_7$-carboxyalkyl, $C_2$–$C_7$-carboxyalkenyl, $C_2$–$C_7$-alkoxycarbonyl, benzyloxycarbonyl, nitro, amino, $C_1$–$C_6$-aminoalkyl, mono-$C_1$–$C_6$-alkylamino, di-($C_1$–$C_6$-alkyl)amino, phenylamino, phenyl-$C_1$–$C_3$-alkylamino, pyridylamino, saturated or unsaturated, four- to seven-membered heterocycles which can contain one or two hetero-atoms selected from N and/or S and/or O and are either bound directly or bound over a methylene group or a methine group, monocyclic aromatic five- or six-membered heterocycles which can contain one to three hetero-atoms selected from N and/or S and/or O and are either bound directly or bound over a methylene group or a methine group, anellated bicyclic, aromatic or partial hydrated carbocyclic ring systems with 8 to 12 ring atoms which are either bound directly or bound over a methylene or a methine group, anellated bicyclic aromatic or partially hydrated heterocyclic ring systems with 8 to 12 ring atoms, whereby one to three ring atoms can be selected from N and/or S and/or O and are either bound directly or bound over a methylene or a methine group, and whereby aryl and heteroaryl residues as substituents of the cyclic imides can be substituted themselves by one to three of the same or different groups selected from halogen, cyano, $C_1$–$C_6$-alkyl, trifluoromethyl, $C_3$–$C_8$-cycloalkyl, benzyl, phenyl, hydroxy, $C_1$–$C_6$-hydroxyalkyl, $C_1$–$C_6$-alkoxy, $C_1$–$C_6$-alkoxy entirely or partially substituted by fluorine, benzyloxy, phenoxy, mercapto, $C_1$–$C_6$-alkylthio, phenylthio, carboxy, $C_2$–$C_7$-carboxyalkyl, $C_2$–$C_7$-carboxyalkenyl, $C_2$–$C_7$-alkoxycarbonyl, benzyloxycarbonyl, nitro, amino, $C_1$–$C_6$-aminoalkyl, mono-$C_1$–$C_6$-alkylamino, di-($C_1$–$C_6$-alkyl)amino and, for two adjacent residues, methylenedioxy;

their cis- and trans-isomers, E- and Z-isomers of the above defined compounds, especially in the case that A is a cyclopropane ring or D contains one or more double bonds, including the enantiomers, diastereomers and other isomers of the above defined compounds, as well as their racemic and/or non-racemic mixtures, as well as the pure endo- and/or exo-isomers of the above defined compounds in the case that the imide ring system is bicyclic, as well as their mixtures;

their tautomeric compounds in the optimal case that E contains a heterocyclic aromatic ring with simultaneous substitution by free hydroxy, mercapto or amino groups; and the corresponding acid addition salts of the above defined compounds including their hydrates and solvates.

According to a particularly preferred embodiment, the invention relates to compounds of the general formula (I)

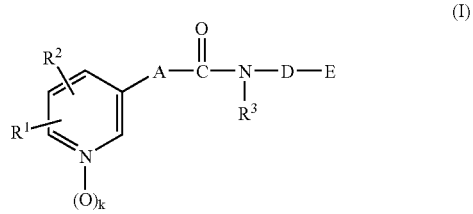

(I)

wherein the substituents have the following meanings:

$R^1$ is selected from
hydrogen, halogen, cyano, $C_1$–$C_6$-alkyl, trifluoromethyl, ethinyl, hydroxy, $C_1$–$C_4$-alkoxy, benzyloxy, $C_1$–$C_4$-alkyl-thio, $C_2$–$C_5$-alkoxycarbonyl, aminocarbonyl, $C_3$–$C_9$-dialkylaminocarbonyl, carboxy, phenoxy, phenylthio and pyridyloxy;

$R^2$ is selected from
hydrogen, fluorine, chlorine, bromine, $C_1$–$C_4$-alkyl, trifluoromethyl, hydroxy, $C_1$–$C_4$-alkoxy;

$R^3$ is selected from
hydrogen, $C_1$–$C_3$-alkyl, allyl, hydroxy, $C_1$–$C_3$-alkoxy and benzyloxy;

k is 0 or 1,

A is selected from
$C_1$–$C_6$-alkylene, optionally substituted once or twice by $C_1$–$C_3$-alkyl, hydroxy, fluorine or phenyl;
$C_2$–$C_6$-alkylene, wherein a methylene unit is isosterically replaced by O, S, NH, N(CH$_3$) or CO, whereby, with the exception of CO, the isosteric substitution cannot be adjacent to the amide group; and
1,2-cyclopropylene;
$C_2$–$C_6$-alkenylene, optionally substituted once or twice by $C_1$–$C_3$-alkyl, phenyl, hydroxy and/or fluorine;
$C_4$–$C_6$-alkadienylene, optionally substituted once to twice by methyl or fluorine;
1,3,5-hexatrienylene, optionally substituted by methyl or fluorine; as well as
ethinylene D is selected from
$C_2$–$C_8$-alkylene, optionally substituted once or twice by $C_1$–$C_3$-alkyl or hydroxy;
$C_4$–$C_8$-alkenylene, optionally substituted once or twice by $C_1$–$C_3$-alkyl or hydroxy;
$C_4$–$C_8$-alkinylene, optionally substituted once or twice by $C_1$–$C_3$-alkyl or hydroxy; as well as
$C_2$–$C_8$-alkylene, $C_4$–$C_8$-alkenylene or $C_4$–$C_8$-alkinylene, wherein one to three methylene units are isosterically replaced by O, S, NH, N(CH$_3$), N(COCH$_3$), N(SO$_2$CH$_3$), CO or SO$_2$;

E is selected from
saturated or unsaturated monocyclic imides with 5 to 7 ring atoms, for example, pyrrol-2,5-dione, pyrrolidin-2,5-dione, imidazolidin-2,4-dione, oxazolidin-2,4-dione, thiazolidin-2,4-dione, imidazolidin-2,4,5-trione, piperidin-2,6-dione, 3H-pyridin-2,6-dione, piperazin-2,6-dione, morpholin-3,5-dione, azepin-2,7-dione, 3,6-dihydroazepin-2,7-dione, hexahydroazepin-2,7-dione, hexahydro-1,3-diazepin-2,4-dione, hexahydro-1,4-diazepin-2,7-dione, 3,7-dihydro-1,2,5-triazepin-4,6-dione, hexahydro-1,2,5-triazepin-4,6-dione,
saturated, unsaturated or aromatic anellated bicyclic imides, for example, pyrrolo[3,4-c]pyrrol-1,3-dione, dihydropyrrolo[3,4-c)pyrrol-1,3-dione, tetra-hydropyrrolo[3,4-c]pyrrol-1,3-dione, tetrahydropyrrolo[1,2-c]imidazol-1,3-dione, thieno[2,3-c]pyrrol-4,6-dione, thieno[3,4-c]pyrrol-4,6-dione, furo[3,4-c]pyrrol-4,6-dione, pyrrolo[3,4-d]thiazol-4,6-dione, isoindol-1,3-dione, tetrahydroisoindol-1,3-dione, hexahydroisoindol-1,3-dione, pyrrolo[3,4-b]pyridin-5,7-dione, pyrrolo[3,4-c]pyridin-1,3-dione, pyrrolo[3,4-c]pyridazin-5,7-dione, 1,1-dioxo-benzo[d]isothiazol-3-one, dihydropurin-2,6-dione, 4H-isoquinolin-1,3-dione, 5H-[1,7]naphthyridin-6,8-dione, 4H-[2,6]naphthyridin-1,3-dione, 1H-quinazolin-2,4-dione, 1H-pyrido[2,3-d]pyrimidin-2,4-dione, 1H-pyrido[3,4-d]pyrimidin-2,4-dione,
unsaturated or aromatic anellated tricyclic imides, such as, for example, benzo[4,5]thieno[2,3-c]pyrrol-1,3-dione, thienoisoindol-1,3-dione, benzoisoindol-1,3-dione, dihydrobenzoisoindol-1,3-dione, tetrahydrobenzoisoindol-1,3-dione, pyrrolo[3,4-g]quinolin-6,8-dione, tetrahydropyrrolo[3,4-g]quinazolin-6,8-dione, 1,2,4-triazolo[1,2-a]cinnolin-7,9-dione, dihydrocarbolin-1,3-dione, 4H-benzo[h]iso-quinolin-1,3-dione, benzo[de]isoquinolin-1,3-dione, dibenzo[c,e]azepin-5,7-dione, 4H-naphtho[1,8-c,d]azepin-1,3-dione,
unsaturated or aromatic anellated tetracyclic imides, such as, for example, dihydro-4H-acenaphtho-[1,8-a,c]pyrrol-1,3,10-trione, 6H-pyrrolo[3,4-c]carbazol-1,3-dione, dibenzoisoindol-1,3-dione, naphthoisoindol-1,3-dione, tetrahydronaphthoisoindol-1,3-dione, dibenzo[de,h]-isoquinolin-1,3-dione, dihydro-12H-2-azapleiaden-1,3-dione, 1H-anthra[1,9-c,d]azepin-2,4-dione, 4H-anthra[9,1-c,d]azepin-1,3-dione, saturated or unsaturated, bridged bi-, tri-, tetra- or pentacyclic imides such as, for example, 3-aza-bicyclo[3.2.1]octan-2,4-dione, 3-aza-bicyclo[3.2.1]oct-6-en-2,4-dione, 3-aza-bicyclo(3.2.2]nonan-2,4-dione, 3-aza-bicyclo[3.2.2]non-6-en-2,4-dione, 4-aza-tricyclo[5.2.1.0 2,6]dec-8-en-3,5-dione, 10-oxa-4-aza-tricyclo[5.2.1.0 2,6]dec-8-en-3,5-dione, 4-aza-tricyclo[5.2.2.0 2,6]undecan-3,5-dione, 4-aza-tricyclo[5.2.2.0 2,6]undec-8-en-3,5-dione, 4-aza-benzo[8,9]tricyclo[5.2.2.0 2,6]undecan-3,5-dione, 4-aza-dibenzo[8,9:10,11]tricyclo[5.2.2.0 2,6]undecan-3,5-dione, 5-aza-dibenzo[10,11:12,13]tricyclo[7.2.2.0 2,8]tri-decan-3,5-dione, and saturated or unsaturated spirocyclic imides which are optionally benzoanellated once or twice such as 1,3-diazaspiro[4.4]nonan-2,4-dione, 1-thia-3-azaspiro[4.4]nonan-2,4-dione, 1-oxa-3-azaspiro[4.4]-nonan-2,4-dione, 1,3,7-tri-azaspiro[4.4]nonan-2,4-dione, 1-oxa-3,7-diazaspiro[4.4]-nonan-2,4-dione, 2,8-diazaspiro[4.5]decan-1,3-dione, 1,3,8-triazaspiro[4.5]decan-2,4-dione, 1-oxa-3,8-diazaspiro[4.5]-decan-2,4-dione, 7-azaspiro[4.5]decan-6,8-dione, spiro[dioxoimidazolidin-indanes], spiro[oxoindolin-dioxoimidazolidines], spiro[dioxoimidazolidin-tetrahydronaphthalines], spiro[dioxoimidazolidin-piperidines], and spiro[2,6-dioxopiperidin-tetrahydronaphthalines], whereby these cyclic imides can be substituted by one to five of the same or different groups selected independently from each other from halogen, cyano, C$_1$–C$_4$-alkyl, C$_1$–C$_4$-alkylidene, trifluoromethyl, C$_3$–C$_8$-cycloalkyl, phenyl-C$_1$–C$_3$-alkyl, phenyl-C$_1$–C$_3$-alkylidene, diphenyl-C$_1$–C$_3$-alkyl, diphenyl-C$_1$–C$_3$-alkylidene, triphenylmethyl, phenyl, hydroxy, C$_1$–C$_4$-hydroxyalkyl, C$_1$–C$_4$-alkoxy, C$_1$–C$_4$-Alkoxy entirely or partially substituted by fluorine, benzyloxy, phenoxy, naphthyloxy, mercapto, C$_1$–C$_4$-alkylthio, phenylthio, pyridylthio, C$_1$–C$_4$-alkanesulfonyl, phenylsulfonyl, naphthylsulfonyl, pyridylsulfonyl, sulfo, carboxy, C$_2$–C$_7$-carboxyalkyl, C$_2$–C$_7$-carboxyalkenyl, C$_2$–C$_7$-alkoxycarbonyl, benzyloxycarbonyl, nitro, amino, C$_1$–C$_4$-aminoalkyl, mono-C$_1$–C$_4$-alkylamino, di-(C$_1$–C$_4$-alkyl)amino, phenylamino, phenyl-C$_1$–C$_3$-alkylamino, pyridylamino, saturated or unsaturated, four- to seven-membered heterocycles which can contain one or two hetero-atoms selected from N and/or S and/or O, monocyclic aromatic five- or six-membered heterocycles, which can contain one to three hetero-atoms selected from N and/or S and/or O and are either bound directly or bound over a methylene group or a methine group, anellated bicyclic, aromatic or partially hydrated carbocyclic ring systems with 8 to 11 ring atoms which are either bound directly or bound over a methylene group or a methine group, anellated bicyclic aromatic or partially hydrated heterocyclic rings systems with 8 to 11 rings atoms, whereby one to three ring atoms can be selected from N and/or S and/or O and are either bound directly or bound over a methylene group or a methine group, and whereby aryl and heteroaryl residues as substituents of the cyclic imides can be substituted themselves by one to three of the same or different groups selected from halogen, cyano, C$_1$–C$_6$-alkyl, trifluoromethyl, C$_3$–C$_8$-cycloalkyl, benzyl, phenyl, hydroxy, C$_1$–C$_6$-hydroxyalkyl, C$_1$–C$_6$-alkoxy, C$_1$–C$_6$-alkoxy entirely or partially substituted by fluorine, benzyloxy, phenoxy, mercapto, C$_1$–C$_6$-alkylthio, phenylthio, carboxy, C$_2$–C$_7$-carboxyalkyl, C$_2$–C$_7$-carboxyalkenyl, C$_2$–C$_7$-alkoxycarbonyl, benzyloxycarbonyl, nitro, amino, C$_1$–C$_6$-aminoalkyl, mono-C$_1$–C$_6$-alkylamino, di-(C$_1$–C$_6$-alkyl)amino and, for two adjacent residues, methylenedioxy.

According to a further preferred embodiment the invention relates to compounds of the general formula (I)

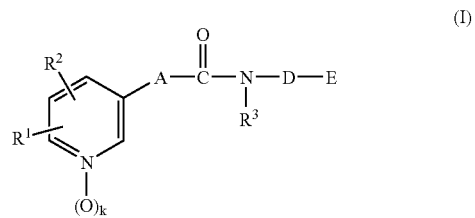

(I)

wherein the substituents have the following meanings:

R$^1$ is selected from
hydrogen, fluorine, chlorine, bromine, methyl, ethyl, trifluoromethyl, hydroxy, C$_1$–C$_4$-alkoxy, phenoxy, methylthio, ethylthio, methoxycarbonyl, aminocarbonyl and carboxy;

R$^2$ is selected from
hydrogen, chlorine, methyl, hydroxy and methoxy;

R$^3$ is hydrogen;

k is 0,

A is selected from
C$_2$–C$_6$-alkylene, optionally substituted once or twice by hydroxy or fluorine;
C$_2$–C$_6$-alkylene, in which a methylene unit is isosterically replaced by O, S, or CO, whereby, with the exception of CO, the isosteric substitution cannot be adjacent to the amide group;
C$_2$–C$_6$-alkenylene, optionally substituted by methyl and/or fluorine;
C$_4$–C$_6$-alkadienylene, optionally substituted by methyl;
ethinylene;

D is selected from
C$_2$–C$_8$-alkylene, optionally substituted by methyl or hydroxy;
C$_4$–C$_8$-alkenylene, optionally substituted by methyl or hydroxy;
C$_4$–C$_8$-alkinylene, optionally substituted by hydroxy;
C$_2$–C$_8$-alkylene, C$_4$–C$_8$-alkenylene or C$_4$–C$_8$-alkinylene, in which a methylene unit is isosterically replaced by O, NH, N(CH$_3$), or CO, or an ethylene group is isosterically replaced by a group NH—CO and/or CO—NH, or a propylene group is isosterically replaced by a group NH—CO—NH or NH—CO—O and/or O—CO—NH;

E is selected from
monocyclic imides such as succinimide, maleinimide, glutarimide, adipinimide, imidazolidindione, imidazolidintrione, thiazolidindione, oxazolidindione, piperazin-2,6-dione, morpholin-3,5-dione, 3,6-dihydroazepin-2,7-dione, hexahydro-1,3-diazepin-2,4-dione, hexahydro-1,4-diazepin-2,7-dione, hexahydro-1,2,5-triazepin-4,6-dione, anellated bicyclic imides such as phthalimide, tetra-hydrophthalimide, homophthalimide, pyrrol-3,4-dicarboximide, 2,5-dihydropyrrol-3,4-dicarboximide, thiophen-2,3-dicarboximide, thiophen-3,4-dicarboximide, pyridin-2,3-dicarboximide, pyridin-3,4-dicarboximide, pyridazin-3,4-dicarboximide, 1,1-dioxo-benzo[d]-isothiazol-3-one, isatoic acid imide, 4H-2,6-naphthyridin-1,3-dione, 1H-pyrido[2,3-d]pyrimidin-2,4-dione, anellated tricyclic imides such as naphthalin-1,2-dicarboximide, 1,2,3,4-tetrahydronaphthalin-1,2-dicarboximide, naphthalin-2,3-dicarboximide, 1,8-naphthalimide, diphenic acid imide, benzothiophen-2,3-dicarboximide, benzothiophen-4,5-dicarboximide, quinolin-6,7-dicarboximide, quinazolin-6,7-dicarboximide, anellated tetracyclic imides such as 7,8-dihydroacenaphthen-2(6H)-on-1,8a-dicarboximide, anthracen-2,3-dicarboximide, anthracen-1,9-dicarboximide, phenanthren-9,10-dicarboximide, 12a, 12b-dihydro-12H-2-azapleiaden-1,3-dione, 1H-anthraceno[1,9-c,d]azepin-2,4-dione, carbazol-5,6-dicarboximide, bridged polycyclic imides such as cyclopentan-1,3-dicarboximide, cyclohex-2-en-1,4-dicarboximide, bicyclo[2.2.1]-hept-5-en-2,3-dicarboximide, 7-oxa-bicyclo[2.2.1]-hept-5-en-2,3-dicarboximide, bicyclo[2.2.2]-oct-5-en-2,3-dicarboximide, benzobicyclo[2.2.2]-octan-2,3-dicarboximide, dibenzobicyclo[2.2.2]-octan-2,3-dicarboximide, dibenzobicyclo[2.2.2]-octan-2,3-diacetic acid imide and spirocyclic imides such as 1,3-diazaspiro[4.4]nonan-2,4-dione, 1-thia-3-azaspiro[4.4]nonan-2,4-dione, 1-oxa-3,7-diazaspiro[4.4]nonan-2,4-dione, 1-oxa-3,8-diazaspiro[4.5]decan-2,4-dione, spiro[dioxoimidazolidin-indane], spiro[dioxoimidazolidin-piperidine], spiro[dioxoimidazolidin-oxoindoline]spiro[dioxoimidazolidin-tetrahydronaphthaline], and spiro[2,6-dioxopiperidin-tetrahydronaphthaline], whereby these cyclic imides can be substituted by one to five of the same or different groups selected independently from each other from halogen, cyano, $C_1$–$C_4$-alkyl, trifluoromethyl, $C_3$–$C_8$-cycloalkyl, hydroxy, $C_1$–$C_4$-hydroxyalkyl, $C_1$–$C_4$-alkoxy, $C_1$–$C_4$-alkoxy entirely or partially substituted by fluorine, benzyloxy, phenoxy, naphthyloxy, $C_1$–$C_4$-alkylthio, phenylthio, pyridylthio, $C_1$–$C_4$-alkanesulfonyl, phenylsulfonyl, naphthylsulfonyl, pyridylsulfonyl, sulfo, carboxy, $C_2$–$C_7$-carboxyalkyl, $C_2$–$C_7$-carboxyalkenyl, $C_2$–$C_7$-alkoxycarbonyl, benzyloxycarbonyl, nitro, amino, $C_1$–$C_4$-aminoalkyl, di-($C_1$–$C_4$-alkyl)amino, phenylamino, pyridylamino;

benzyl, benzylidene, phenylethyl, phenylethylidene, phenylpropyl, diphenylmethyl, diphenylmethylene, diphenylethyl, triphenylmethyl;

phenyl, indanyl, indenyl, indenylmethyl, naphthyl, naphthyl-methyl, tetrahydronaphthyl, benzocycloheptenyl, tetrahydrobenzocycloheptenyl;

pyrrolidinyl, piperidinyl, morpholinyl, thiomorpholinyl, piperazinyl, hexahydroazepinyl, hexahydrodiazepinyl;

furyl, furylmethyl, thienyl, thienylmethyl, oxazolyl, isoxazolyl, thiazolyl, thiazolylmethyl, imidazolyl, oxadiazolyl, pyridyl, pyridylmethyl, pyrazinyl, pyrimidinyl;

benzofuryl, benzofurylmethyl, benzothienyl, benzothienylmethyl, indolyl, indolylmethyl, indolinyl, oxoindolinyl, dioxoindolinyl, benzooxazolyl, oxobenzooxazolinyl, benzothiazolyl, benzothiazolylmethyl, oxobenzothiazolinyl, benzoimidazolyl, benzoimidazolylmethyl, oxobenzoimidazolinyl, indazolyl, oxoindazolinyl, benzotriazolyl, oxazolopyridyl, oxazolopyridylmethyl, oxodihydrooxazolopyridyl, thiazolopyridyl, oxodihydrothiazolopyridyl, imidazopyridyl, oxodihydroimidazopyridyl, chromanyl, chromanonyl, oxazolopyridyl, oxazolopyridylmethyl, isoquinolinyl, oxodihydroquinolinyl, tetrahydroquinolinyl, oxotetrahydroquinolinyl, benzodioxanyl, quinazolinyl, benzoazepinyl, tetrahydrobenzoazepinyl, benzodiazepinyl, tetrahydrobenzodiazepinyl, benzooxazepinyl, benzothiazepinyl;

and whereby aryl and heteroaryl residues as substituents of the cyclic imides can be substituted themselves by one to three of the same or different groups selected from halogen, cyano, $C_1$–$C_6$-alkyl, trifluoromethyl, $C_3$–$C_8$-cycloalkyl, benzyl, phenyl, hydroxy, $C_1$–$C_6$-hydroxyalkyl, $C_1$–$C_6$-alkoxy, $C_1$–$C_6$-alkoxy entirely or partially substituted by fluorine, benzyloxy, phenoxy, mercapto, $C_1$–$C_6$-alkylthio, phenylthio, carboxy, $C_2$–$C_7$-carboxyalkyl, $C_2$–$C_7$-carboxyalkenyl, $C_2$–$C_7$-alkoxycarbonyl, benzyloxycarbonyl, nitro, amino, $C_1$–$C_6$-aminoalkyl, mono-$C_1$–$C_6$-alkylamino, di-($C_1$–$C_6$-alkyl)amino and, for two adjacent residues, methylenedioxy as well.

Likewise, those compounds of the general formula (I)

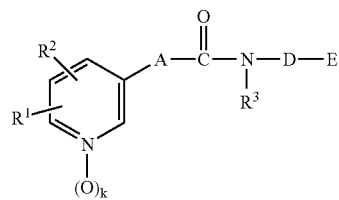

are particularly preferred wherein the substituents have the following meanings:

$R^1$ is selected from
hydrogen, fluorine, methyl, trifluoromethyl, ethylthio;

$R^2$ is hydrogen;

$R^3$ is hydrogen;

k is 0,

A is selected from
ethylene or butylene, optionally substituted by hydroxy or one or two fluorine atoms, or
$OCH_2$, $SCH_2$,
ethenylene or 1,3-butadienylene;

D is selected from
$C_4$–$C_6$-alkylene, optionally substituted by hydroxy;
$C_4$–$C_6$-alkenylene;
$C_4$–$C_6$-alkinylene; or
$C_4$–$C_6$-alkylene, $C_4$–$C_6$-alkenylene or $C_4$–$C_6$-alkinylene, wherein one or two methylene units is isosterically replaced by O, NH or CO;

E is selected from monocyclic imides such as succinimide, maleinimide, glutarimide, imidazolidindione, imidazolidintrione, thiazolidindione, oxazolidindione, piperazin-2,6-dione, hexahydrodiazepin-2,7-dione, anellated bicyclic inides such as phthalimide, homophthalimide, pyridin-2,3-dicarboximide, pyridin-3,4-dicarboximide, isatoic acid imide, anellated tricyclic imides such as naphthalin-1,2-dicarboximide, naphthalin-2,3-dicarboximide, 1,8-naphthalimide, diphenic acid imide, anellated tetracyclic imides such as 7,8-dihydroacenaphthen-2(6H)-on-1,8a-dicarboximide, anthracen-2,3-dicarboximide, anthracen-1,9-dicarboximide, phenanthren-9,10-dicarboximide, bridged polycyclic imides such as bicyclo[2.2.1]-hept-5-en-2,3-dicarboximide, 7-oxa-bicyclo[2.2.1]-hept-5-en-2,3-dicarboximide, benzobicyclo[2.2.2]-octan-2,3-dicarboximide, dibenzobicyclo[2.2.2]-octan-2,3-dicarboximide, and spirocyclic imides such as spiro[dioxoimidazolidin-indane], spiro[dioxoimidazolidin-piperidine], spiro[dioxoimidazolidin-oxoindoline] and spiro[dioxoimidazolidin-tetrahydronaphthaline], whereby these cyclic imides can be substituted by one to four of the same or different groups selected independently from each other from halogen, $C_1$–$C_4$-Alkyl, trifluoromethyl, hydroxy, hydroxymethyl, methoxy, ethoxy, tert-butoxy, trifluoromethoxy, benzyloxy, phenoxy, phenylthio, pyridylthio, phenylsulfonyl, sulfo, carboxy, $C_2$–$C_7$-carboxyalkyl, $C_2$–$C_7$-carboxyalkenyl, $C_2$–$C_7$-alkoxycarbonyl, benzyloxycarbonyl, nitro, amino, aminomethyl, dimethylamino, diethylamino, phenylamino, pyridylamino;

benzyl, benzylidene, phenylethyl, naphthylmethyl, diphenylmethyl, diphenylmethylene, triphenylmethyl, phenyl, naphthyl;

pyrrolidinyl, piperidinyl, morpholinyl, thiomorpholinyl, piperazinyl, hexahydroazepinyl, hexahydrodiazepinyl; furyl, furylmethyl, thienyl, thienylmethyl, thiazolyl, thiazolylmethyl, pyridyl, pyridylmethyl;

benzofuryl, benzothienyl, indolyl, indolylmethyl, oxodihydro-indolyl, benzoimidazolyl, benzoimidazolylmethyl, oxodihydrobenzoimidazolyl, benzooxazolyl, oxodihydrobenzooxazolyl, benzothiazolyl, oxodihydrobenzothiazolyl, quinolinyl, quinolinylmethyl, oxodihydroquinolinyl, isoquinolinyl, oxodihydroisoquinolinyl, and whereby aryl and heteroaryl residues as substituents of the cyclic imides can be substituted themselves by one to three of the same or different groups selected from halogen, cyano, $C_1$–$C_6$-Alkyl, trifluoromethyl, $C_3$–$C_8$-cycloalkyl, benzyl, phenyl, hydroxy, $C_1$–$C_6$-hydroxyalkyl, $C_1$–$C_6$-alkoxy, $C_1$–$C_6$-alkoxy entirely or partially substituted by fluorine, benzyloxy, phenoxy, mercapto, $C_1$–$C_6$-alkylthio, phenylthio, carboxy, $C_2$–$C_7$-carboxyalkyl, $C_2$–$C_7$-carboxyalkenyl, $C_2$–$C_7$-alkoxycarbonyl, benzyloxycarbonyl, nitro, amino, $C_1$–$C_6$-aminoalkyl, mono-$C_1$–$C_6$-alkylamino, di-($C_1$–$C_6$-alkyl)amino and, for two adjacent residues, methylendioxy.

The following end products represent very particular concrete preferred embodiments of the invention:

1) N-[4-(2,5-dioxo-3,4-diphenyl-2,5-dihydro-pyrrol-1-yl)-butyl]-3-pyridin-3-yl-acrylamide (substance 43)
2) N-[4-(2,6-dioxo-4-phenyl-piperidin-1-yl)-butyl]-3-pyridin-3-yl-acrylamide (substance 88)
3) N-[4-(1,3-dioxo-4,5,6,7-tetraphenyl-1,3-dihydro-isoindol-2-yl)-butyl]-3-pyridin-3-yl-acrylamide (substance 145)
4) N-[4-(3-benzyl-2,4,5-trioxo-imidazolidin-1-yl)-butyl]-3-pyridin-3-yl-acrylamide (substance 16)
5) N-[4-(1,3,10-trioxo-1,4,5,6,10,10a-hexahydro-acenaphtho[1,8a-c]pyrrol-2-yl)-butyl]-3-pyridin-3-yl-acrylamide (substance 226)
6) N-[4-(2,5-dioxo-4,4-diphenyl-imidazolidin-1-yl)-butyl-3-pyridin-3-yl-acrylamide (substance 12)
7) N-[4-(2,5-dioxo-3-phenyl-2,5-dihydro-pyrrol-1-yl)-butyl]-3-pyridin-3-yl-acrylamide (substance 28)
8) N-[3-(2,5-dioxo-3,4-diphenyl-2,5-dihydro-pyrrol-1-yl)-propyl]-3-pyridin-3-yl-acrylamide (substance 38)
9) N-[4-(3-pyridin-3-yl-acroylamino)-butyl]-2,3:5,6-dibenzobicyclo[2.2.2]octan-7,8-dicarboximide (substance 276)
10) N-[4-(5-benzyliden-2,4-dioxo-thiazolidin-3-yl)-butyl]-3-pyridin-3-yl-acrylamide (substance 23)
11) N-[4-(4-benzyl-2,6-dioxo-piperazin-1-yl)-butyl]-3-pyridin-3-yl-acrylamide (substance 92)
12) N-[6-(2,5-dioxo-3,4-diphenyl-2,5-dihydro-pyrrol-1-yl)-hexyl]-3-pyridin-3-yl-acrylamide (substance 58)
13) N-[4-(2,5-dioxo-3,4-diphenyl-2,5-dihydro-pyrrol-1-yl)-butyl]-3-pyridin-3-yl-propionamide (substance 40)
14) N-[4-(1,3-dioxo-1,3-dihydro-isoindol-2-yl)-butyl]-3-pyridin-3-yl-acrylamide (substance 119)
15) N-[4-(1,3-dioxo-1H,3H-benzo[de]isoquinolin-2-yl)-butyl]-3-(1-oxidopyridin-3-yl)-acrylamide (substance 196)
16) N-[6-(1,3-dioxo-1H,3H-benzo[de]isoquinolin-2-yl)-hexyl]-3-pyridin-3-yl-acrylamide (substance 204)
17) N-[2-(1,3-dioxo-1H,3H-benzo[de]isoquinolin-2-yl)-ethyl]-3-pyridin-3-yl-acrylamide (substance 189)
18) N-[4-(1,3-dioxo-1H,3H-benzo[de]isoquinolin-2-yl)-butyl]-3-pyridin-3-yl-acrylamide (substance 195)

Further subject-matter of the invention are known analogous methods for the production of the compounds of the above defined and exemplified formula (I) according to the invention.

Method (A):

Compounds of formula (I) can be obtained by reacting carboxylic acids of formula (II)

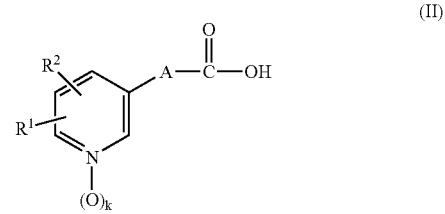

(II)

in which $R^1$, $R^2$, A and k have the meaning given above or their reactive derivatives with compounds of formula (III)

(III)

wherein D, E and $R^3$ are defined as above.

Reactive derivatives of compound (II) can be, for example, its activated esters, anhydrides, acid halides (especially acid chlorides) or simple low alkyl esters. Suitable activated esters are, for example, p-nitrophenyl ester, 2,4,6- trichlorophenyl ester, pentachlorophenyl ester, cyano-methyl ester, esters of N-hydroxysuccinimide, N-hydroxy-phthalimides, 1-hydroxybenzotriazole, N-hydroxypiperidine, 2-hydroxypyridine, 2-mercaptopyridine, etc. Anhydrides can be symmetric anhydrides or mixed, as they are obtained, for example, with pivaloyl chloride or with chloroformates. Aromatic (for example chloroformic phenyl ester), araliphatic (for example chloroformic benzyl ester) or aliphatic chloroformates (for example chloroformic methyl ester, ethyl ester or isobutyl ester) can be used for this.

Reaction of compounds (II) with compounds (III) can also be carried out in the presence of condensation agents such as dicyclohexylcarbodiimide, 1-ethyl-3-(3-dimethylaminopropyl)-carbodiimide hydrochloride, N,N'-carbonyldiimidazole, 1-ethoxycarbonyl-2-ethoxy-1,2-dihydroquinoline, etc. If carbodiimides are used as the condensation agent, reagents such as N-hydroxysuccinimide, N-hydroxyphthalimide, 1-hydroxybenzotriazole, N-hydroxypiperidine, etc. can be advantageously added.

Compounds of formula (III) can be used for reaction as free bases as well as in the form of their acid addition salts. For this, the salts of inorganic acids are to be preferred, i.e. hydrochlorides, hydrobromides or sulfates for example.

Reaction of compounds (II) or their reactive derivatives with compounds (III) is normally carried out in a suitable, preferably inert solvent. As examples, aromatic hydrocarbons such as benzene, toluene, xylene, halogenated hydrocarbons (for example dichloromethane, chloroform, 1,2-dichloroethane, trichloroethylene), ethers (for example diethyl ether, tetrahydrofuran, dioxane, glycol dimethyl ether), ethyl acetate, acetonitrile or polar aprotic solvents such as, for example, dimethylsulfoxide, dimethylformamide or N-methyl-pyrrolidone are to be named. Pure solvents, as well as mixtures of two or more, can be used.

The reaction is optionally carried out in the presence of an auxiliary base. Suitable examples for this are alkali metal carbonates (sodium carbonate, potassium carbonate), alkali metal hydrogen carbonates (sodium hydrogen carbonate, potassium hydrogen carbonate), or organic bases such as, for example, triethylamine, ethyl diisopropylamine, tributylamine, N-methylmorpholine or pyridine. A suitable excess of compound (III) can also be used as a base. If compounds (III) are used in form of their acid addition salts, then it is appropriate to consider the amount of auxiliary base used as equivalent.

The reaction temperatures can—depending on reactivity of the educts—vary in a wide range. Generally, the reaction is carried out at temperatures between −40° C. and 180° C., preferably between −10° C. and 130° C., especially at the boiling point of the solvent used.

The starting compounds (II) and (III) are known and/or can be produced according to known methods in an analogous manner. Moreover, the production of representative examples is described below.

Method (B):

Compounds of formula (I) can also be produced in that compounds of formula (IV),

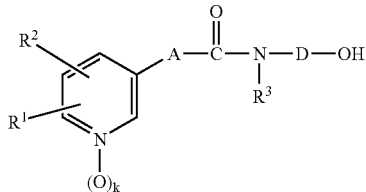

(IV)

wherein $R^1$, $R^2$, $R^3$, A, D and k have the meaning given above are reacted with imides of the general formula (V),

(V)

in which E is defined as above, under conditions of the Mitsunobu-reaction. For this, the components are combined with the formal emergence of water in a redox condensation by means of an organophosphorous$^{III}$ compound and an aliphatic azo compound. (overview: O. Mitsunobu, Synthesis 1981, P.1)

Suitable organophosphorous$^{III}$ compounds are triarylphosphines particularly such as triphenylphosphine or trialkylphosphines particularly such as tributylphosphine. However, mixed aryl-alkylphosphines can also be used such as for example methyldiphenylphosphine, or trialkyl phosphites such as trimethyl phosphite, triethyl phosphite or tributyl phosphite.

Suitable aliphatic azo compounds are, for example, azodicarboxylic esters such as azodicarboxylic dimethyl ester, but especially azodicarboxylic diethyl-ester and azodicarboxylic acid diisopropyl ester. Azodicarboxamides can be used as further aliphatic azo compounds such as, for example, N,N,N',N'-tetramethylazodicarboxadiamide, N,N,N',N'-tetraisopropylazodicarboxadiamide or 1,1'-(azodicarbonyl)-dipiperidine. Further, newer reagents are named in Org. Prep. Proced. Int. 28, 129–164 (1996).

Reaction of compounds (IV) with compounds (V) is normally carried out in a suitable, preferably aprotic solvent. As examples, aromatic hydrocarbons such as benzene, toluene, xylene, halogenated hydrocarbons (for example, dichloromethane, chloroform, 1,2-dichlorethane, trichlorethylene), ethylacetate, acetonitrile and especially ethers such as diethyl ether, diisopropyl ether, methyl-tert-butyl ether, glycoldimethyl ether, dioxane and, particularly preferred, tetrahydrofuran are to be named. Pure solvents as well as mixtures of two or more can be used.

The reaction is generally carried out in the manner such that the compounds of formula (IV) and (V) and the organophosphorous$^{III}$ compound are dissolved together in the suitable solvent and the solution of the aliphatic azo compound is stirred into this. Alternatively, a solution of compounds of formulas (IV) and (V) and the aliphatic azo compound can be added to the solution of the organophosphorous$^{III}$ compound. In order to avoid autoxidation of the organophosphorous$^{III}$ compound, the reaction is suitably carried out under inert gas.

The reaction temperature can vary, depending on the reactivity of the components, in the range of −20° C. to 120° C., preferably between −10° C. and 80° C., particularly preferred between 0° C. and 30° C.

The starting compounds of formula (IV) can be obtained themselves in that carboxylic acids of the formula (II) are reacted with amino alcohols of formula (VI),

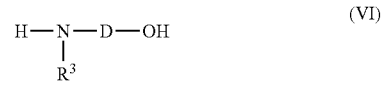

(VI)

in which $R^3$ and D have the meaning given above under conditions as they are described under method (A).

In the following, a series of compounds are listed in tabular form and, in connection with this, further examples for their synthesis are given for a more close illustration of the above described methods for production of the compounds according to the invention.

TABLE 1
Exemplary compounds of formula (I) according to the invention
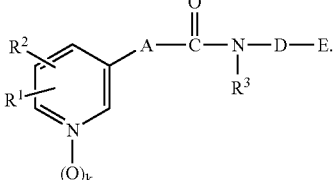
| Nr | R$^1$—R$^2$ | k | —A | R$^3$ | D—E |
|---|---|---|---|---|---|
| 1 | H | 0 | CH=CH | H | 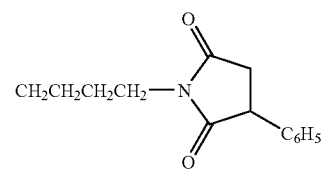 |
| 2 | H | 0 | CH=CH | H | 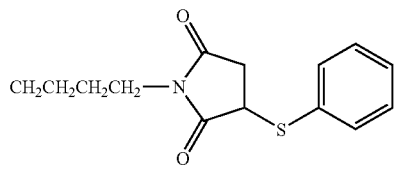 |
| 3 | H | 0 | CH=CH | H | 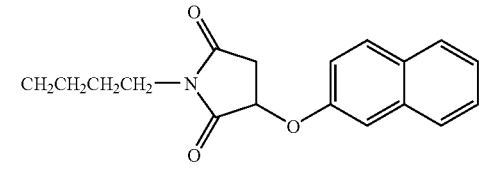 |
| 4 | H | 0 | CH=CH | H | 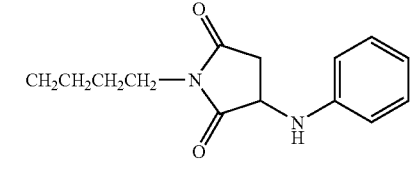 |
| 5 | H | 0 | CH=C(CH$_3$) | H | 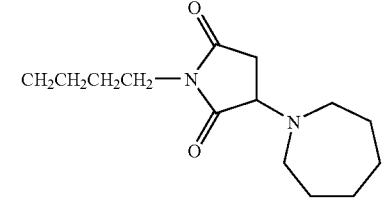 |
| 6 | H | 0 | CH=CH | H | 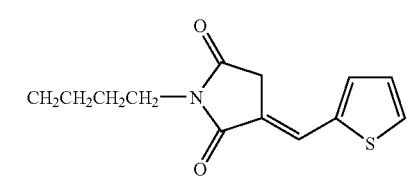 |
| 7 | H | 0 | CH$_2$CHF | H | 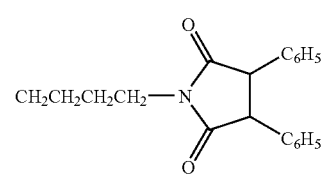 |
| 8 | H | 0 | CH=CH | H | " |

TABLE 1-continued
Exemplary compounds of formula (I) according to the invention
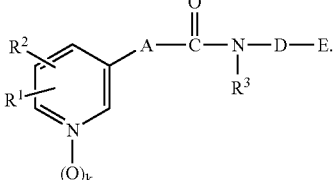
| Nr | R¹—R² | k | —A | R³ | D—E |
|---|---|---|---|---|---|
| 9 | 5-CF₃ | 0 | CH=CH | H | " |
| 10 | H | 0 | CH₂CH₂ | H | 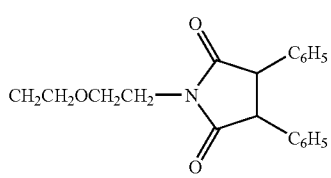 |
| 11 | H | 0 | CH=CH | H | 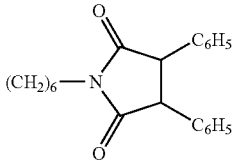 |
| 12 | H | 0 | CH=CH | H | 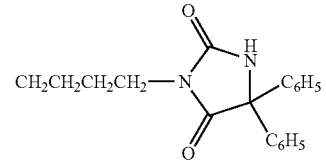 |
| 13 | H | 0 | CH=CH | H | 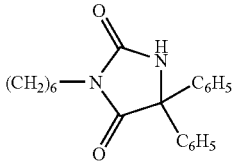 |
| 14 | H | 0 | CH₂CH₂ | H | 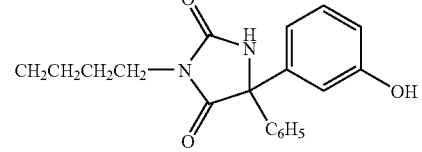 |
| 15 | H | 0 | CH=CH | H | 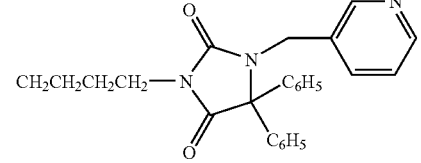 |
| 16 | H | 0 | CH=CH | H | 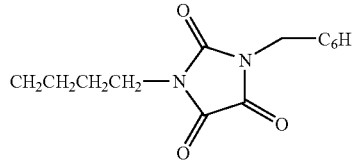 |

TABLE 1-continued
Exemplary compounds of formula (I) according to the invention
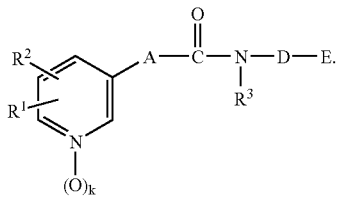
| Nr | R¹—R² | k | —A | R³ | D—E |
|----|-------|---|------|-----|-----|
| 17 | H | 0 | CH=CH | H | (CH₂)₆-N hydantoin-N-CH₂-C₆H₅ |
| 18 | H | 0 | OCH₂ | H | CH₂CH₂CH₂-N hydantoin-N-CH₂-(2-naphthyl) |
| 19 | H | 0 | CH₂CH₂ | H | CH₂CH₂CH₂-N hydantoin-N-CH(C₆H₅)₂ |
| 20 | H | 0 | CH=CH | H | " |
| 21 | H | 0 | CH=CH | H | CH₂C≡CCH₂-N hydantoin-N-CH(C₆H₅)₂ |
| 22 | H | 0 | CH=CH | H | CH₂CH₂CH₂-N hydantoin-N-CH₂-(4-pyridyl) |
| 23 | H | 0 | CH=CH | H | CH₂CH₂CH₂-N thiazolidinedione =CH-C₆H₅ |

TABLE 1-continued
Exemplary compounds of formula (I) according to the invention
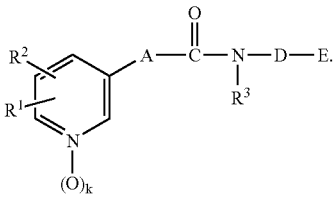
| Nr | R¹—R² | k | —A | R³ | D—E |
|----|-------|---|-----|-----|-----|
| 24 | H | 0 | CH₂CH₂CH₂CH₂ | H | 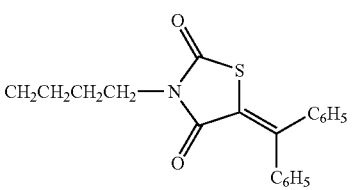 |
| 25 | H | 0 | CH=CH | H | 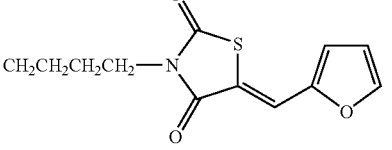 |
| 26 | H | 0 | CH=CH—CH=CH | H | 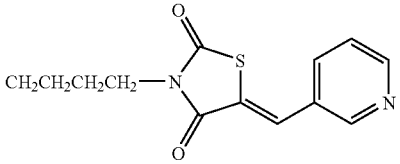 |
| 27 | H | 0 | CH=CH | H | 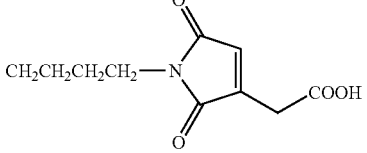 |
| 28 | H | 0 | CH=CH | H | 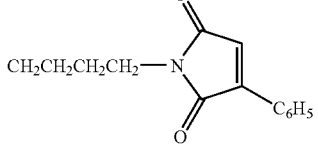 |
| 29 | H | 0 | OCH₂ | H | 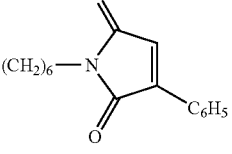 |
| 30 | H | 0 | CH=CH | H | " |

TABLE 1-continued

Exemplary compounds of formula (I) according to the invention

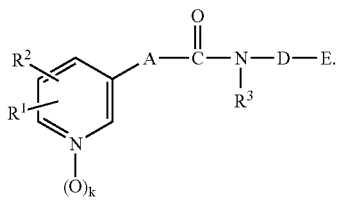

| Nr | R¹—R² | k | —A | R³ | D—E |
|---|---|---|---|---|---|
| 31 | H | 0 | $CH_2CH_2$ | H | (indole-substituted maleimide with $CH_2CH_2CH_2$-N linker) |
| 32 | H | 0 | CH=CH | H | " |
| 33 | H | 0 | $SCH_2$ | H | " |
| 34 | H | 0 | CH=CH | H | (3,4-dichloromaleimide with $CH_2CH_2CH_2$-N linker) |
| 35 | H | 0 | CH=CH | H | (3-bromo-4-phenyl maleimide with $CH_2CH_2CH_2$-N linker) |
| 36 | H | 0 | $CH_2CH_2$ | H | (3,4-diphenyl maleimide with $CH_2CH_2$-N linker) |
| 37 | H | 0 | CH=CH | H | " |
| 38 | H | 0 | CH=CH | H | (3,4-diphenyl maleimide with $CH_2CH_2CH_2$-N linker) |
| 39 | H | 0 | $CH_2$ | H | (3,4-diphenyl maleimide with $CH_2CH_2CH_2CH_2$-N linker) |
| 40 | H | 0 | $CH_2CH_2$ | H | " |
| 41 | H | 0 | $CH_2CH_2$ | $CH_3$ | " |

TABLE 1-continued
Exemplary compounds of formula (I) according to the invention
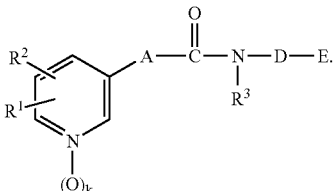
| Nr | R¹—R² | k | —A | R³ | D—E |
|----|-------|---|-----|-----|------|
| 42 | H | 0 | CHCH₂ \| OH | H | " |
| 43 | H | 0 | CH=CH | H | " |
| 44 | H | 1 | CH=CH | H | " |
| 45 | 2-CF₃ | 0 | CH=CH | H | " |
| 46 | 5-F | 0 | CH=CH | H | " |
| 47 | 6-CH₃O | 0 | CH=CH | H | " |
| 48 | 6-C₂H₅S | 0 | CH=CH | H | " |
| 49 | H | 0 | CH=CH | CH₂ \| CH=CH₂ | " |
| 50 | H | 0 | C≡C | H | " |
| 51 | H | 0 | △ | H | " |
| 52 | H | 0 | CH=C \| CH₃ | H | " |
| 53 | H | 0 | CH=C \| C₆H₅ | H | " |
| 54 | H | 0 | CH=CH | H | 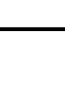 |
| 55 | H | 0 | CH=CH | H | 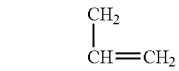 |
| 56 | H | 0 | CH₂CH₂ | H |  |
| 57 | H | 0 | SCH₂ | H |  |

TABLE 1-continued
Exemplary compounds of formula (I) according to the invention
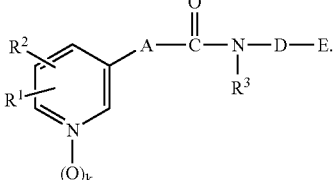
| Nr | R¹—R² | k | —A | R³ | D—E |
|----|-------|---|----|----|-----|
| 58 | H | 0 | CH=CH | H | " |
| 59 | 2-Cl | 0 | CH=CH | H | " |
| 60 | 6-C₆H₅ | 0 | CH=CH | H | " |
| 61 | H | 0 | CH₂CH<br>    |<br>    CH₃ | H | " |
| 62 | H | 0 | CH=C<br>    |<br>    CH₃ | H | " |
| 63 | H | 0 | CH=CH | H | 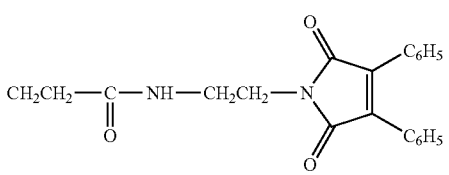 |
| 64 | H | 0 | CH₂CH₂ | H | 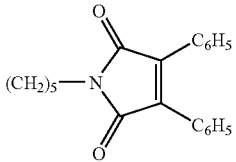 |
| 65 | H | 0 | CH=CH | H | " |
| 66 | H | 0 | CH₂CH₂ | H | 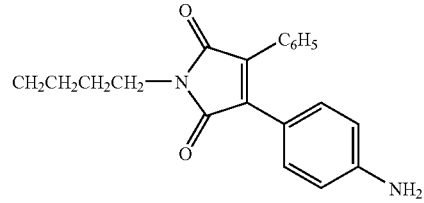 |
| 67 | H | 0 | CH=CH | H | " |
| 68 | H | 0 | CH=CH | H | 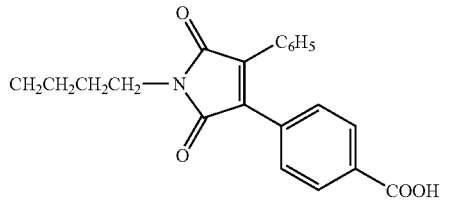 |
| 69 | H | 0 | CH=CH | H | 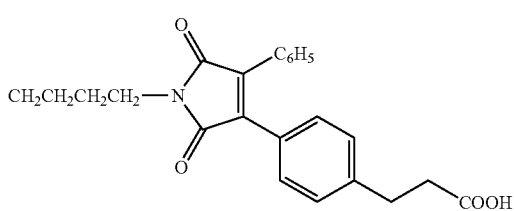 |

TABLE 1-continued
Exemplary compounds of formula (I) according to the invention
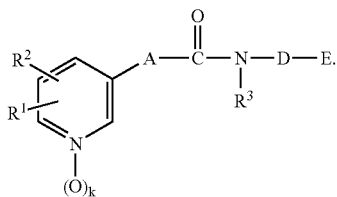
| Nr | R¹—R² | k | —A | R³ | D—E |
|----|-------|---|-----|-----|-----|
| 70 | H | 0 | CH=CH | H | |
| 71 | H | 0 | CH=CH | H | |
| 72 | H | 0 | CH₂CH₂ | H | |
| 73 | H | 0 | OCH₂ | H | " |
| 74 | H | 0 | CH=CH | H | " |
| 75 | H | 0 | CH=CH | H | |
| 76 | H | 0 | CH=CH—CH=CH | H | |

TABLE 1-continued
Exemplary compounds of formula (I) according to the invention
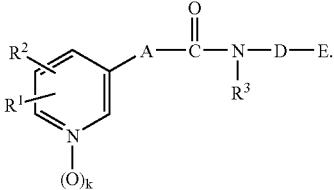
| Nr | R¹—R² | k | —A | R³ | D—E |
|----|-------|---|----|----|-----|
| 77 | H | 0 | CH₂CH₂ | H | 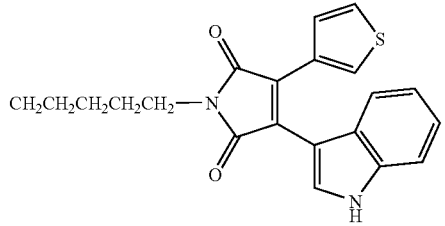 |
| 78 | H | 0 | CH=CH | H | 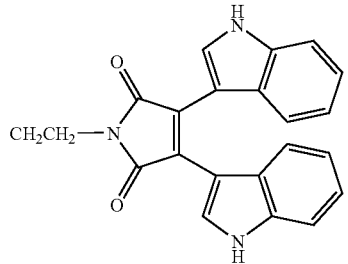 |
| 79 | H | 0 | CH₂CH₂ | H | 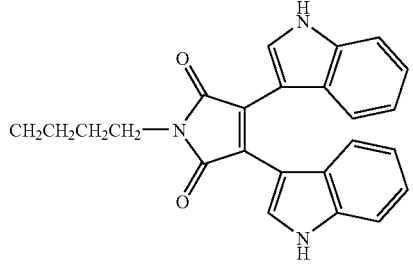 |
| 80 | H | 0 | CHCF₂<br>\|<br>OH | H | " |
| 81 | H | 0 | CH=CH | H | " |
| 82 | H | 0 | CH=CH | H | 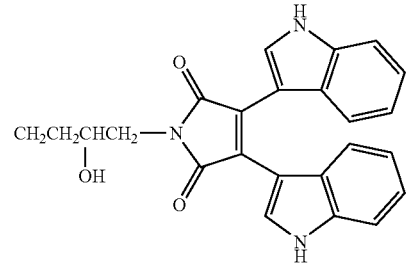 |

TABLE 1-continued
Exemplary compounds of formula (I) according to the invention
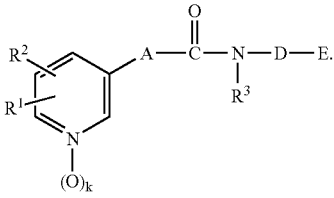
| Nr | R¹—R² | k | —A | R³ | D—E |
|----|-------|---|-----|-----|-----|
| 83 | H | 0 | SCH$_2$ | H | 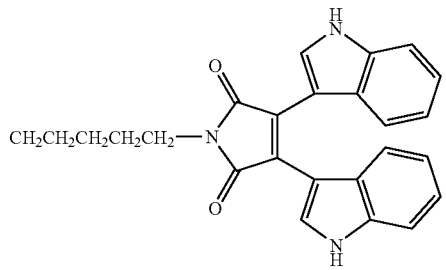 |
| 84 | H | 0 | CH=CH | H | " |
| 85 | H | 0 | CH=CH | H | 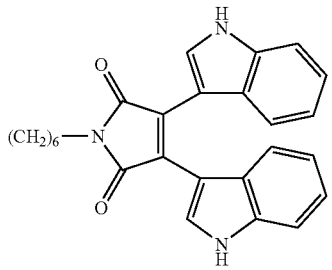 |
| 86 | H | 0 | CH=CH | H | 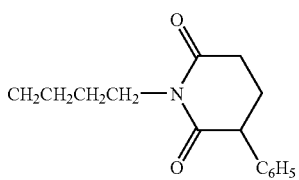 |
| 87 | H | 0 | OCH$_2$ | H | 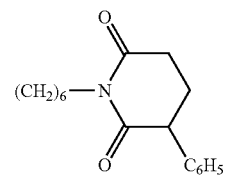 |
| 88 | H | 0 | CH=CH | H | 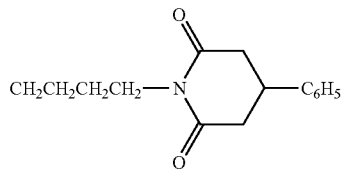 |
| 89 | H | 0 | C≡C | H | " |

TABLE 1-continued
Exemplary compounds of formula (I) according to the invention
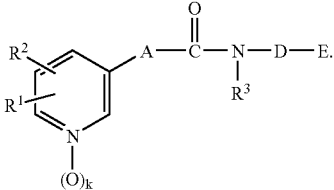
| Nr | R¹—R² | k | —A | R³ | D—E |
|----|-------|---|-----|-----|-----|
| 90 | H | 0 | CH=CH | H | 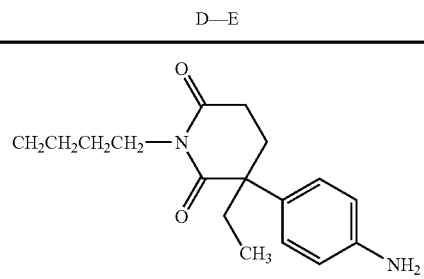 |
| 91 | H | 0 | CH$_2$CH$_2$ | H | 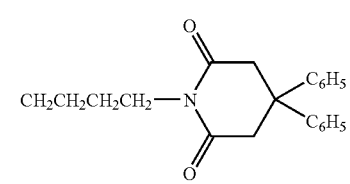 |
| 92 | H | 0 | CH=CH | H | 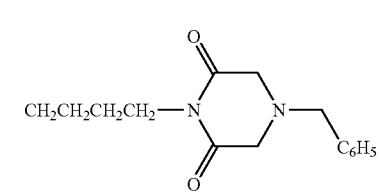 |
| 93 | 5-F | 0 | CH=CH | H | " |
| 94 | H | 0 | CH$_2$CH$_2$ | H | 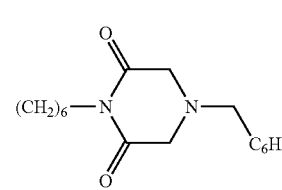 |
| 95 | H | 0 | CH=CH | H | 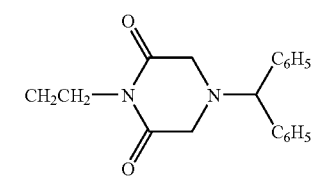 |
| 96 | H | 0 | OCH$_2$ | H | 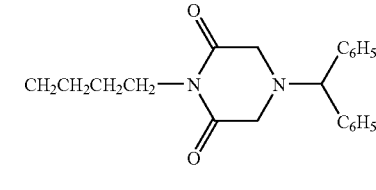 |
| 97 | H | 0 | CH=CH | H | " |

TABLE 1-continued

Exemplary compounds of formula (I) according to the invention

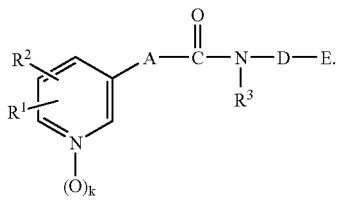

| Nr | R¹—R² | k | —A | R³ | D—E |
|---|---|---|---|---|---|
| 98 | H | 0 | CH=CH | H | CH₂CH₂CH₂CH₂—N(2,6-dioxopiperazin-1-yl)-N'-phenyl |
| 99 | H | 0 | CH₂CH₂ | H | CH₂CH₂CH₂CH₂—N(2,6-dioxopiperazin-1-yl)-N'-(2-phenylphenyl) |
| 100 | H | 0 | CH=CH | H | " |
| 101 | H | 0 | CH=CH | H | CH₂CH₂CH₂CH₂—N(2,6-dioxopiperazin-1-yl)-N'-(1-naphthylmethyl) |
| 102 | H | 0 | CH=CH | H | CH₂CH₂CH₂CH₂—N(2,6-dioxopiperazin-1-yl)-N'-(1-naphthyl) |
| 103 | H | 0 | CH=CH | H | CH₂CH₂CH₂CH₂—N(3,5-dioxo-2,6-diphenylmorpholin-4-yl) |
| 104 | H | 0 | CH₂CH₂ | H | CH₂CH₂CH₂CH₂—N(2,7-dioxo-4,5-diphenyl-4,5-didehydroazepan-1-yl) |
| 105 | H | 0 | CH=CH | H | " |

TABLE 1-continued
Exemplary compounds of formula (I) according to the invention
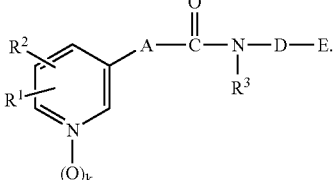
| Nr | R¹—R² | k | —A | R³ | D—E |
|---|---|---|---|---|---|
| 106 | H | 0 | CH=CH | H | 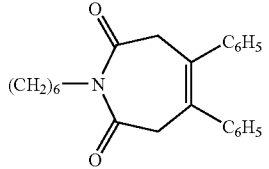 |
| 107 | H | 0 | SCH$_2$ | H | 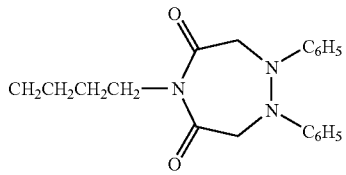 |
| 108 | H | 0 | CH=CH | H | " |
| 109 | 6-C$_2$H$_5$S | 0 | CH=CH | H | " |
| 110 | H | 0 | CH=CH | H | 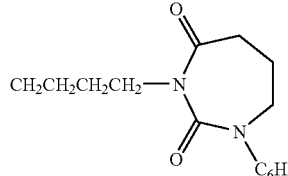 |
| 111 | H | 0 | OCH$_2$CH$_2$ | H | " |
| 112 | H | 0 | CH$_2$CH$_2$ | H | 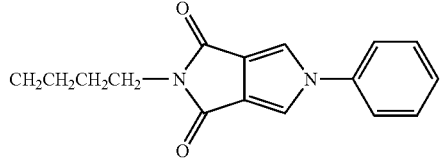 |
| 113 | H | 0 | OCH$_2$ | H | " |
| 114 | H | 0 | CH=CH | H | " |
| 115 | H | 0 | CH$_2$CHF | H | 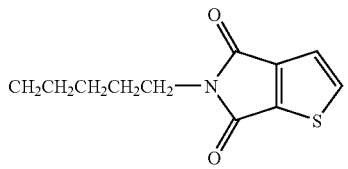 |
| 116 | H | 0 | CH=CH | H | " |
| 117 | H | 0 | CH$_2$CH$_2$ | H | 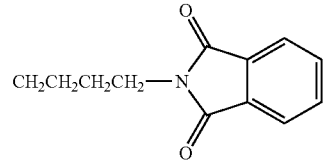 |

TABLE 1-continued
Exemplary compounds of formula (I) according to the invention
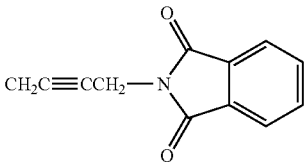
| Nr | R¹—R² | k | —A | R³ | D—E |
|---|---|---|---|---|---|
| 118 | H | 0 | CH=C(F) | H | " |
| 119 | H | 0 | CH=CH | H | " |
| 120 | 6-C₂H₅S | 0 | CH=CH | H | " |
| 121 | H | 0 | CH₂CH₂ | H | CH₂C≡CCH₂-N(phthalimide) |
| 122 | H | 0 | CH=CH | H | CH₂CHCH₂CH₂-N(phthalimide), OH |
| 123 | H | 0 | CH=CH | H | CH₂CH₂CH₂CH₂CH₂-N(phthalimide) |
| 124 | H | 0 | CH=CH—CH=CH | H | CH₂CH₂CH₂CH₂O-N(phthalimide) |
| 125 | H | 0 | C≡C | H | (CH₂)₆-N(phthalimide) |
| 126 | H | 0 | CH=CH | H | CH₂CH₂CH₂CH₂-N(fluorophthalimide) |

TABLE 1-continued
Exemplary compounds of formula (I) according to the invention
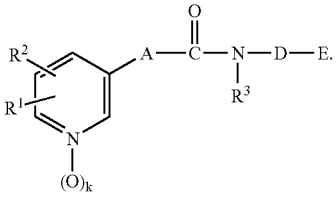
| Nr | R$^1$—R$^2$ | k | —A | R$^3$ | D—E |
|---|---|---|---|---|---|
| 127 | H | 0 | CH=CH | H | 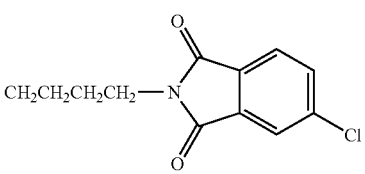 |
| 128 | H | 0 | △ | H | " |
| 129 | H | 0 | CH$_2$CH$_2$ | H |  |
| 130 | H | 0 | CH=CH | H | " |
| 131 | H | 0 | CH=CH | H | 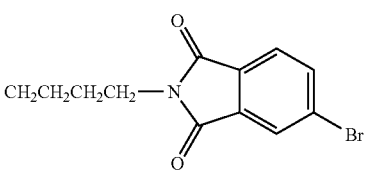 |
| 132 | H | 0 | CH$_2$CH$_2$ | H | 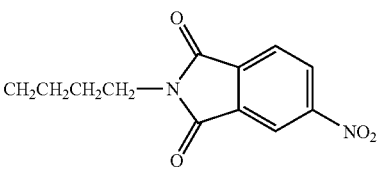 |
| 133 | H | 0 | CH=CH | H | 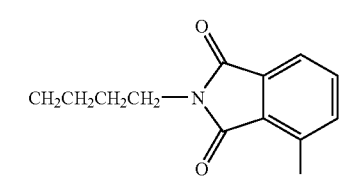 |
| 134 | H | 0 | CH=CH | H | 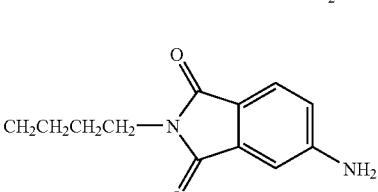 |

TABLE 1-continued
Exemplary compounds of formula (I) according to the invention
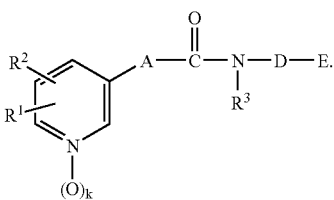
| Nr | R¹—R² | k | —A | R³ | D—E |
|----|-------|---|-----|-----|-----|
| 135 | H | 0 | OCH$_2$ | H | 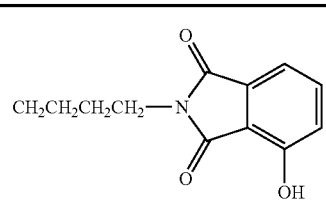 |
| 136 | H | 0 | CH=CH | H | 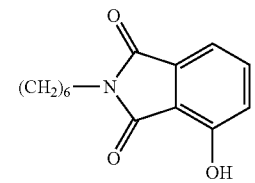 |
| 137 | H | 0 | CH=CH | H | 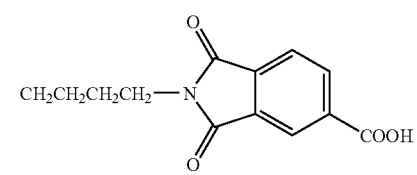 |
| 138 | H | 0 | CH=CH | H | 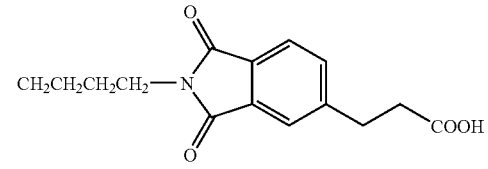 |
| 139 | H | 0 | CH$_2$CH$_2$ | H | 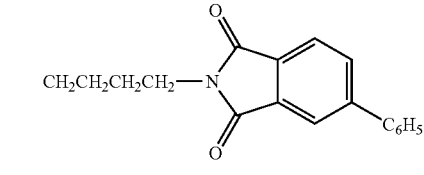 |
| 140 | H | 0 | CH=CH | H | " |
| 141 | H | 0 | CH=CH | H | 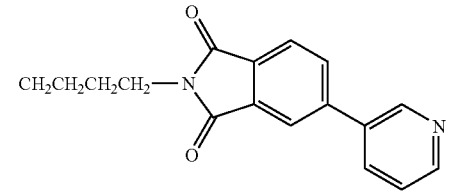 |

TABLE 1-continued

Exemplary compounds of formula (I) according to the invention

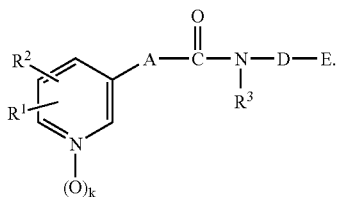

| Nr | R¹—R² | k | —A | R³ | D—E |
|---|---|---|---|---|---|
| 142 | H | 0 | CH₂CH₂ | H | CH₂CH₂CH₂CH₂—N(phthalimide with 2 F substituents) |
| 143 | H | 0 | CH=CH | H | CH₂CH₂CH₂CH₂—N(phthalimide with 2 Cl substituents) |
| 144 | H | 0 | CH=CH | H | CH₂CH₂CH₂CH₂—N(phthalimide with 4 F substituents) |
| 145 | H | 0 | CH=CH | H | CH₂CH₂CH₂CH₂—N(phthalimide with 4 C₆H₅ substituents) |
| 146 | H | 0 | CH=CH | H | (CH₂)₆—N(phthalimide with 4 C₆H₅ substituents) |
| 147 | H | 0 | CH=CH | H | CH₂CH₂CH₂CH₂—N(saccharin-type) |
| 148 | H | 0 | CH=CH—CH=CH | H | " |

TABLE 1-continued
Exemplary compounds of formula (I) according to the invention
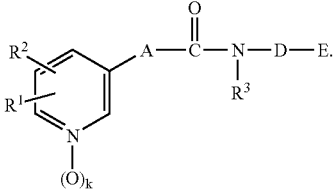
| Nr | R¹—R² | k | —A | R³ | D—E |
|---|---|---|---|---|---|
| 149 | H | 0 | CH₂ | H | 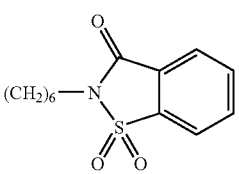 |
| 150 | 6-CH₃O | 0 | CH=CH | H | " |
| 151 | H | 0 | CH=CH | H | 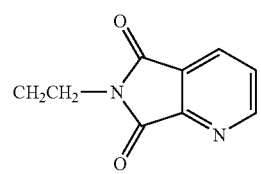 |
| 152 | H | 0 | SCH₂ | H | 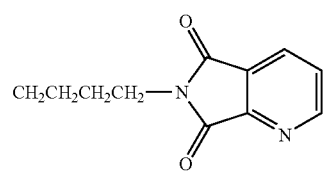 |
| 153 | H | 0 | CH=CH | H | " |
| 154 | H | 0 | C≡C | H | " |
| 155 | H | 0 | CH=CH | H | 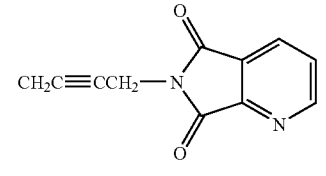 |
| 156 | H | 0 | CH=CH | H | 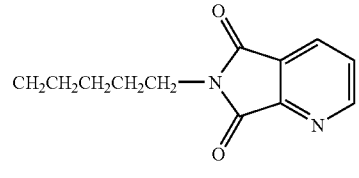 |
| 157 | H | 0 | CH₂CF₂ | H | 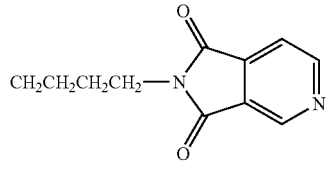 |
| 158 | H | 0 | CH=CH | H | " |
| 159 | H | 0 | CH=CH | C₂H₅ | " |
| 160 | H | 0 |  | H | " |

TABLE 1-continued
Exemplary compounds of formula (I) according to the invention
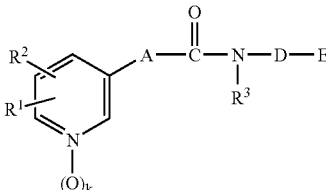
| Nr | R$^1$—R$^2$ | k | —A | R$^3$ | D—E |
|---|---|---|---|---|---|
| 161 | H | 0 | CH=CH | H | 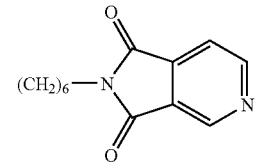 |
| 162 | 5-F | 0 | CH=CH | H | " |
| 163 | H | 0 | CH=CH | H | 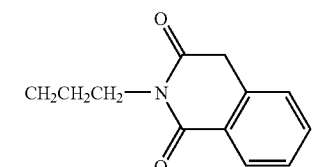 |
| 164 | H | 0 | CH$_2$CH$_2$ | H | 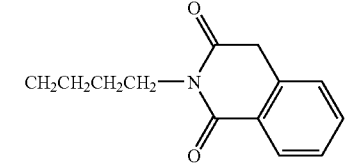 |
| 165 | H | 0 | CH=CH | H | " |
| 166 | 2-Cl | 0 | CH=CH | H | 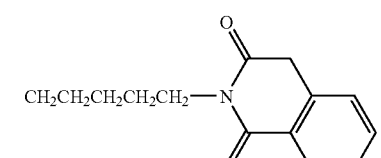 |
| 167 | H | 0 | CH=CH | H | 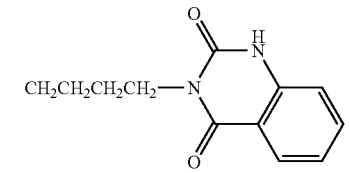 |
| 168 | H | 0 | CH$_2$CH$_2$ | H | 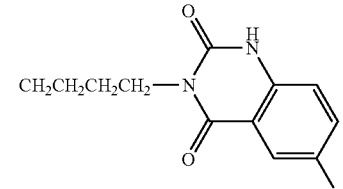 |

TABLE 1-continued
Exemplary compounds of formula (I) according to the invention
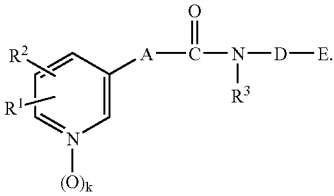
| Nr | R¹—R² | k | —A | R³ | D—E |
|---|---|---|---|---|---|
| 169 | H | 0 | CH=CH | H | 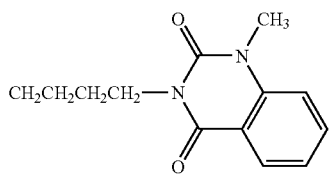 |
| 170 | H | 0 |  | H | " |
| 171 | H | 0 | CH=CH | H | 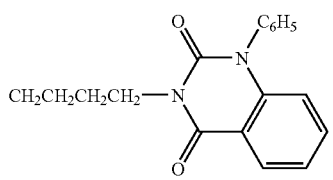 |
| 172 | H | 0 | CH$_2$NHCH$_2$CH$_2$ | H | " |
| 173 | H | 0 | CH$_2$CH$_2$ | H | 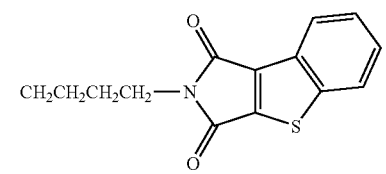 |
| 174 | H | 0 | CH=CH | H | 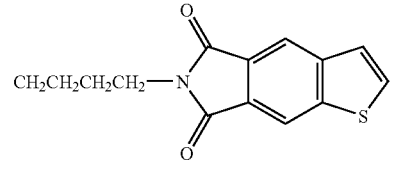 |
| 175 | H | 0 | CH$_2$CH$_2$ | H | 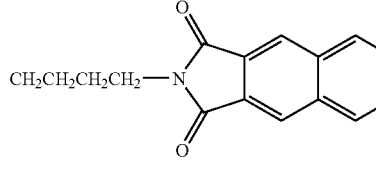 |
| 176 | H | 0 | CH=CH | H | " |
| 177 | 6-C$_2$H$_5$S | 0 | CH=CH | H | " |
| 178 | H | 0 | OCH$_2$ | H | 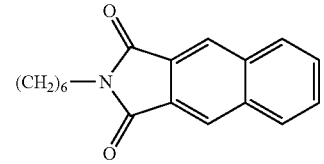 |

TABLE 1-continued
Exemplary compounds of formula (I) according to the invention
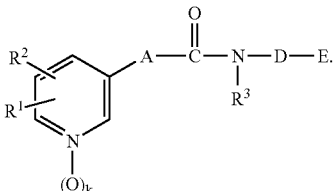
| Nr | R¹—R² | k | —A | R³ | D—E |
|---|---|---|---|---|---|
| 179 | H | 0 | CH=CH | H | 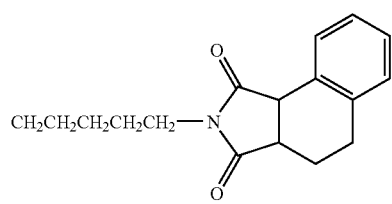 |
| 180 | H | 0 | CH₂CH₂ | H | 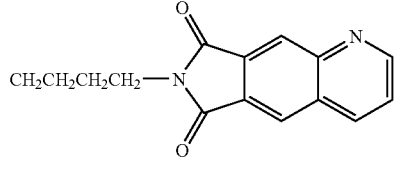 |
| 181 | H | 0 | CH=CH | H | " |
| 182 | H | 0 | CH₂CH₂CH₂CH₂ | H | 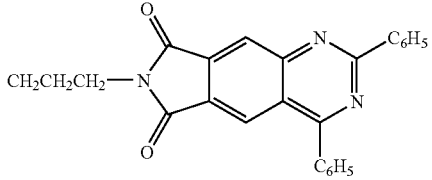 |
| 183 | H | 0 | CH=CH | H | 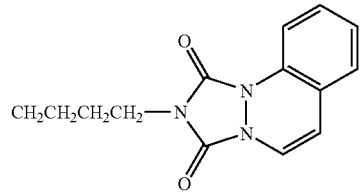 |
| 184 | H | 0 | CH=CH | H | 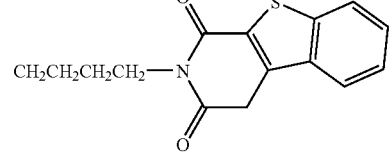 |
| 185 | H | 0 | CH₂CH₂ | H | 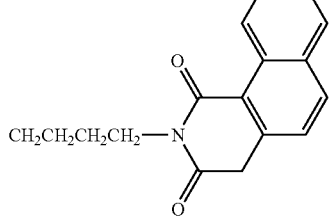 |
| 186 | H | 0 | CH=CH | H | " |

TABLE 1-continued
Exemplary compounds of formula (I) according to the invention
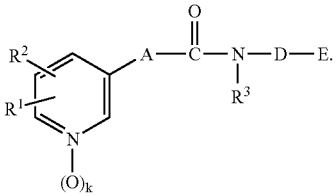
| Nr | R¹—R² | k | —A | R³ | D—E |
|---|---|---|---|---|---|
| 187 | H | 0 | CH=CH | H | 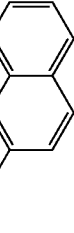 |
| 188 | H | 0 | C≡C | H | " |
| 189 | H | 0 | CH=CH | H | 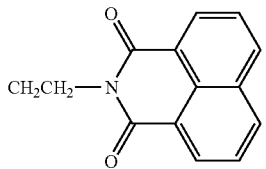 |
| 190 | 4-F | 0 | CH=CH | H | " |
| 191 | H | 0 | CH=CH | H | 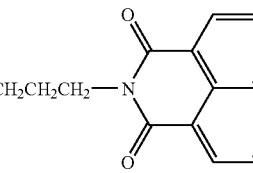 |
| 192 | H | 0 | CH₂CH(OH) | H | 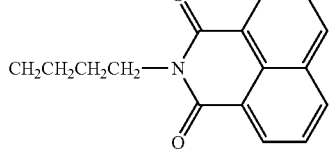 |
| 193 | H | 0 | OCH₂ | H | " |
| 194 | H | 0 | SCH₂ | H | " |
| 195 | H | 0 | CH=CH | H | " |
| 196 | H | 1 | CH=CH | H | " |
| 197 | 5-F | 0 | CH=CH | H | " |
| 198 | 6-CH₂ | 0 | CH=CH | H | " |
| 199 | H | 0 | △ | H | " |
| 200 | H | 0 | CH₂CH₂CH₂CH₂ | H | " |
| 201 | H | 0 | CH=CH | H | 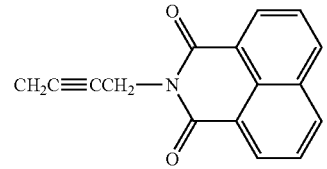 |

TABLE 1-continued

Exemplary compounds of formula (I) according to the invention

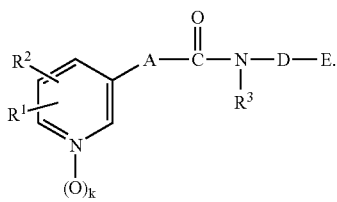

| Nr | R¹—R² | k | —A | R³ | D—E |
|---|---|---|---|---|---|
| 202 | H | 0 | OCH$_2$ | H | CH$_2$CH$_2$CH$_2$CH$_2$—naphthalimide |
| 203 | H | 0 | C≡C | H | " |
| 204 | H | 0 | CH=CH | H | (CH$_2$)$_6$—naphthalimide |
| 205 | 2-CH$_2$O | 0 | CH=CH | H | " |
| 206 | H | 0 | CH=CH—CH=CH | H | " |
| 207 | H | 0 | CH=CH | H | CH$_2$CH$_2$—C(O)—NH—CH$_2$CH$_2$—naphthalimide |
| 208 | H | 0 | CH=CH | H | CH$_2$CH$_2$NH—C(O)—NHCH$_2$CH$_2$—naphthalimide |
| 209 | H | 0 | CH=CH | H | (CH$_2$)$_8$—naphthalimide |
| 210 | H | 0 | CH=CH | H | CH$_2$CH$_2$CH$_2$CH$_2$—naphthalimide-Br |

TABLE 1-continued

Exemplary compounds of formula (I) according to the invention

| Nr | R¹—R² | k | —A | R³ | D—E |
|---|---|---|---|---|---|
| 211 | H | 0 | CH=CH | H | (CH₂)₆-N-naphthalimide-Br |
| 212 | H | 0 | CH₂CH₂ | H | CH₂CH₂CH₂-N-naphthalimide-NO₂ |
| 213 | 6-CH₃ | 0 | CH=CH | H | " |
| 214 | H | 0 | CH=CH | H | CH₂CH₂CH₂-N-naphthalimide-NH₂ |
| 215 | H | 0 | CH=CH | H | CH₂CH₂CH₂-N-naphthalimide-CH₂CH₂COOH |
| 216 | H | 0 | OCH₂ | H | CH₂CH₂CH₂CH₂-N-naphthalimide-NO₂ |
| 217 | H | 0 | CH=CH | H | " |
| 218 | H | 0 | CH=CH | H | CH₂CH₂CH₂-N-naphthalimide-OH |

TABLE 1-continued
Exemplary compounds of formula (I) according to the invention
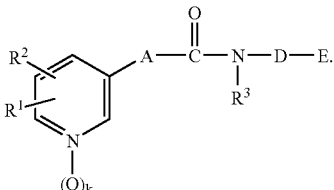
| Nr | R¹—R² | k | —A | R³ | D—E |
|---|---|---|---|---|---|
| 219 | H | 0 | CH=CH | H | 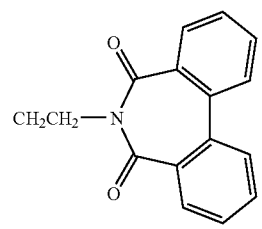 |
| 220 | H | 0 | CH=CH | H | 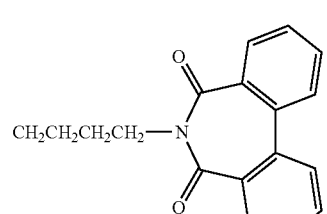 |
| 221 | H | 0 | CH=CH | n-$C_3H_7$ | " |
| 222 | H | 0 | C≡C | H | " |
| 223 | 6-$C_6H_5O$ | 0 | CH=CH | H | 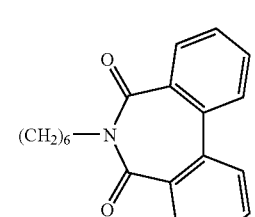 |
| 224 | H | 0 | $CH_2CH_2$ | H | 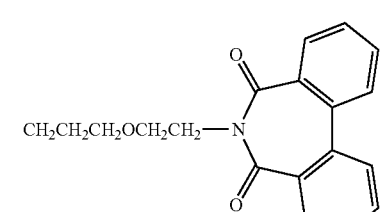 |
| 225 | H | 0 | $CH_2CH_2$ | H | 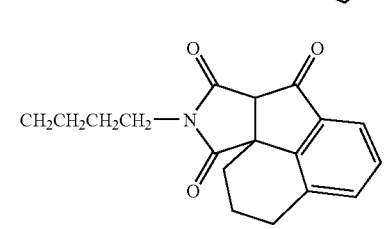 |
| 226 | H | 0 | CH=CH | H | " |
| 227 | H | 0 | C≡C | H | " |

TABLE 1-continued

Exemplary compounds of formula (I) according to the invention

| Nr | R¹—R² | k | —A | R³ | D—E |
|---|---|---|---|---|---|
| 228 | H | 0 | CH=CH | H | CH₂CH₂CH₂CH₂CH₂-N(imide-acenaphthene fused) |
| 229 | H | 0 | SCH₂ | H | (CH₂)₆-N(imide-acenaphthene fused) |
| 230 | H | 0 | CH=CH | H | CH₂CH₂CH₂CH₂-N(phenyl-carbazole-imide, C₆H₅ substituent) |
| 231 | H | 0 | CH=CH | H | CH₂CH=CHCH₂-N(phenyl-carbazole-imide, C₆H₅ substituent) |
| 232 | H | 0 | CH₂CH₂CH₂CH₂ | H | " |
| 233 | H | 0 | CH=CH | H | CH₂CH₂-N(phenanthrene-imide) |

TABLE 1-continued

Exemplary compounds of formula (I) according to the invention

| Nr | R¹—R² | k | —A | R³ | D—E |
|---|---|---|---|---|---|
| 234 | H | 0 | CHCF$_2$ / OH | H | CH$_2$CH$_2$CH$_2$CH$_2$—N(phenanthrene dicarboximide) |
| 235 | H | 0 | CH=CH | H | " |
| 236 | H | 0 | CH$_2$CH$_2$ | H | CH$_2$C≡CCH$_2$—N(phenanthrene dicarboximide) |
| 237 | H | 0 | CH$_2$CH$_2$ | H | CH$_2$CH$_2$CH$_2$CH$_2$—N(anthracene dicarboximide) |
| 238 | H | 0 | CH=CH | H | " |
| 239 | H | 0 | △ | H | CH$_2$CH$_2$—N(anthracene naphthalimide) |
| 240 | H | 0 | OCH$_2$ | H | CH$_2$CH$_2$CH$_2$CH$_2$—N(phenanthrene naphthalimide) |
| 241 | H | 0 | CH$_2$C(=O) | H | " |

TABLE 1-continued
Exemplary compounds of formula (I) according to the invention
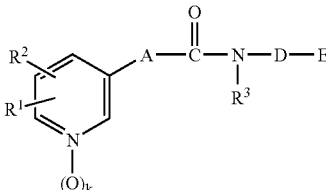
| Nr | R¹—R² | k | —A | R³ | D—E |
|---|---|---|---|---|---|
| 242 | 2,6-(CH₃)₂ | 0 | CH=CH | H | " |
| 243 | H | 0 | SCH₂ | H | 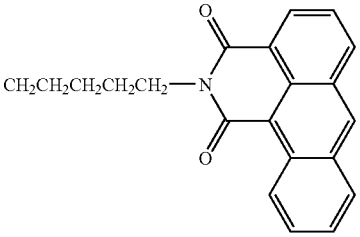 |
| 244 | H | 0 | CH=CH | H | " |
| 245 | H | 0 | CH₂CH₂ | H | 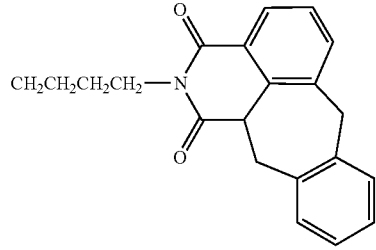 |
| 246 | H | 0 | CH=CH | H | " |
| 247 | H | 0 | CH=CH | H | 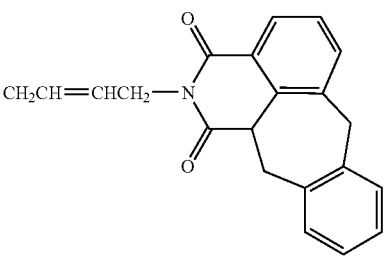 |
| 248 | H | 0 | CH₂CH₂ | H | 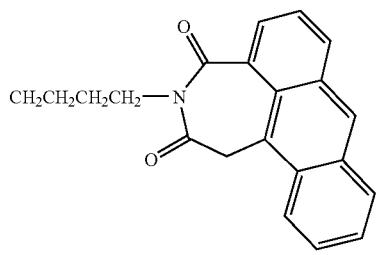 |
| 249 | H | 0 | CH=CH | H | " |
| 250 | H | 0 | CH=CH—CH=CH | H | " |

TABLE 1-continued
Exemplary compounds of formula (I) according to the invention
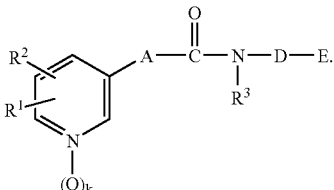
| Nr | R¹—R² | k | —A | R³ | D—E |
|---|---|---|---|---|---|
| 251 | H | 0 | CH=CH | H | 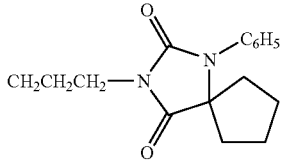 |
| 252 | H | 0 | CH=CH—CH=CH | H | " |
| 253 | H | 0 | CH₂CH₂ | H | 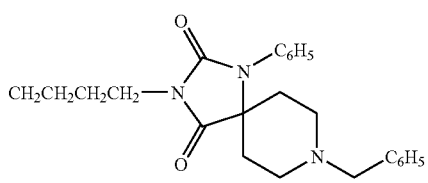 |
| 254 | H | 0 | CH=CH | H | " |
| 255 | H | 0 | CH₂CH₂ | H | 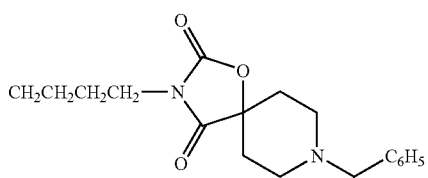 |
| 256 | H | 0 | CH=CH | H | " |
| 257 | H | 0 | CH=CH | H | 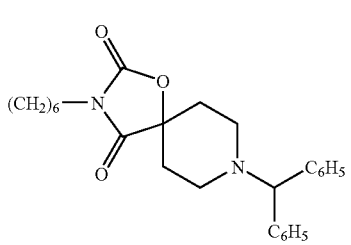 |
| 258 | H | 0 | CH=CH | H | 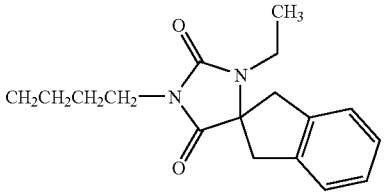 |
| 259 | H | 0 | △ | H | " |

TABLE 1-continued
Exemplary compounds of formula (I) according to the invention
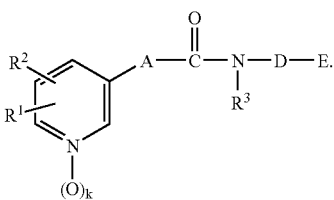
| Nr | R¹—R² | k | —A | R³ | D—E |
|---|---|---|---|---|---|
| 260 | H | 0 | CH=CH | H | 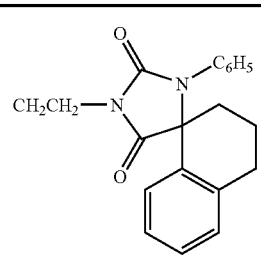 |
| 261 | H | 0 | CH₂CH₂CH₂CH₂ | H | 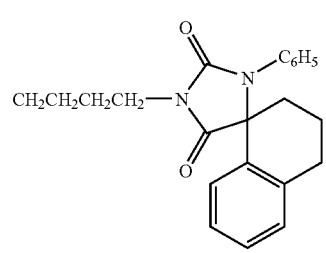 |
| 262 | H | 0 | CH=CH | H | 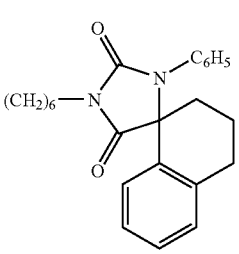 |
| 263 | H | 0 | OCH₃ | H | 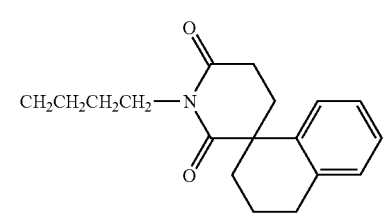 |
| 264 | H | 0 | CH=CH | H | " |
| 265 | H | 0 | CH=CH | H | 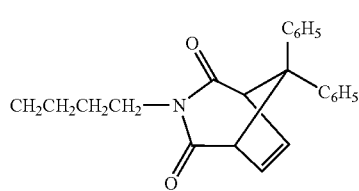 |

TABLE 1-continued

Exemplary compounds of formula (I) according to the invention

| Nr | R¹—R² | k | —A | R³ | D—E |
|---|---|---|---|---|---|
| 266 | H | 0 | CH₂CH₂ | H | CH₂CH₂CH₂CH₂—N[phthalimide-norbornene with two C₆H₅] |
| 267 | H | 0 | CH=CH | H | " |
| 268 | H | 0 | OCH₂ | H | CH₂CH₂OCH₂CH₂—N[phthalimide-norbornene with two C₆H₅] |
| 269 | H | 0 | CH=CH | H | " |
| 270 | H | 0 | CH=CH | H | CH₂CH₂CH₂CH₂—N[oxanorbornene-imide with two C₆H₅] |
| 271 | 6-CH₃ | 0 | CH=CH | H | " |
| 272 | H | 0 | CH=CH | H | CH₂CH₂CH₂CH₂—N[benzo-fused norbornane imide] |
| 273 | H | 0 | △ | H | " |
| 274 | H | 0 | CH=CH | H | (CH₂)₆—N[benzo-fused norbornane imide] |
| 275 | H | 0 | CHCH₂<br>\|<br>OH | H | CH₂CH₂CH₂CH₂—N[dibenzo-fused norbornane imide] |

TABLE 1-continued

Exemplary compounds of formula (I) according to the invention

| Nr | R¹—R² | k | —A | R³ | D—E |
|---|---|---|---|---|---|
| 276 | H | 0 | CH=CH | H | " |
| 277 | H | 0 | CH=CH | H | CH₂CH₂CH₂CH₂CH₂—N(dioxo-dibenzo-bicyclic imide) |
| 278 | H | 0 | CH₂CH₂ | H | CH₂CH₂CH₂CH₂—N(dioxo-dibenzo-bicyclic azepine) |
| 279 | H | 0 | CH=CH | H | " |

SYNTHETIC EXAMPLES FOR THE END PRODUCTS OF THE INVENTION ACCORDING TO FORMULA (I)

In the production examples for the end products, the abbreviations stand for the following terms:

| | |
|---|---|
| MP = | melting point, |
| RT = | room temperature, |
| MPLC = | intermediate pressure liquid chromatography |
| THF = | tetrahydrofuran, |
| DMF = | dimethylformamide, |
| abs. = | absolute, |
| CDI = | carbonyldiimidazole, |
| EDC = | N-(3-dimethylaminopropyl)-N'-ethyl-carbodiimide hydrochloride, |
| HOBT = | 1-hydroxybenzotriazole, |
| TEA = | triethylamine. |

¹H-NMR-Spectrum=proton resonance spectrum, taken at 100 MHz. The chemical shifts are given in ppm against TMS as a standard ($\delta$=0.0), whereby

| | |
|---|---|
| s = | singlet, |
| d = | doublet, |
| t = | triplet, |
| dt = | doublet-triplet, |
| m = | multiplet, |
| ar = | aromatic, |
| py = | pyridine. |

Example 1

N-[4-(2,5-dioxo-3,4-diphenyl-2,5-dihydro-pyrrol-1-yl)-butyl]-3-pyridin-3-yl-acrylamide (substance 43)

3.0 g (20.0 mmol) 3-(3-pyridyl)-acrylic acid are suspended in 40 ml abs. dichloromethane, and after addition of two drops pyridine are cooled to ca. 0° C. in a ice bath under moisture exclusion. 4 ml (46.9 mmol) oxalyl chloride are slowly added and the mixture is first stirred 30 min under ice-cooling and then overnight at RT. Subsequently, the solvent and excess oxalyl chloride are distilled off on a rotary evaporator. In order to completely remove the oxalyl chloride, the colorless residue is further dried for two hours under high vacuum. The acid chloride obtained in this manner is suspended in 30 ml abs. dichloromethane without further purification and cooled to ca. 0° C. in an ice bath under moisture exclusion. 6.3 g (17.6 mmol) 4-(2,5-dioxo-3,4-diphenyl-2,5-dihydropyrrol-1-yl)-butylamine•hydrochloride in 80 ml abs. dichloromethane together with 4.0 g (39.5 mmol) TEA are added together dropwise to this suspension. After complete addition, the ice bath is removed and the reaction is stirred further for two hours at RT. The mixture is subsequently concentrated, taken up in 10% sodium hydroxide solution and extracted three times with acetic acid ethyl ester. The combined organic phases are washed with saturated NaCl solution, dried over sodium sulfate and the solvent is removed under vacuum. The residue is chromatographically purified over silica gel with CHCl₃/CH₃OH (96/4) and, after withdraw of the solvent, crystallized from 65 ml acetic acid ethyl ester: Yellow crystals with MP. 135–137° C.; Yield 5.1 g (64%).

| $C_{28}H_{25}N_3O_3$ (451.5) | |
|---|---|
| IR-Spectrum (KBr): | ν(NH) 3280 cm$^{-1}$ |
| | ν(C=O) 1700, 1660, 1540 cm$^{-1}$ |
| | ν(C=C) 1630 cm$^{-1}$ |
| $^1$H-NMR-Spectrum (CDCl$_3$): | 1.45–1.95(4H, m, C—CH$_2$—CH$_2$—C) |
| | 3.45(2H, dt, CONHCH$_2$, J=6.3Hz, J=12.3Hz) |
| | 3.69(2H, t, (CO)$_2$NCH$_2$, J=6.4Hz) |
| | 6.20–6.40(1H, m, NH) |
| | 6.50(1H, d, CH=CHCO, J=15.7Hz) |
| | 7.20–7.55(11H, m, Ar, Py) |
| | 7.60(1H, d, CH=CHCO, J=5.7Hz) |
| | 7.65–7.80(1H, m, Py) |
| | 8.45–8.60(1H, m, Py) |
| | 8.65–8.80(1H, m, Py) |

Example 2

N-[4-(2,6-dioxo-4-phenyl-piperidin-1-yl)-butyl]-3-pyridin-3-yl-acrylamide (substance 88)

9.3 g (42.3 mmol) N-(4-hydroxy-butyl)-3-pyridin-3-yl-acrylamide, 11.1 g (42.3 mmol) triphenylphosphine and 8.0 g (42.3 mmol) 4-phenyl-piperidin-2,6-dione are suspended in 120 ml THF, thereafter 6.7 ml (42.3 mmol) azodicarboxylic acid diethyl ester dissolved in 60 ml THF are added dropwise within three hours under protective atmosphere and light cooling (to ca. 15° C.). The mixture is left standing overnight without further cooling at RT. Subsequently, the solvent is removed under vacuum and the residue is chromatographically purified over silica gel with CHCl$_3$/CH$_3$OH (95/5) and, after withdraw of the solvent, crystallized from acetic acid ethyl ester: Colorless crystals with MP. 160–161° C.; Yield 3.8 g (23%).

| $C_{23}H_{25}N_3O_3$ (391.5) | |
|---|---|
| IR-Spectrum (KBr): | ν(NH) 3250 cm$^{-1}$ |
| | ν(C=O) 1720, 1650, 1550 cm$^{-1}$ |
| | ν(C=C) 1610 cm$^{-1}$ |
| $^1$H-NMR-Spectrum (CDCl$_3$): | 1.35–1.95(4H, m, C—CH$_2$—CH$_2$—C) |
| | 2.45–3.20(4H, m, piperidindione) |
| | 3.20–3.70(3H, m, piperidindione, CONHCH$_2$) |
| | 3.70–4.10(2H, m, (CO)$_2$NCH$_2$) |
| | 6.35–6.60(1H, m, NH) |
| | 6.54(1H, d, CH=CHCO, J=15.6Hz) |
| | 7.05–7.95(7H, m, Ar, Py) |
| | 7.61(1H, d, CH=CHCO, J=15.6Hz) |
| | 8.40–8.65(1H, m, Py) |
| | 8.65–8.90(1H, m, Py) |

Example 3

N-[4-(1,3-dioxo-4,5,6,7-tetraphenyl-1,3-dihydro-isoindol-2-yl)-butyl]-3-pyridin-3-yl-acrylamide (substance 145)

Production Analogous to Example 1.

Batch size: 1.2 g (8.0 mmol) 3-(3-pyridyl)-acrylic acid, 1.0 ml (11.7 mmol) oxalyl chloride, 1.0 ml (7.3 mmol) TEA and 4.0 g (7.3 mmol) 4-(1,3-dioxo-4,5,6,7-tetraphenyl-1,3-dihydro-isoindolin-2-yl)-butylamine•hydrochloride.

In the purification, chromatography first occurs with CHCl$_3$/CH$_3$OH (96/4); subsequently, crystallization occurs twice from 40 ml 1-chlorobutane and 30 ml acetonitrile: Colorless crystals with MP. 228–230° C.; Yield 2.7 g (56%).

| $C_{44}H_{35}N_3O_3$ (653.8) | | |
|---|---|---|
| IR-Spectrum (KBr): | ν(NH) | 3280 cm$^{-1}$ |
| | ν(C=O) | 1760, 1700, 1670, 1550 cm$^{-1}$ |
| | ν(C=C) | 1630 cm$^{-1}$ |
| $^1$H-NMR-Spectrum (CDCl$_3$): | 1.45–1.85(4H, m, C—CH$_2$—CH$_2$—C) | |
| | 3.25–3.50(2H, m, CONHCH$_2$) | |
| | 3.50–3.75(2H, m, (CO)$_2$NCH$_2$) | |
| | 5.80–6.05(1H, m, NH) | |
| | 6.40(1H, d, CH=CHCO, J=15.7Hz) | |
| | 6.65–7.40(21H, m, Ar, Py) | |
| | 7.58(1H, d, CH=CHCO, J=15.7Hz) | |
| | 7.70–7.85(1H, m, Py) | |
| | 8.50–8.65(1H, m, Py) | |
| | 8.70–8.80(1H, m, Py) | |

Example 4

N-[4-(3-benzyl-2,4,5-trioxo-imidazolidin-1-yl)-butyl]-3-pyridin-3-yl-acrylamide (substance 16)

Production Analogous to Example 2.

Batch size: 4.4 g (20.0 mmol) N-(4-hydroxybutyl)-3-pyridin-3-yl-acrylamide, 5.2 g (19.8 mmol) triphenylphosphine, 4.1 g (20.1 mmol) 3-benzyl-2,4,5-trioxo-imidazolidine (production according to Ishii et al., J. Med. Chem. 39, 1924 (1996)) and 3.5 g (20.0 mmol) azodicarboxylic acid diethyl ester in 60 ml THF.

In the purification, chromatography first occurs with CHCl$_3$/CH$_3$OH (95/5); subsequently, crystallization occurs twice from 50 ml and 30 ml acetic acid ethyl ester: Colorless crystals with MP. 115–117° C.; Yield 1.6 g (19%).

| $C_{22}H_{22}N_4O_4$ (406.4) | | |
|---|---|---|
| IR-Spectrum (KBr): | ν(NH) | 3280 cm$^{-1}$ |
| | ν(C=O) | 1810, 1780, 1730, 1660, 1550 cm$^{-1}$ |
| | ν(C=C) | 1620 cm$^{-1}$ |
| $^1$H-NMR-Spectrum (CDCl$_3$): | 1.45–2.00 (4H, m, C—CH$_2$—CH$_2$—C) | |
| | 3.30–3.55 (2H, m, CONHCH$_2$) | |
| | 3.66 (2H, t, (CO)$_2$NCH$_2$, J=6.3 Hz) | |
| | 4.77 (2H, s, Ar—CH$_2$) | |
| | 6.10–6.35 (1H, m, NH) | |
| | 6.49 (1H, d, CH=CHCO, J=15.7 Hz) | |
| | 7.20–7.60 (6H, m, Ar, Py) | |
| | 7.59 (1H, d, CH=CHCO, J=15.7 Hz) | |
| | 7.65–7.90 (1H, m, Py) | |
| | 8.50–8.65 (1H, m, Py) | |
| | 8.65–8.85 (1H, m, Py) | |

Example 5

N-[4-(1,3,10-trioxo-1,4,5,6,10,10a-hexahydro-acenaphtho[1,8a-c]pyrrol-2-yl)-butyl]-3-pyridin-3-yl-acrylamide (substance 226)

Production Analogous to Example 2.

Batch size: 4.4 g (20.0 mmol) N-(4-hydroxy-butyl)-3-pyridin-3-yl-acrylamide, 5.2 g (19.8 mmol) triphenylphosphine, 4.8 g (19.9 mmol) 7,8-dihydroacenaphthen-2(6H)-on-1,8a-dicarboximide and 3.5 g (20.0 mmol) azodicarboxylic acid diethyl ester in 65 ml THF.

In the purification, chromatography first occurs with CHCl$_3$/CH$_3$OH (95/5 to 92/8); subsequently, crystallization occurs twice from 70 ml and 90 acetic acid ethyl ester: Colorless crystals with MP. 159–161° C. in a Yield of 5.0 g (56%).

| C$_{26}$H$_{25}$N$_3$O$_4$ (443.5) | | |
|---|---|---|
| IR-Spectrum (KBr): | ν(NH) | 3320 cm$^{-1}$ |
| | ν(C=O) | 1770, 1710, 1680, 1650, 1540 cm$^{-1}$ |
| | ν(C=C) | 1620 cm$^{-1}$ |
| $^1$H-NMR-Spectrum (CDCl$_3$): | 1.20–2.15 | (6H, m, C—CH$_2$—CH$_2$—C, Ring) |
| | 2.20–3.00 | (3H, m, Ring) |
| | 3.15–3.75 | (5H, m, CONHC<u>H</u>$_2$, (CO)$_2$NCH$_2$, Ring) |
| | 3.64 | (1H, s, CO—CH—CO) |
| | 6.40–6.70 | (1H, m, NH) |
| | 6.57 | (1H, d, CH=C<u>H</u>CO, J=15.6 Hz) |
| | 7.20–7.90 | (6H, m, Ar, Py, C<u>H</u>=CHCO) |
| | 8.45–8.65 | (1H, m, Py) |
| | 8.65–8.90 | (1H, m, Py) |

Example 6

N-[4-(2,5-dioxo-4,4-diphenyl-imidazolidin-1-yl)-butyl-3-pyridin-3-yl-acrylamide (substance 12)

Production Analogous to Example 2.

Batch size: 6.0 g (27.2 mmol) N-(4-hydroxybutyl)-3-pyridin-3-yl-acrylamide, 7.1 g (27.2 mmol) triphenylphosphine, 6.9 g (27.2 mmol) 5,5-diphenylhydantoin and 4.3 ml (27.2 mmol) azodicarboxylic acid diethyl ester in 100 ml THF.

In the purification, pre-purification chromatography first occurs with CHCl$_3$/CH$_3$OH (95/5 to 90/10) and this is further purified by flash chromatography with CHCl$_3$/CH$_3$OH (95/5): Amorphous solid with MP. 83–85° C.; Yield 0.9 g (7%).

| C$_{27}$H$_{26}$N$_4$O$_3$ (454.5) | | |
|---|---|---|
| IR-Spectrum (KBr): | ν(NH) | 3250 cm$^{-1}$ |
| | ν(C=O) | 1760, 1700, 1655, 1540 cm$^{-1}$ |
| | ν(C=C) | 1615 cm$^{-1}$ |
| $^1$H-NMR-Spectrum (CDCl$_3$): | 1.40–1.90 | (4H, m, C—CH$_2$—CH$_2$—C) |
| | 3.20–3.75 | (4H, m, CONHC<u>H</u>$_2$, (CO)$_2$NCH$_2$) |
| | 6.25–6.45 | (1H, m, NH) |
| | 6.46 | (1H, d, CH=C<u>H</u>CO, J=15.7 Hz) |
| | 7.15–7.45 | (12H, m, Ar, Py, NH) |
| | 7.58 | (1H, d, C<u>H</u>=CHCO, J=15.7 Hz) |
| | 7.60–7.85 | (1H, m, Py) |
| | 8.45–8.60 | (1H, m, Py) |
| | 8.60–8.80 | (1H, m, Py) |

Example 7

N-[4-(2,5-dioxo-3-phenyl-2,5-dihydropyrrol-1-yl)-butyl]-3-pyridin-3-yl-acrylamide (substance 28)

2.7 g (17.8 mmol) 3-(3-pyridyl)-acrylic acid and 1.8 g (17.8 mmol) TEA are suspended in 50 ml abs. dichloromethane and cooled to ca. 0° C. under moisture exclusion. 3.1 g (17.8 mmol) 88% HOBT and 3.4 g (17.8 mmol) EDC are added and the mixture is stirred for 30 min under ice cooling. 5.0 g (17.8 mmol) 4-(2,5-dioxo-3-phenyl-2,5-dihydropyrrol-1-yl)-butylamine hydrochloride are dissolved in 30 ml abs. dichloromethane and added dropwise under ice cooling. The mixture is stirred overnight at RT without further cooling. Subsequently, the batch is washed with 25 ml 1M NaOH and with 50 ml water. The organic phase is dried over sodium sulfate and the solvent is removed under vacuum. The resinous residue is chromatography pre-purified over silica gel with CHCl$_3$/CH$_3$OH (95/5) and further purified by flash chromatography with CHCl$_3$/CH$_3$OH (95/5). After withdraw of the solvent, this is crystallized from acetic acid ethyl ester: Colorless crystals with MP. 141–143° C.; Yield 0.6 g (9%).

| C$_{22}$H$_{21}$N$_3$O$_3$ (375.4) | | |
|---|---|---|
| IR-Spectrum (KBr): | ν(NH) | 3270 cm$^{-1}$ |
| | ν(C=O) | 1750, 1690, 1650, 1540 cm$^{-1}$ |
| | ν(C=C) | 1610 cm$^{-1}$ |
| $^1$H-NMR-Spectrum (CDCl$_3$) | 1.35–2.00 | (4H, m, C—CH$_2$—CH$_2$—C) |
| | 3.20–3.80 | (4H, m, CONHC<u>H</u>$_2$, (CO)$_2$NCH$_2$) |
| | 6.15–6.45 | (1H, m, NH) |
| | 6.51 | (1H, d, CH=C<u>H</u>CO, J=15.7 Hz) |
| | 6.73 | (1H, s, CH=C) |
| | 7.15–8.10 | (8H, m, Ar, Py, C<u>H</u>=CHCO) |
| | 8.45–8.65 | (1H, m, Py) |
| | 8.65–8.85 | (1H, m, Py) |

Example 8

N-[3-(2,5-dioxo-3,4-diphenyl-2,5-dihydropyrrol-1-yl)-propyl]-3-pyridin-3-yl-acrylamide (substance 38)

Production Analogous to Example 1.

Batch size: 3.4 g (23.1 mmol) 3-(3-pyridyl)-acrylic acid, 5.3 g (42,0 mmol) oxalyl chloride, 4.2 g (42.0 mmol) TEA and 7.2 g (21.0 mmol) 3-(2,5-dioxo-3,4-diphenyl-2,5-dihydropyrrol-1-yl)-propylamine•hydrochloride.

In the purification, chromatography first occurs with CHCl$_3$/CH$_3$OH (90/10); subsequently, crystallization occurs twice from 400 ml acetic acid ethyl ester and 150 ml ethanol: Colorless crystals with MP. 163–164° C.; Yield 1.6 g (17%).

| C$_{27}$H$_{23}$N$_3$O$_3$ (437.5) | | |
|---|---|---|
| IR-Spectrum (KBr): | ν(NH) | 3270 cm$^{-1}$ |
| | ν(C=O) | 1760, 1690, 1660, 1535 cm$^{-1}$ |
| | ν(C=C) | 1620 cm$^{-1}$ |
| $^1$H-NMR-Spectrum (CDCl$_3$): | 1.75–2.15 | (2H, m, C—CH$_2$—C) |
| | 3.42 | (2H, dt, CONHC<u>H</u>$_2$, J=6.1 Hz, J=12.1 Hz) |
| | 3.78 | (2H, t, (CO)$_2$NCH$_2$, J=6.1 Hz) |
| | 6.54 | (1H, d, CH=C<u>H</u>CO, J=15.7 Hz) |
| | 6.55–6.80 | (1H, m, NH) |
| | 7.20–7.60 | (11H, m, Ar, Py) |
| | 7.63 | (1H, d, C<u>H</u>=CHCO, J=15.7 Hz) |
| | 7.70–7.90 | (1H, m, Py) |
| | 8.50–8.60 | (1H, m, Py) |
| | 8.65–8.80 | (1H, m, Py) |

Example 9

N-[4-(3-pyridin-3-yl-acroylamino)-butyl]-2,3:5,6-dibenzobicyclo[2.2.2]octan-7,8-dicarboximide (substance 276)

Production Analogous to Example 1.

Batch size: 1.7 g (11.4 mmol) 3-(3-pyridyl)-acrylic acid, 2.2 g (17.5 mmol) oxalyl chloride, 1.6 ml (11.7 mmol) TEA and 4.5 g (11.7 mmol) N-(4-amino-butyl)-2,3:5,6dibenzobicyclo[2.2.2]oc-tan-7,8-dicarboximide•hydrochloride.

In the purification, chromatography first occurs with $CHCl_3/CH_3OH$ (95/5) and this is subsequently crystallized from 100 ml 1-chlorobutane: Yellow crystals with MP. 213–215° C.; Yield 2.5 g (45%).

| $C_{30}H_{27}N_3O_3$ (477.6) | | |
|---|---|---|
| IR-Spectrum (KBr): | ν(NH) | 3360 cm$^{-1}$ |
| | ν(C=O) | 1780, 1690, 1670, 1550 cm$^{-1}$ |
| | ν(C=C) | 1630 cm$^{-1}$ |
| $^1$H-NMR-Spectrum (CDCl$_3$): | 0.70–1.30 (4H, m, C—CH$_2$—CH$_2$—C) | |
| | 2.90–3.50 (6H, m, CONHC$\underline{H}_2$, (CO)$_2$NCH$_2$, ArCH) | |
| | 4.79 (2H, s, COCHCHCO) | |
| | 5.90–6.10 (1H, m, NH) | |
| | 6.49 (1H, d, CH=C$\underline{H}$CO, J=15.7 Hz) | |
| | 7.00–7.60 (9H, m, Ar, Py) | |
| | 7.63 (1H, d, C$\underline{H}$=CHCO, J=15.7 Hz) | |
| | 7.70–7.95 (1H, m, Py) | |
| | 8.50–8.70 (1H, m, Py) | |
| | 8.70–8.95 (1H, m, Py) | |

Example 10

N-[4-(5-benzyliden-2,4-dioxothiazolidin-3-yl)-butyl]-3-pyridin-3-yl-acrylamide (substance 23)

Production Analogous to Example 2.

Batch size: 13.5 g (61.3 mmol) N-(4-hydroxybutyl)-3-pyridin-3-yl-acrylamide, 16.1 g (61.3 mmol) triphenylphosphine, 12.6 g (61.3 mmol) 5-benzyliden-thiazolidin-2,4-dione and 9.7 ml (61.3 mmol) azodicarboxylic acid diethyl ester in 250 ml THF.

A precipitate forms in the reaction. This is filtered off and crystallized twice from methanol: Colorless solid with MP. 161–162° C.; Yield 11.0 g (44%).

| $C_{22}H_{21}N_3O_3S$ (407.5) | | |
|---|---|---|
| IR-Spectrum (KBr): | ν(NH) | 3330 cm$^{-1}$ |
| | ν(C=O) | 1735, 1670, 1650, 1520 cm$^{-1}$ |
| | ν(C=C) | 1610 cm$^{-1}$ |
| $^1$H-NMR-Spectrum (CDCl$_3$): | 1.45–2.00 (4H, m, C—CH$_2$—CH$_2$—C) | |
| | 3.30–3.60 (2H, m, CONHC$\underline{H}_2$) | |
| | 3.81 (2H, t, (CO)$_2$NCH$_2$, J=6.6 Hz) | |
| | 6.00–6.30 (1H, m, NH) | |
| | 6.49 (1H, d, CH=C$\underline{H}$CO, J=15.7 Hz) | |
| | 7.20–7.60 (6H, m, Ar, Py) | |
| | 7.62 (1H, d, C$\underline{H}$=CHCO, J=15.7 Hz) | |
| | 7.60–7.90 (1H, m, Py) | |
| | 7.90 (1H, s, Ar—CH) | |
| | 8.50–8.65 (1H, m, Py) | |
| | 8.65–8.80 (1H, m, Py) | |

Example 11

N-[4-(4-benzyl-2,6-dioxo-piperazin-1-yl)-butyl]-3-pyridin-3-yl-acrylamide (substance 92)

Production Analogous to Example 7

Batch size: 1.9 g (12.7 mmol) 3-(3-pyridyl)-acrylic acid, 6.2 ml (44.3 mmol) TEA, 2.4 g (15.6 mmol) 88% HOBT, 3.0 g (15.6 mmol) EDC and 5.0 g (14.3 mmol) 4-(4-benzyl-2,6-dioxo-piper-azin-1-yl)-butylamine•dihydrochloride in 70 ml abs. dichloromethane.

For purification, this is chromatographically purified over silica gel with $CHCl_3/CH_3OH$ (96/4 to 95/5); Yield of colorless resin 3.3 g (62%).

| $C_{23}H_{26}N_4O_3$ (406.5) | | |
|---|---|---|
| IR-Spectrum (KBr): | ν(NH) | 3270 cm$^{-1}$ |
| | ν(C=O) | 1730, 1670, 1540 cm$^{-1}$ |
| | ν(C=C) | 1620 cm$^{-1}$ |
| $^1$H-NMR-Spectrum (CDCl$_3$): | 1.45–1.80 (4H, m, C—CH$_2$—CH$_2$—C) | |
| | 3.30–3.95 (10H, m, CONHC$\underline{H}_2$, piperazine, (CO)$_2$NCH$_2$, NCH$_2$) | |
| | 6.00–6.25 (1H, m, NH) | |
| | 6.48 (1H, d, CH=C$\underline{H}$CO, J=15.7 Hz) | |
| | 7.15–7.45 (6H, m, Ar, Py) | |
| | 7.61 (1H, d, C$\underline{H}$=CHCO, J=15.7 Hz) | |
| | 7.65–7.90 (1H, m, Py) | |
| | 8.50–8.65 (1H, m, Py) | |
| | 8.65–8.80 (1H, m, Py) | |

Example 12

N-[6-(2,5-dioxo-3,4-diphenyl-2,5-dihydropyrrol-1-yl)-hexyl])-3-pyridin-3-yl-acrylamide (substance 58)

Production Analogous to Example 1.

Batch size: 2.6 g (17.4 mmol) 3-(3-pyridyl)-acrylic acid, 4.1 ml (47.4 mmol) oxalyl chloride, 4.8 ml (34.7 mmol) TEA and 5.5 g (15.8 mmol) 6-(2,5-dioxo-3,4-diphenyl-2,5-dihydropyrrol-1-yl)-hexylamine•hydrochloride.

In the purification, chromatography first occurs with $CHCl_3/CH_3OH/NH_4OH$ (90/10/1) and subsequently, crystallization occurs twice from 1-chlorobutane and acetic acid ethyl ester respectively: Colorless crystals with MP. 102–104° C. Yield 1.3 g (17%).

| $C_{30}H_{29}N_3O_3$ (479.6) | | |
|---|---|---|
| IR-Spectrum (KBr): | ν(NH) | 3250 cm$^{-1}$ |
| | ν(C=O) | 1760, 1690, 1660, 1540 cm$^{-1}$ |
| | ν(C=C) | 1620 cm$^{-1}$ |
| $^1$H-NMR-Spectrum (CDCl$_3$): | 1.10–1.90 (8H, m, C—(CH$_2$)$_4$—C) | |
| | 3.20–3.50 (2H, m, CONHC$\underline{H}_2$) | |
| | 3.66 (2H, t, (CO)$_2$NCH$_2$, J=6.6 Hz) | |
| | 6.00–6.25 (1H, m, NH) | |
| | 6.51 (1H, d, CH=C$\underline{H}$CO, J=15.7 Hz) | |
| | 7.10–7.60 (11H, m, Ar, Py) | |
| | 7.60 (1H, d, C$\underline{H}$=CHCO, J=15.7 Hz) | |
| | 7.65–7.85 (1H, m, Py) | |
| | 8.45–8.65 (1H, m, Py) | |
| | 8.65–8.80 (1H, m, Py) | |

Example 13

N-[4-(2,5-dioxo-3,4-diphenyl-2,5-dihydropyrrol-1-yl)-butyl]-3-pyridin-3-yl-propionamide (substance 40)

Production Analogous to Example 1.

Batch size: 2.1 g (13.8 mmol) 3-(3-pyridyl)-propionic acid, 1.6 ml (47.4 mmol) oxalyl chloride, 3.8 ml (27.4 mmol) TEA and 4.0 g (12.5 mmol) 4-(2,5-dioxo-3,4-diphenyl-2,5-dihydropyrrol-1-yl)-butylamine•hydrochloride.

In the purification, chromatography first occurs with $CHCl_3/CH_3OH$ (95/5) and subsequently crystallization occurs from 50 ml isopropanol: Colorless crystals with MP. 121–123° C.; Yield 3.7 g (65%).

| $C_{28}H_{27}N_3O_3$ (453.5) | | |
|---|---|---|
| IR-Spectrum (KBr): | ν(NH) | 3280 cm$^{-1}$ |
| | ν(C=O) | 1770, 1700, 1650, 1540 cm$^{-1}$ |
| $^1$H-NMR-Spectrum (CDCl$_3$): | 1.25–1.85 (4H, m, C—CH$_2$—CH$_2$—C) | |
| | 2.45 (2H, t, CO—CH$_2$, J=7.3 Hz) | |
| | 2.97 (2H, t, Py-CH$_2$, J=7.4 Hz) | |
| | 3.28 (2H, dt, CONHC$\underline{H}_2$, J=6.5 Hz, J=12.5 Hz) | |
| | 3.63 (2H, t, (CO)$_2$NCH$_2$, J=6.5 Hz) | |
| | 5.70–5.95 (1H, m, NH) | |
| | 7.10–7.70 (12H, m, Ar, Py) | |
| | 8.35–8.55 (2H, m, Py) | |

Example 14

N-[4-(1,3-dioxo-1,3-dihydro-isoindol-2-yl)-butyl]-3-pyridin-3-yl-acrylamide (substance 119)

Production Analogous to Example 2.

Batch size: 7.8 g (35.4 mmol) N-(4-hydroxybutyl)-3-pyridin-3-yl-acrylamide, 9.3 g (35.4 mmol) tripdhenylphosphine, 5.2 g (35.4 μmmol) phthalimide and 6.2 g (35.4 mmol) azodicarboxylic acid diethyl ester in 100 ml THF.

In the purification, chromatography first occurs with $CHCl_3/CH_3OH$ (100/0 to 90/10) and subsequently crystallization occurs twice from 130 ml and 100 ml isopropanol. Colorless crystals with MP. 172–174° C. Yield 2.4 g (19%).

| $C_{20}H_{19}N_3O_3$ (349.4) | | |
|---|---|---|
| IR-Spectrum (KBr): | ν(NH) | 3380 cm$^{-1}$ |
| | ν(C=O) | 1800, 1730, 1680, 1560 cm$^{-1}$ |
| | ν(C=C) | 1640 cm$^{-1}$ |
| $^1$H-NMR-Spectrum (CDCl$_3$): | 1.40–2.00 (4H, m, C—CH$_2$—CH$_2$—C) | |
| | 3.46 (2H, dt, CONHC$\underline{H}_2$, J=6.3 Hz, J=11.9 Hz) | |
| | 3.73 (2H, t, (CO)$_2$NCH$_2$, J=6.5 Hz) | |
| | 6.20–6.55 (1H, m, NH) | |
| | 6.52 (1H, d, CH=C$\underline{H}$CO, J=15.7 Hz) | |
| | 7.20–7.40 (1H, m, Py) | |
| | 7.61 (1H, d, C$\underline{H}$=CHCO, J=15.7 Hz) | |
| | 7.60–8.00 (5H, m, Ar, Py) | |
| | 8.50–8.65 (1H, m, Py) | |
| | 8.65–8.85 (1H, m, Py) | |

Example 15

N-[4-(1,3-dioxo-1H,3H-benzo[de]isoquinolin-2-yl)-butyl-3-(1-oxidopyridin-3-yl)-acrylamide (substance 196)

5.0 g (12.5 mmol) N-[4-(1,3-dioxo-1H,3H-benzo[de]isoquinolin-2-yl)-butyl]-3-pyridin-3-yl-acrylamide (substance 195) are dissolved in chloroform and cooled to ca. 0° C. under moisture exclusion. 2.8 g (11.3 mmol) 3-chloroperoxybenzoic acid (ca. 70%) are dissolved in chloroform and added dropwise. The mixture is stirred without further cooling for two hours at RT. Subsequently, 30 ml saturated potassium carbonate solution is added and the batch is extracted with 100 ml chloroform. The organic phase is dried over sodium sulfate and the solvent is removed under vacuum. The residue is chromatographically purified over silica gel with $CHCl_3/CH_3OH$ (98/2 to 90/10) and, after withdraw of the solvent, crystallized from 300 ml ethanol. The crystalizate is dissolved in methanol and evaporated several times in a rotary evaporator under addition of toluene: Yield 1.8 g (35%) as an amorphous solid.

| $C_{24}H_{21}N_3O_4$ (415.4) | | |
|---|---|---|
| IR-Spectrum (KBr): | ν(NH) | 3180 cm$^{-1}$ |
| | ν(C=O) | 1690, 1660, 1580, 1540 cm$^{-1}$ |
| | ν(C=C) | 1620 cm$^{-1}$ |
| $^1$H-NMR-Spectrum ((CD$_3$)$_2$SO): | 1.35–1.90 (4H, m, C—CH$_2$—CH$_2$—C) | |
| | 3.10–3.50 (2H, m, CONHC$\underline{H}_2$) | |
| | 3.95–4.20 (2H, m, (CO)$_2$NCH$_2$) | |
| | 6.70 (1H, d, CH=C$\underline{H}$CO, J=15.8 Hz) | |
| | 7.15–7.60 (3H, m, Py, C$\underline{H}$=CHCO) | |
| | 7.75–8.00 (2H, m, Ar) | |
| | 8.10–8.35 (2H, m, Ar) | |
| | 8.40–8.65 (5H, m, Py, Ar, NH) | |

Example 16

N-[6-(1,3-dioxo-1H,3H-benzo[de]isoquinolin-2-yl)-hexyl]-3-pyridin-3-yl-acrylamide (substance 204)

Production Analogous to Example 1.

Batch size: 5.3 g (35.5 mmol) 3-(3-pyridyl)-acrylic acid, 12.4 g (97.9 mmol) oxalyl chloride and 8.6 g (32.6 mmol) 6-(1,3-dioxo-1H, 3H-benzo[de]isoquinolin-2-yl)-hexylamine.

In the purification, chromatography first occurs with $CHCl_3/CH_3OH$ (97/3), and subsequently crystallization occurs twice from 500 ml and 400 ml acetic acid ethyl ester: Colorless crystals with MP. 146–148° C.; Yield 3.8 g (27%).

| $C_{26}H_{25}N_3O_3$ (427.5) | | |
|---|---|---|
| IR-Spectrum (KBr): | ν(NH) | 3250 cm$^{-1}$ |
| | ν(C=O) | 1690, 1650, 1585, 1560 cm$^{-1}$ |
| | ν(C=C) | 1610 cm$^{-1}$ |
| $^1$H-NMR-Spectrum (CDCl$_3$): | 1.35–2.00 (8H, m, C—(CH$_2$)$_4$—C) | |
| | 3.40 (2H, dt, CONHC$\underline{H}_2$, J = 6.0 Hz, J = 11.8 Hz) | |
| | 4.19 (2H, t, (CO)$_2$NCH$_2$, J = 6.8 Hz) | |
| | 6.15–6.40 (1H, m, NH) | |
| | 6.58 (1H, d, CH=C$\underline{H}$CO, | |

Example 17

N-[2-(1,3-dioxo-1H, 3H-benzo [de]isoquinolin-2-yl)-ethyl]-3-pyridin-3-yl-acrylamide (substance 189)

Production Analogous to Example 1.

Batch size: 7.5 g (50.4 mmol) 3-(3-pyridyl)-acrylic acid, 17.4 g (137.4 mmol) oxalyl chloride and 11.0 g (45.8 mmol) 2-(1,3-dioxo-1H, 3H-benzo[de]isoquinolin-2-yl)-ethylamine.

In the purification, chromatography first occurs with $CHCl_3/CH_3OH$ (97/3), and subsequently crystallization occurs from 1000 ml isopropanol: colorless crystals with MP. 195° C.; Yield 8.8 g (52%).

$C_{22}H_{17}N_3O_3$ (371.4)

| | | |
|---|---|---|
| IR-Spectrum (KBr): | ν(NH) | 3270 cm$^{-1}$ |
| | ν(C=O) | 1690, 1650, 1580, 1550 cm$^{-1}$ |
| | ν(C=C) | 1615 cm$^{-1}$ |
| $^1$H-NMR-Spectrum (CDCl$_3$): | 3.80 (2H, dt, CONHCH$_2$, J=5.1 Hz, J=10.6 Hz) | |
| | 4.49 (2H, t, (CO)$_2$NCH$_2$, J=5.3 Hz) | |
| | 6.42 (1H, d, CH=CHCO, J=15.7 Hz) | |
| | 6.60–6.85 (1H, m, NH) | |
| | 7.15–7.35 (1H, m, Py) | |
| | 7.48 (1H, d, CH=CHCO, J=15.7 Hz) | |
| | 7.60–7.85 (3H, m, Ar, Py) | |
| | 8.05–8.30 (2H, m, Ar) | |
| | 8.40–8.75 (4H, m, Ar, Py) | |

Example 18

N-[4-(1,3-dioxo-1H,3H-benzo[de]isoquinolin-2-yl)-butyl]-3-pyridin-3-yl-acrylamide (substance 195)

Production Analogous to Example 1.

Batch size: 6.1 g (41.0 mmol) 3-(3-pyridyl)-acrylic acid, 14.2 g (111.8 mmol) oxalyl chloride and 10.0 g (37.3 mmol) 4-(1,3-dioxo-1H,3H-benzo[de]isoquinolin-2-yl)-butylamine.

In the purification, chromatography first occurs with $CHCl_3/CH_3OH$ (99/1 to 97/3), and subsequently crystallization occurs from 650 ml acetic acid ethyl ester. Colorless crystals with MP. 166–167° C. Yield 6.6 g (44%).

$C_{24}H_{21}N_3O_3$ (399.5)

| | | |
|---|---|---|
| IR-Spectrum (KBr): | ν(NH) | 3280 cm$^{-1}$ |
| | ν(C=O) | 1690, 1650, 1580, 1550 cm$^{-1}$ |
| | ν(C=C) | 1615 cm$^{-1}$ |
| $^1$H-NMR-Spectrum (CDCl$_3$): | 1.50–2.00 (4H, m, C—CH$_2$—CH$_2$—C) | |
| | 3.52 (2H, dt, CONHCH$_2$, J=6.4 Hz, J=12.3 Hz) | |
| | 4.22 (2H, t, (CO)$_2$NCH$_2$, J=7.0 Hz) | |
| | 6.35–6.60 (1H, m, NH) | |
| | 6.55 (1H, d, CH=CHCO, J=15.7 Hz) | |
| | 7.15–7.40 (1H, m, Py) | |
| | 7.61 (1H, d, CH=CHCO, J=15.7 Hz) | |
| | 7.65–7.85 (3H, m, Ar, Py) | |
| | 8.05–8.30 (2H, m, Ar) | |
| | 8.40–8.80 (4H, m, Ar, Py) | |

Production of the Starting Substances

Example i 4-(2,5-dioxo-3,4-diphenyl-2,5-dihydropyrrol-1-yl)-butylamine hydrochloride a) N-(tert-butoxycarbonyl)-1,4-diaminobutane:

38 g (0.6 mol) di-tert-butyldicarbonate, dissolved in 300 ml dioxane, are added dropwise to a solution of 110 g (1.25 mol) 1,4-diaminobutane in dioxane. Subsequently, the suspension is left standing overnight. The mixture is filtered and the filtrate is concentrated under vacuum. The residue is taken up in 700 ml water and filtered again. The filtrate is extracted first with 50 ml toluene and thereafter three times each with 200 ml dichloromethane. The combined dichloromethane phases are washed three times with 20 ml water each, dried over sodium sulfate; subsequently, the solvent is removed under vacuum. The accumulated crude product is further processed without further purification: Yield 23.0 g (76%).

b) N-[4-(2,5-dioxo-3,4-diphenyl-2,5-dihydropyrrol-1-yl)-butyl]-carbamic acid tert-butyl ester:

3.4 g (18 mmol) N-(tert-butoxycarbonyl)-1,4-diaminobutane, dissolved in 50 ml toluene, are added dropwise at RT to a solution of 4.5 g (18 mmol) 2,3-diphenylmaleinic acid anhydride in 120 ml toluene; thereafter, the mixture is subsequently stirred for 10 hours at RT. After withdraw of the solvent, the residue is dissolved in 200 ml chloroform and washed with 50 ml water. The organic phase is dried over sodium sulfate and the solvent is removed under vacuum. The residue is chromatographically purified over silica gel with $CHCl_3/CH_3OH$ (97/3): Yield 8.2 g.

c) 4-(2,5-dioxo-3,4-diphenyl-2,5-dihydropyrrol-1-yl)-butylamine•hydrochloride:

8.2 g (<18 mmol) N-[4-(2,5-dioxo-3,4-diphenyl-2,5-dihydropyr-rol-1-yl)-butyl]-carbamic acid tert-butylester are dissolved in 80 ml ethanol and heated under reflux for two hours after addition of 4.5 ml (54 mmol) concentrated hydrochloric acid. The cooled solution is concentrated under vacuum and the residue is dried under high vacuum. The accumulated crude product is further processed without further purification: Yield 6.3 g of a yellow solid.

Example ii

N-(4-hydroxybutyl)-3-pyridin-3-yl-acrylamide a) 3-(pyridin-3-yl)-acrylic acid-(N-hydroxysuccinimide ester):

38.5 g (335 mmol) N-hydroxysuccinimide and 76.0 g (369 mmol) dicyclohexylcarbodiimide are dissolved in 700

—continued

| | |
|---|---|
| | J = 15.7 Hz) |
| | 7.20–7.35 (1H, m, Py) |
| | 7.62 (1H, d, CH=CHCO, J = 15.7 Hz) |
| | 7.65–7.90 (3H, m, Ar, Py) |
| | 8.10–8.30 (2H, m, Ar) |
| | 8.45–8.85 (4H, m, Ar, Py) | ml dioxane and 50.0 g (335 mmol) 3-(3-pyridyl)-acrylic acid are added. The suspension is stirred at RT for 20 hours. The mixture is filtered and the filtrate is concentrated under vacuum. The residue is recrystallized twice each from 400 ml isopropanol: Yield 36.2 g (44%).

b) N-(4-hydroxybutyl)-3-pyridin-3-yl-acrylamide:

19 g (77.1 mmol) 3-(pyridin-3-yl)-acrylic acid-(N-hydroxysuccinimide ester) are dissolved in 200 ml THF and 6.9 g (77.1 mmol) 4-amino-1-butanol are added. The mixture is stirred at RT for three days. After withdraw of the solvent, the residue is chromatography purified over silica gel with CHCl$_3$/CH$_3$OH (90/10): Yield 10.7 g (63%).

Example iii 4-phenyl-piperidin-2,6-dione 29.0 g (139 mmol) 3-phenylglutaric acid and 8.4 g (139 mmol) urea are stirred at 150° C. for 1.5 hours. After cooling, the reaction mixture is recrystallized from methanol: Yield 20.9 g (79%).

Example iv 4-(1,3-dioxo-4,5,6,7-tetraphenyl-1,3-dihydro-isoindol-2-yl)-butylamine•hydrochloride a) N-[4-(1,3-dioxo-4,5,6,7-tetraphenyl-1,3-dihydro-isoindol-2-yl)-butyl]-carbamic acid tert-butyl ester:

The reaction of the anhydride with the amine occurs analogously to Example i)b).

Batch size: 4.8 g (10.6 mmol) tetraphenylphthalic acid anhydride and 1.9 g (10.6 mmol) N-(tert-butoxycarbonyl)-1,4-diaminobutane in 40 ml toluene.

The reaction mixture is heated under reflux for 5 hours. Purification occurs by chromatography on silica gel with chloroform. Yield 6.3 g (95%).

b) 4-(1,3-dioxo-4,5,6,7-tetraphenyl-1,3-dihydro-isoindol-2-yl)-butylamine•hydrochloride:

The release of the amine occurs analogously to Example i)c).

Batch size: 5.3 g (8.5 mmol) N-(4-(1,3-dioxo-4,5,6,7-tetra-phenyl-1,3-dihydro-isoindol-2-yl)-butyl]-carbamic acid tert-butyl ester and 2.8 ml (33 mmol) concentrated hydrochloric acid in 100 ml ethanol.

The reaction time is increased to four hours and the accumulated crude product is further processed without further purification: Yield 4.2 g (76%).

Example v 4-(2,5-dioxo-3-phenyl-2,5-dihydropyrrol-1-yl)-butylamine•hydrochloride a) N-[4-(2,5-dioxo-3-phenyl-2,5-dihydropyrrol-1-yl)-butyl]-carbamic acid tert-butyl ester:

Reaction of the anhydride with the amine occurs analogously to Example i)b).

Batch size: 6.8 g (39.0 mmol) phenylmaleinic acid anhydride and 7.4 g (39.0 mmol) N-(tert-butoxycarbonyl)-1,4-diaminobutane in 200 ml toluene.

The reaction mixture is stirred at 80° C. for 6 hours, thereafter, purification occurs by chromatography on silica gel with chloroform/methanol (97/3): Yield 6.3 g (47%).

b) 4-(2,5-dioxo-3-phenyl-2,5-dihydropyrrol-1-yl)-butylamine•hydrochloride:

The release of the amine occurs analogously to Example 19c.

Batch size: 6.2 g (18.0 mmol) N-[4-(2,5-dioxo-3-phenyl-2,5-dihydropyrrol-1-yl)-butyl]-carbamic acid tert-butyl ester and 4.0 ml (48 mmol) concentrated hydrochloric acid in 70 ml ethanol.

The accumulated crude product is further processed without further purification: Yield 5.0 g (99%).

Example vi 3-(2,5-dioxo-3,4-diphenyl-2,5-dihydropyrrol-1-yl)-propylamine•hydrochloride a) N-(tert-butoxycarbonyl)-1,3-diaminopropane:

The production of the mono-protected diamine occurs analogously to Example i)a).

Batch size: 42.1 g (0.193 mol) di-tert-butyldicarbonate and 100 g (1.35 mol) 1,3-diaminopropane in 1000 ml dioxane.

The accumulated crude product is further processed without further purification. Yield 23.7 g (70%) of a colorless oil.

b) N-[3-(2,5-dioxo-3,4-diphenyl-2,5-dihydropyrrol-1-yl)-propyl]-carbamic acid tert-butyl ester:

The reaction of the anhydride with the amine occurs analogously to Example 19b.

Batch size: 7.0 g (28.0 mmol) 2,3-diphenylmaleinic acid anhydride and 4.9 g (28.0 mmol) N-(tert-butoxycarbonyl)-1,3-diaminopropane in 140 ml toluene.

The reaction mixture is stirred at 80° C. for 3 hours. Purification occurs by chromatography on silica gel with chloroform/methanol (98/2): Yield 9.7 g (85%).

c) 3-(2,5-dioxo-3,4-diphenyl-2,5-dihydropyrrol-1-yl)-propyl-amine•hydrochloride:

The release of the amine occurs analogously to Example 19c.

Batch size: 9.7 g (23.9 mmol) N-[3-(2,5-dioxo-3,4-diphenyl-2,5-dihydropyrrol-1-yl)-propyl]-carbamic acid tert-butyl ester and 5.4 ml (65 mmol) concentrated hydrochloric acid in 90 ml ethanol.

The accumulated crude product is further processed without further purification: Yield 7.4 g (90%).

Example vii

N-(4-amino-butyl)-2,3:5,6-dibenzobicyclo[2.2.2]octan-7,8-dicarboximide•hydrochloride a) N-[4-(tert-butoxycarbonyl)-aminobutyl]-2,3:5,6-dibenzobicyc-lo[2.2.2]octan-7,8-dicarboximide:

The reaction of the anhydride with the amine occurs analogously to Example I)b).

Batch size: 11.1 g (40.2 mmol) 2,3:5,6-dibenzobicyclo [2.2.2]-octan-7,8-dicarboxylic acid anhydride (production according to Kalindjian et al., J. Med. Chem. 38, 4294 (1995)) and 8.3 g (44.1 mmol) N-(tert-butoxycarbonyl)-1,4-diaminobutane in 200 ml toluene.

The accumulated crude product is further processed without further purification. Yield 16.7 g (93%).

b) N-(4-amino-butyl)-2,3:5,6-dibenzobicyclo[2.2.2]octan-7,8-dicarboximide•hydrochloride:

The release of the amine occurs analogously to Example i)c).

Batch size: 16.7 g (37.4 mmol) N-[4-(tert-butoxycarbonyl)-aminobutyl]-2,3:5,6-dibenzobicyclo[2.2.2]octan-7,8-dicarboximide and 8.9 ml (108 mmol) concentrated hydrochloric acid in 200 ml ethanol.

The reaction mixture is heated under reflux for 10 hours. The accumulated crude product is recrystallized from 600 ml ethanol: Yield 9.0 g (62%).

Example (viii)

5-benzyliden-thiazolidin-2,4-dione 13.6 ml (135.0 mmol) benzaldehyde, 23.7 g (202.5 mmol) 2,4-thiazolidindione and 2.7 ml (27.0 mmol) piperidine are stirred in 400 ml ethanol under reflux for 13 hours. The resulting precipitate is filtered off and dried: Yield 17.1 g (61%).

Example ix 4-(4-benzyl-2,6-dioxopiperazin-1-yl)-butylamine-dihydro-chloride a) N-[4-(4-benzyl-2,6-dioxopiperazin-1-yl)-butyl]-carbamic acid tert-butyl ester:

17.2 g (72.2 mmol) N-benzyliminodiacetic acid and 28.4 g (173.4 mmol) CDI are heated under reflux and under moisture exclusion in 250 ml THF. After an hour, this is cooled to RT and 13.6 g (72.2 mmol) N-(tert-butoxycarbonyl)-1,4-diaminobutane, dissolved in 20 ml THF, are added dropwise. After complete addition, the mixture is heated under reflux for a further 24 hours. After cooling, this is concentrated under vacuum. The residue is taken up in 150 ml acetic acid ethyl ester and washed three times each with 70 ml water. The organic phase is dried over sodium sulfate and the solvent is removed under vacuum. The residue is purified by chromatography over silica gel with $CHCl_3/CH_3OH$ (98/2): Yield 15.0 g (55%) of a).

b) 4-(4-benzyl-2,6-dioxopiperazin-1-yl)-butylamine•dihydro-chloride:

The release of the amine occurs analogously to Example i)c).

Batch size: 14.5 g (38.6 mmol) N—[4-(4-benzyl-2,6-dioxo-piperazine-1-yl)-butyl]-carbamic acid tert-butyl ester and 9.5 ml (115 mmol) concentrated hydrochloric acid in 100 ml ethanol.

The reaction mixture is heated under reflux for three hours. Subsequent thereto, the accumulated crude product is recrystallized from 80 ml methanol: Yield 8.1 g (60%).

Example x 6-(2,5-dioxo-3,4-diphenyl-2,5-dihydropyrrol-1-yl)-hexylamine•Hydrochloride a) N-(tert-butoxycarbonyl)-1,6-diaminohexane:

The production of the mono-protected diamine occurs analogously to Example i)a).

Batch size: 31.2 g (0.143 mol) di-tert-butyl dicarbonate and 116 g (1.0 mol) 1,6-diaminohexane in 1000 ml dioxane.

In the work-up, the filtrate is first extracted with 50 ml toluene and thereafter with 200 ml dichloromethane. The combined organic phases are washed three times each with 20 ml water, dried over sodium sulfate and, subsequently, the solvent is removed under vacuum. The accumulated crude product is further processed without further purification: Yield 24.6 g (79%) of a colorless oil.

b) N-[6-(2,5-dioxo-3,4-diphenyl-2,5-dihydropyrrol-1-yl)-hexyl]-carbamic acid tert-butyl ester:

The reaction of the anhydride with the amine occurs analogously to Example i(b).

Batch size: 5.0 g (20.0 mmol) 2,3-diphenylmaleinic acid anhydride and 4.3 g (20.0 mmol) N-(tert-butoxycarbonyl)-1,6-diaminohexane in 100 ml toluene.

The reaction mixture is stirred at 80° C. for 5 hours. The purification occurs by chromatography on silica gel with chloroform/methanol (97/3): Yield 8.9 g (99%).

c) 6-(2,5-dioxo-3,4-diphenyl-2,5-dihydropyrrol-1-yl)-hexylamine•hydrochloride:

The release of the amine occurs analogously to Example i(c).

Batch size: 8.0 g (17.8 mmol) N-[6-(2,5-dioxo-3,4-diphenyl-2,5-dihydropyrrol-1-yl)-hexyl]-carbamic acid tert-butyl ester and 4.0 ml (48 mmol) concentrated hydrochloric acid in 70 ml ethanol.

The accumulated crude product is further processed without further purification: Yield 5.6 g (90%) of a yellow amorphous solid.

Example xi 4-(1,3-dioxo-1H,3H-benzo[de]isoquinolin-2-yl)-butylamine 20 g (100.9 mmol) naphthalic acid anhydride and 9.9 g (111.0 mmol) 1,4-diaminobutane are stirred in 250 ml toluene at 80° C. for 6 hours. After cooling, the reaction mixture is concentrated under vacuum, taken up in 200 ml water and extracted three times each with 300 ml chloroform. The combined organic phases are dried over sodium sulfate and the solvent is removed under vacuum. The residue is taken up with 150 ml acetic acid ethyl ester and filtered off from the insoluble portion. The solvent is removed under vacuum and the accumulated crude product is further processed without further purification: Yield 13.0 g (48%).

Example xii 6-(1,3-dioxo-1H, 3H-benzo [de] isoquinoline-2-yl)-hexylamine

The reaction of the anhydride with the amine occurs analogously to Example x).

Batch size; 15.0 g (75.7 mmol) naphthalic acid anhydride and 9.7 g (83.2 mmol) 1,6-diaminohexane in 200 ml toluene.

The accumulated crude product is further processed without further purification: Yield 8.6 g (43%).

Example xiii 2-(1,3-dioxo-1H,3H-benzo[de]isoquinolin-2-yl)-ethylamine

The reaction of the anhydride with the amine occurs analogously to Example x).

Batch size: 15.0 g (75.7 mmol) naphthalic acid anhydride and 5.0 g (83.2 mmol) ethylenediamine in 180 ml toluene.

In the work-up, the extraction residue is not taken up in acetic acid ethyl ester, but rather; is further processed without further purification: Yield 13.8 g (76%) of a colorless oil.

The active ingredients according to the invention can be processed to the desired medicaments in the form of their acid addition salts, hydrates or solvates individually or in combination with each other, optionally under addition of other active ingredients. In the case of the combination of active ingredients according to the invention with other medicinals, these can also optionally be separately present next to each other in the medicine packaging, for example as tablets next to vials, depending on the requirements.

Further subject-matter of the invention is a method for the treatment of the human or animal body in which a compound or compound mixture according to formula (I), wherein the substituents have the above described meanings, is administered for treatment of tumors and/or as a cytostatic agent, cancerostatic agent for inhibition of abnormal cell growth, for anti-proliferative therapy or prevention or as an immunosuppressing agent, optionally in combination with further cytostatic or immunosuppressive active ingredients or other active ingredients suitable for the named indications.

Furthermore, the invention relates to a compound or compound mixture according to formula (I) for use in a therapeutic method in which the therapeutic use is carried out in connection with one or more medical indications with tumors or for immunosuppression, optimally in combination with further pharmaceuticals suitable for the named indications.

The use of one or more compounds according to formula (I), for the production of medicaments for the treatment of the human or animal body, especially in connection with one or more medical indications in the treatment of tumors or for immunosuppression, optimally in combination with further pharmaceuticals suitable in these indications or the use of compounds according to formula (I) in a corresponding diagnosis method also represent an embodiment according to the invention.

The respective suitable tumor indications are illustrated in the last section of the description in the discussion of the pharmacological test results.

A method for the production of medicaments with an amount of one or more compounds according to formula (I) which are suitable for the processing of these active ingredients together with respective suitable pharmaceutically acceptable carriers and adjuvants for finished medicinal forms equally belongs to the scope of protection according to the invention.

Depending on the medical indication being considered, the respective suitable medicinal form is selected for the suitable therapeutic application. In this connection, especially 0.001 to 1000, 2000, 3000, 4000 or 5000 mg, preferably 0.01 to 100 mg, in a preferred manner 1 to 10 mg, especially also 1, 2, 5, 10, 20, 25, 30, 50, 100, 200, 300, 400, 500, 600 or 800 mg single doses are considered as applicable dose units.

The invention also relates to the use of the compounds according to formula (I) for treatment in the above indications, as well as a diagnostic agent.

In the following, the production methods for the respective suitable medicaments as well as a series of examples for medicinal forms and pharmacological activities are described for more easy understanding of the invention. These examples provided in the following as well as the above synthesis examples serve for illustration of the claims without limiting the scope of protection. The skilled person can correspondingly modify the invention within the framework of his abilities without deviating from the scope of protection.

Therapeutic Administration Forms

The production of medicaments with an amount of one or more compounds according to the invention and/or their use in the application according to the invention occurs in the customary manner by means of common pharmaceutical technology methods. For this, the active ingredients as such or in the form of their salts are processed together with suitable, pharmaceutically acceptable adjuvants and carriers to medicinal forms suitable for the various indications and types of application. Thereby, the medicaments can be produced in such a manner that the respective desired release rate is obtained, for example a quick flooding and/or a sustained or depot effect.

Preparations for parenteral use, to which injections and infusions belong, are among the most important systemically employed medicaments for tumor treatment as well as for other indications.

Preferably, injections are administered for the treatment of tumors. These are prepared either in the form of vials or also as so-called ready-to-use injection preparations, for example as ready-to-use syringes or single use syringes in addition to perforation bottles for multiple withdrawals. Administration of the injection preparations can occur in the form of subcutaneous (s.c.), intramuscular (i.m.), intravenous (i.v.) or intracutaneous (i.c.) application. The respective suitable injection forms can especially be produced as solutions, crystal suspensions, nanoparticular or colloid-disperse systems, such as for example, hydrosols.

The injectable formulations can also be produced as concentrates which can be adjusted with aqueous isotonic dilution agents to the desired active ingredient dosage. Furthermore, they can also be produced as powders, such as for example lyophilisates, which are then preferably dissolved or dispersed immediately before application with suitable diluents. The infusions can also be formulated in the form of isotonic solutions, fat emulsions, liposome formulations, microemulsions and liquids based on mixed micells, for example, based on phospholipids. As with injection preparations, infusion formulations can also be prepared in the form of concentrates to dilute. The injectable formulations can also be applied in the form of continuous infusions as in stationary as well as in out-patient therapy, for example in the form of mini-pumps.

Albumin, plasma expanders, surface active compounds, organic solvents, pH influencing compounds, complex forming compounds or polymeric compounds can be added to the parenteral medicinal forms, especially as substances for influencing the adsorption of the active ingredients to protein or polymers or also with the aim of decreasing the adsorption of the active ingredient to materials such as injection instruments or packaging materials, for example plastic or glass.

The active ingredients can be bound to nanoparticles in the preparations for parenteral use, for example on finely dispersed particles based on poly(meth)acrylates, polyacetates, polyglycolates, polyamino acids or polyether urethanes. The parenteral formulations can also be constructively modified as depot preparations, for example on the multiple unit principle, where the active ingredients are incorporated in a most finely distributed and/or dispersed, suspended form or as crystal suspensions, or on the single unit principle, where the active ingredient is enclosed in a medicinal form, for example, a tablet or a seed which is subsequently implanted. Often, these implantations or depot medicaments in single unit and multiple unit medicinal forms consist of so-called biodegradable polymers, such as for example, polyether urethanes of lactic and glycolic acid, polyether urethanes, polyamino acids, poly(meth)acrylates or polysaccharides.

Sterilized water, pH value influencing substances, such as for example organic and inorganic acids or bases as well as their salts, buffer substances for setting the pH value, agents for isotonicity, such as for example sodium chloride, monosodium carbonate, glucose and fructose, tensides and/or surface active substances and emulsifiers, such as for example, partial fatty acid esters of polyoxyethylene sorbitan (Tween®) or for example fatty acid esters of polyoxyethylene (Cremophor®), fatty oils such as for example peanut oil, soybean oil and castor oil, synthetic fatty acid esters, such as for example ethyl oleate, isopropyl myristate and neutral oil (Miglyol®) as well as polymer adjuvants such as for example gelatine, dextran, polyvinylpyrrolidone, organic solvent additives which increase solubility, such as for example propylene glycol, ethanol, N,N-dimethylacetamide, propylene glycol or complex forming compounds such as for example citrates and urea, preservatives, such as for example hydroxypropyl benzoate and hydroxymethyl benzoate, benzyl alcohol, anti-oxidants, such as for example sodium sulphite and stabilizers, such as for example EDTA, are suitable as adjuvants and carriers in the production of preparations for parenteral use.

In suspensions, addition of thickening agents to prevent the settling of the active ingredients from tensides and peptizers, to secure the ability of the sediment to be shaken, or complex formers, such as EDTA, ensues. This can also be achieved with the various polymeric agent complexes, for example with polyethylene glycols, polystyrol, carboxymethylcellulose, Pluronics® or polyethylene glycol sorbitan fatty acid esters. The active ingredient can also be incorporated in liquid formulations in the form of inclusion compounds, for example with cyclodextrins. As further adjuvants, dispersion agents are also suitable. For production of lyophilisates, builders are also used, such as for example mannite, dextran, saccharose, human albumin, lactose, PVP or gelatine varieties.

As long as the active ingredients are not incorporated in the liquid medicinal formulations in the form of a base, they are used in the form of their acid addition salts, hydrates or solvates in the preparations for parenteral use.

A further systemic application form of importance is peroral administration as tablets, hard or soft gelatine capsules, coated tablets, powders, pellets, microcapsules, oblong compressives, granules, chewable tablets, lozenges, gums or sachets. These solid peroral administration forms can also be prepared as sustained action and/or depot systems. Among these are medicaments with an amount of one or more micronized active ingredients, diffusions and erosion forms based on matrices, for example by using fats, wax-like and/or polymeric compounds, or so-called reservoir systems. As a retarding agent and/or agent for controlled release, film or matrix forming substances, such as for example ethylcellulose, hydroxypropylmethylcellulose, poly(meth)acrylate derivatives (for example Eudragit®), hydroxypropylmethylcellulose phthalate are suitable in organic solutions as well as in the form of aqueous dispersions. In this connection, so-called bio-adhesive preparations are also to be named in which the increased retention time in the body is achieved by intensive contact with the mucus membranes of the body. An example of a bio-adhesive polymer is the group of Carbomers®.

For sublingual application, compressives, such as for example non-disintegrating tablets in oblong form of a suitable size with a slow release of active ingredient, are especially suitable. For purposes of a targeted release of active ingredients in the various sections of the gastrointestinal tract, mixtures of pellets which release at the various places are employable, for example mixtures of gastric fluid soluble and small intestine soluble and/or gastric fluid resistant and large intestine soluble pellets. The same goal of releasing at various sections of the gastrointestinal tract can also be conceived by suitably produced laminated tablets with a core, whereby the coating of the agent is quickly released in gastric fluid and the core of the agent is slowly released in the small intestine milieu. The goal of controlled release at various sections of the gastrointestinal tract can also be attained by multilayer tablets. The pellet mixtures with differentially released agent can be filled into hard gelatine capsules.

Anti-stick and lubricant and separating agents, dispersion agents such as flame dispersed silicone dioxide, disintegrates, such as various starch types, PVC, cellulose esters as granulating or retarding agents, such as for example wax-like and/or polymeric compounds on the basis of Eudragit®, cellulose or Cremophor® are used as a further adjuvants for the production of compressives, such as for example tablets or hard and soft gelatine capsules as well as coated tablets and granulates.

Anti-oxidants, sweetening agents, such as for example saccharose, xylite or mannite, masking flavors, aromatics, preservatives, colorants, buffer substances, direct tableting agents, such as for example microcrystalline cellulose, starch and starch hydrolysates (for example Celutab®), lactose, polyethylene glycols, polyvinylpyrrolidone and dicalcium phosphate, lubricants, fillers, such as lactose or starch, binding agents in the form of lactose, starch varieties, such as for example wheat or corn and/or rice starch, cellulose derivatives, for example methylcellulose, hydroxypropylcellulose or silica, talcum powder, stearates, such as for example magnesium stearate, aluminium stearate, calcium stearate, talc, siliconized talc, stearic acid, acetyl alcohol or hydrated fats, etc. are also used.

In this connection, oral therapeutic systems constructed especially on osmotic principles, such as for example GIT (gastrointestinal therapeutic system) or OROS (oral osmotic system), are also to be mentioned.

Effervescent tablets or tabsolute both of which represent immediately drinkable instant medicinal forms which are quickly dissolved or suspended in water are among the perorally administrable compressives.

Among the perorally administrable forms are also solutions, for example drops, juices and suspensions, which can be produced according to the above given method, and can still contain preservatives for increasing stability and optionally aromatics for reasons of easier intake, and colorants for better differentiation as well as antioxidants and/or vitamins and sweeteners such as sugar or artificial sweetening agents. This is also true for inspissated juices which are formulated with water before ingestion. Ion exchange resins in combination with one or more active ingredients are also to be mentioned for the production of liquid injestable forms.

A special release form consists in the preparation of so-called floating medicinal forms, for example based on tablets or pellets which develop gas after contact with body fluids and therefore float on the surface of the gastric fluid. Furthermore, so-called electronically controlled release systems can also be formulated by which active ingredient release can be selectively adjusted to individual needs.

A further group of systemic administration and also optionally topically effective medicinal forms are represented by rectally applicable medicaments. Among these are suppositories and enema formulations. The enema formulations can be prepared based on tablets with aqueous solvents for producing this administration form. Rectal capsules can also be made available based on gelatine or other carriers.

Hardened fat, such as for example Witepsol®, Massa Estarinum®, Novata®, coconut fat, glycerol-gelatine masses, glycerol-soap-gels and polyethylene glycols are suitable as suppository bases.

For long-term application with a systematic active ingredient release up to several weeks, pressed implants are suitable which are preferably formulated on the basis of so-called biodegradable polymers.

As a further important group of systemically active medicaments, transdermal systems are also to be emphasized which distinguish themselves, as with the above-mentioned rectal forms, by circumventing the liver circulation system and/or liver metabolism. These plasters can be especially prepared as transdermal systems which are capable of releasing the active ingredient in a controlled manner over longer or shorter time periods based on different layers and/or mixtures of suitable adjuvants and carriers. Aside from suitable adjuvants and carriers such as solvents and polymeric components, for example based on Eudragit®, membrane infiltration increasing substances and/or permeation promoters, such as for example oleic acid, Azone®, adipinic acid derivatives, ethanol, urea, propylglycol are suitable in the production of transdermal systems of this type for the purpose of improved and/or accelerated penetration.

As topically, locally or regionally administration medicaments, the following are suitable as special formulations: vaginally or genitally applicable emulsions, creams, foam tablets, depot implants, ovular or transurethral administration instillation solutions. For opthalmological application, highly sterile eye ointments, solutions and/or drops or creams and emulsions are suitable.

In the same manner, corresponding otological drops, ointments or creams can be designated for application to the ear. For both of the above-mentioned applications, the administration of semi-solid formulations, such as for example gels based on Carbopols® or other polymer compounds such as for example polyvinylpyrolidone and cellulose derivatives is also possible.

For customary application to the skin or also to the mucus membrane, normal emulsions, gels, ointments, creams or mixed phase and/or amphiphilic emulsion systems (oil/water-water/oil mixed phase) as well as liposomes and transfersomes can be named. Sodium algenate as a gel builder for production of a suitable foundation or cellulose derivatives, such as for example guar or xanthene gum, inorganic gel builders, such as for example aluminium hydroxides or bentonites (so-called thixotropic gel builder), polyacrylic acid derivatives, such as for example Carbopol®, polyvinylpyrolidone, microcrystalline cellulose or carboxymethylcellulose are suitable as adjuvants and/or carriers. Furthermore, amphiphilic low and high molecular weight compounds as well as phospholipids are suitable. The gels can be present either as hydrogels based on water or as hydrophobic organogels, for example based on mixtures of low and high molecular paraffin hydrocarbons and Vaseline.

Anionic, cationic or neutral tensides can be employed as emulsifiers, for example alkalized soaps, methyl soaps, amine soaps, sulfonated compounds, cationic soaps, high fatty alcohols, partial fatty acid esters of sorbitan and polyoxyethylene sorbitan, for example lanette types, wool wax, lanolin, or other synthetic products for the production of oil/water and/or water/oil emulsions.

Hydrophilic organogels can be formulated, for example, on the basis of high molecular polyethylene glycols. These gel-like forms are washable. Vaseline, natural or synthetic waxes, fatty acids, fatty alcohols, fatty acid esters, for example as mono-, di-, or triglycerides, paraffin oil or vegetable oils, hardened castor oil or coconut oil, pig fat, synthetic fats, for example based on acrylic, caprinic, lauric and stearic acid, such as for example Softisan® or triglyceride mixtures such as Miglyol® are employed as lipids in the form of fat and/or oil and/or wax-like components for the production of ointments, creams or emulsions.

Osmotically effective acids and bases, such as for example hydrochloric acid, citric acid, sodium hydroxide solution, potassium hydroxide solution, monosodium carbonate, further buffer systems, such as for example citrate, phosphate, tries-buffer or triethanolamine are used for adjusting the pH value.

Preservatives, for example such as methyl- or propyl benzoate (parabenes) or sorbic acid can be added for increasing stability.

Pastes, powders or solutions are to be mentioned as further topically applicable forms. Pastes often contain lipophilic and hydrophilic auxiliary agents with very high amounts of fatty matter as a consistency-giving base.

Powders or topically applicable powders can contain for example starch varieties such as wheat or rice starch, flame dispersed silicon dioxide or silica, which also serve as diluents, for increasing flowability as well as lubricity as well as for preventing agglomerates.

Nose drops or nose sprays serve as nasal application forms. In this connection, nebulizers or nose creams or ointments can come to use.

Furthermore, nose spray or dry powder formulations as well as controlled dosage aerosols are also suitable for systemic administration of the active ingredients.

These pressure and/or controlled dosage aerosols and dry powder formulations can be inhaled and/or insufflated. Administration forms of this type also certainly have importance for direct, regional application in the lung or bronchi and larynx. Thereby, the dry powder compositions can be formulated for example as active ingredient-soft pellets, as an active ingredient-pellet mixture with suitable carriers, such as for example lactose and/or glucose. For inhalation or insufflation, common applicators are suitable which are suitable for the treatment of the nose, mouth and/or pharynx. The active ingredients can also be applied by means of an ultrasonic nebulizing device. As a propellant gas for aerosol spray formulations and/or controlled dosage aerosols, tetrafluoroethane or HFC 134a and/or heptafluoropropane or HFC 227 are suitable, wherein non-fluorinated hydrocarbons or other propellants which are gaseous at normal pressure and room temperature, such as for example propane, butane or dimethyl ether can be preferred. Instead of controlled dosage aerosols, propellant-free, manual pump systems can also be used.

The propellant gas aerosols can also suitably contain surface active adjuvants, such as for example isopropyl myristate, polyoxyethylene sorbitan fatty acid ester, sorbitan trioleate, lecithins or soya lecithin.

For regional application in situ, solutions for instillation, for example for transurethral administration in bladder tumors or genital tumors, or for profusion in liver tumors or other organ carcinomas are suitable.

The respective suitable medicinal forms can be produced in accordance with the prescription and procedures based on pharmaceutical-physical fundamentals as they are described for example in the following handbooks and are included in the present inventive subject-matter with respect to the production of the respective suitable medicaments:

Physical Pharmacy (A. N. Martin, J. Swarbrick, A. Cammarata), 2nd Ed., Philadelphia Pa., (1970), German version: Physikalische Pharmazie, (1987), 3rd edition, Stuttgart;

R. Voigt, M. Bornschein, Lehrbuch der pharmazeutischen Technologie, Verlag Chemie, Weinheim, (1984), 5th edition;

P. H. List, Arzneiformenlehre, Wissenschaftliche Verlagsgesellschaft mbH, Stuttgart, (1985), 4th edition;

H. Sucker, P. Fuchs, P. Speiser, Pharmazeutische Technologie, Georg Thieme Verlag, Stuttgart—New York, (1991), 2nd edition;

A. T. Florence, D. Attwood, Physicochemical Principles of Pharmacy, The Maximillan Press Ltd., Hong Kong, (1981);

L. A. Trissel, Handbook on Injectable Drugs, American Society of Hospital Pharmacists, (1994), 8th edition;

Y. W. Chien, Transdermal Controlled Systemic Medications, Marcel Dekker Inc., New York—Basel, (1987);

K. E. Avis, L. Lachmann, H. A. Liebermann, Pharmaceutical Dosage Forms: Parenteral Medications, volume 2, Marcel Dekker Inc., New York—Basel, (1986);

B. W. Müller, Controlled Drug Delivery, Paperback APV, volume 17, Wissenschaftliche Verlagsgesellschaft mbH, Stuttgart, (1987);

H. Asch, D. acetic, P. C. Schmidt, Technologie von Salben, Suspensionen and Emulsionen, Wissenschaftliche Verlagsgesellschaft mbH, Stuttgart, (1984);

H. A. Liebermann, L. Lachman, J. B. Schwartz, Pharmaceutical Desage forms: Tablets, Volume 1, Marcel Dekker Inc., New York, 2nd Edition (1989);

D. Chulin, M. Deleuil, Y. Pourcelot, Powder Technology and Pharmaceutical Processes, in J. C. Williams, T. Allen, Handbook of Powder Technology, Elsevier Amsterdam—London—New York—Tokyo, (1994);

J. T. Carstensen, Pharmaceutical Principles of Solid Dosage Forms, Technomic Publishing Co., Inc., Lancaster—Basel, (1993).

PRODUCTION EXAMPLES FOR MEDICAMENTS

1. Injection Therapeutics a) Parenteral Solution

| | |
|---|---|
| active ingredient used according to the invention | 5.000 g |
| acid sodium phosphate | 5.000 g |
| sodium tartrate | 12.000 g |
| benzyl alcohol | 7.500 g |
| water for injection purposes | to 1000.000 ml |

The solution is produced according to the customary method, sterilized and filled into 10 ml vials. One vial contains 50 mg of the compound according to the invention.

b) Parenteral Solution

| | |
|---|---|
| active ingredient used according to the invention | 1.000 g |
| hydrochloric acid, dilute | 5.000 g |
| sodium chloride | 6.000 g |
| water for injection purposes | to 1000.000 ml |

The solution is produced according to a customary method by stirring; the medicinal form is adjusted to a suitable pH value by acid addition and subsequently filled into 100 ml vials and sterilized. A vial contains 100 mg of the compound according to the invention.

c) Parenteral Dispersion

| | |
|---|---|
| active ingredient used according to the invention | 10.000 g |
| soya lecithin | 20.000 g |
| saturated triglycerides | 100.000 g |
| sodium hydroxide | 7.650 g |
| water for injection purposes | to 1000.000 ml |

The active ingredient(s) used according to the invention is dispersed in the saturated triglycerides. Then the soya lecithin is added under stirring, and subsequent to this, the aqueous solution of sodium hydroxide is added with subsequent homogenization. The dispersion is sterilized and filled into 10 ml vials. A vial contains 50 mg of the compound according to the invention.

d) Biodegradable Parenteral Depot Medicinal Form

| | |
|---|---|
| active ingredient used according to the invention | 10.000 g |
| polylactic acid/polygylcolic acid polymer | 70.000 g |
| polyvinylpyrrolidone | 0.200 g |
| gelatine | 2.000 g |
| soya lecithin | 2.000 g |
| isotonic sodium chloride solution | to 1000.000 ml |

First, the active ingredient is incorporated into the biodegradable polymer comprising polylactic acid and polyglycolic acid by a suitable method (spray drying, solvent-evaporation or phase separation) and subsequently subjected to a sterilization process. The particles are introduced into a 2-chamber ready-made syringe in which the adjuvant solution, which is also produced in a sterile manner, is filled. The biodegradable microparticles are mixed with the dispersion agent shortly before application and dispersed. A ready-made syringe contains 200 mg of the active compound according to the invention.

e) Parenteral Dispersion for Subcutaneous Instillation

| | |
|---|---|
| active ingredient used according to the invention | 25,000 g |
| soya lecithin | 25,000 g |
| arachis oil | 400,000 g |
| benzyl alcohol | 50,000 g |
| Miglyole ® | to 1000,000 g |

The active ingredient is dispersed together with soya lecithin and arachis oil. The benzyl alcohol is dissolved in Miglyole® and added to the dispersion. The entire dispersion is sterilized and subsequently filled into vials with 2 ml content. A vial contains 50 mg active ingredient.

f) Parenteral Perfusions Solution

The solution named under example b) can also be used for perfusion of liver for example.

According to need, instead of ampules with injection solution, so-called perforation bottles (vials), which can also be optionally preserved, and infusion solutions with an amount of one or more active ingredients according to the invention can also be made available in the customary manner under addition of buffer substances for adjustment of physiological pH value and/or the isotonicity and/or a best possible suitable pH value for the medicinal form (euhydria) and optional further required nutrients, vitamins, amino acids, stablizers and other necessary adjuvants, possibly in combination with further medicinal agents suitable for the mentioned indications.

2. Solid, Peroral Administrable Medicaments

| a) Tablets | |
|---|---|
| active ingredient used according to the invention | 10.000 g |
| lactose | 5.200 g |
| starch, soluble | 1.800 g |
| hydroxypropylmethylcellulose | 900 g |
| magnesium stearate | 100 g |

The above components are mixed with each other and compacted in a conventional manner, wherein a tablet weight of 180 mg is set. Each tablet contains 100 mg active ingredient. If desired, the tablets obtained in this manner are coated, provided with a film coat and/or enterically coated.

| b) Coated Tablet Core | |
|---|---|
| active ingredient used according to the invention | 10.000 g |
| flame dispersed silicon dioxide | 500 g |
| corn starch | 2.250 g |
| stearic acid | 350 g |
| ethanol | 3.0 l |
| gelatine | 900 g |
| purified water | 10.0 l |
| talcum | 300 g |
| magnesium stearate | 180 g |

From these components, a granulate is produced which is pressed to the desired coated tablet cores. Each core contains 50 mg of active ingredient. The core can be further processed in a customary manner to coated tablets. If desired, a gastric fluid resistant or retarding film coat can be applied in a known manner.

| c) Vials for Drinking | |
|---|---|
| active ingredient used according to the invention | 0.050 g |
| glycerine | 0.500 g |
| sorbite, 70% solution | 0.500 g |
| sodium saccharinate | 0.010 g |
| methyl-p-hydroxybenzoate | 0.040 g |
| aromatic agent | q.s. |
| sterile water | q.s. to 5 ml |

The above-mentioned components are mixed in a customary manner to a suspension and filled in a suitable drink vial having 5 ml content.

| d) Poorly Soluble Sublingual Tablets | |
|---|---|
| active ingredient used according to the invention | 0.030 g |
| lactose | 0.100 g |

-continued

| d) Poorly Soluble Sublingual Tablets | |
|---|---|
| stearic acid | 0.004 g |
| talcum purum | 0.015 g |
| sweetener | q.s. |
| aromatic agent | q.s. |
| rice starch | q.s. to 0.500 g |

The active ingredient is compacted together with the adjuvants under high pressure to sublingual tablets, favourably in oblong form.

| e) Soft Gel Capsule | |
|---|---|
| active ingredient used according to the invention | 0.050 g |
| fatty acid glyceride mixture (Miglyole ®) | q.s. to 0.500 g |

The active ingredient is impasted together with the fluid carrier mixture and mixed together with further adjuvants suitable for the encapsulation and filled into elastic soft gelatine capsules which are sealed.

| f) Hard Gelatine Capsules | |
|---|---|
| active ingredient used according to the invention | 0.150 g |
| microcrystalline cellulose | 0.100 g |
| hydroxypropylmethylcellulose | 0.030 g |
| mannite | 0.100 g |
| ethylcellulose | 0.050 g |
| triethyl citrate | 0.010 g |

The active ingredient is mixed together with the adjuvants, microcrystalline cellulose, hydroxypropylmethylcellulose and mannite, wet with granulation liquid and formed into pellets. These are subsequently coated with a solution of ethylcellulose and triethyl citrate in organic solvents in a fluidized-bed apparatus. A hard gelatine capsule contains 150 mg of active ingredient.

3. Topically Administrable Medicinal Forms

| a) Hydrophilic Ointment | |
|---|---|
| active ingredient used according to the invention | 0.500 g |
| Eucerinum ® anhydricum | 60.000 g |
| microcrystalline wax | 15.000 g |
| Vaseline oil | q.s. to 100.000 g |

The above-mentioned adjuvants are melted and further processed together with the active ingredient to an ointment in a customary manner.

| b) Lipophilic Ointment | |
|---|---|
| active ingredient used according to the invention | 10.000 g |
| propylene glycol | 50.000 g |
| paraffin, liquid | 100.000 g |

-continued

| b) Lipophilic Ointment | |
|---|---|
| paraffin wax | 100.000 g |
| Vaseline | to 1000.000 ml |

The active ingredient(s) used according to the invention is dissolved in propylene glycol at ca. 60° C. At the same time, the lipophilic components are melted at 60–70° C. and subsequently combined with the active ingredient solution. The ointment is emulsified at first at 60–70° C. and subsequently cooled to 35–40° C. under constant emulsification and then filled in 10 g tubes. A tube contains 100 mg of the compound according to the invention.

4. Inhalation Therapeutic Agent

Further subject-matter is a pharmaceutical formulation which is characterized in that it contains an active ingredient(s) used according to the invention as a base or a physiologically acceptable salt thereof together with carriers and/or diluents customary for this and suitable for administration by means of inhalation.

In connection with the production of the medicaments, particularly suitable physiologically acceptable salts of the active ingredients are, as already illustrated in the synthesis section, acid addition salts derived from inorganic or organic acids such as for example especially hydrochloride, hydrobromide, sulfate, phosphate, maleate, tartrate, citrate, benzoate, 4-methoxybenzoate, 2- or 4-hydroxybenzoate, 4-chlorobenzoate, p-tosylate, methane sulfonate, ascorbate, salicylate, acetate, formate, succinate, lactate, glutarate, gluconate or tricarballylate.

The administration of the active ingredients) used of the invention by means of inhalation occurs according to the invention in conventional ways customary for administrations of this form, for example in the form of a commercial controlled dosage aerosol or in combination with a spacer. In controlled dosage aerosols, a metering valve is delivered with whose help, a dosed amount of the composition is administered. For spraying, the present compositions can be formulated for example as aqueous solutions or suspensions and be administered by means of an atomizer. Aerosol spray formulations in which the active ingredient is either suspended with one or two stabilizers in a propellant as a carrier and/or diluent, for example tetrafluoroethane or HFC 134a and/or heptafluoropropane or HFC 227 can equally be used, whereby however, non-fluorinated hydrocarbons or other propellants which are gaseous at normal pressure and room temperature, such as propane, butane or dimethyl ether, can be preferred. Thereby, propellant-free manual pump systems or dry powder systems as described below can also be used.

Suitably, the propellant aerosols can also contain surface active adjuvants, such as for example isopropyl myristate, polyoxyethylene sorbitan fatty acid ester, sorbitan trioleate, lecithins, oleic acid.

For administration by means of inhalation and/or insufflation, the medicaments with an amount of compounds according to the invention can also be formulated in the form of dry powder compositions, for example as active ingredient-soft pellets or as an active ingredient-powder mixture with a suitable carrier, such as for example lactose and/or glucose. The powder compositions can be formulated and administered as single doses or as multiple doses.

The compounds according to the invention are preferably administered by means of a controlled dosage aerosol or in the form of a dry powder dosage formulation, wherein the latter preferably contains glucose and/or lactose as a carrier substance.

As applicators for inhalation of the pharmaceutical formulations containing one or more of the active ingredient(s) used according to the invention, all applicators are generally suitable which are suitable for controlled dosage aerosols and/or a dry powder dosage formulation, such as for example usual applicators for the nose, mouth and or pharynx, or also devices standing under propellant gas for the delivery of a spray (as controlled dosage aerosol or dry powder dosage formulation) as they are also used for inhalations in the nose, mouth and/or pharynx.

A further embodiment can also consist of an aqueous solution of the active ingredient(s) used according to the invention, which also optionally contains further active ingredients and/or additives, which are applied by means of an ultrasound atomizer.

| | Intended dose per stroke | per aerosol % by weight |
|---|---|---|
| a) Controlled Dosage Aerosol | | |
| active ingredient used according to the invention | 0.500 mg | 0.66 |
| stabilizer | 0.075 mg | 0.10 |
| HFC 134a | 75.500 mg | 99.24 |
| b) Controlled Dosage Aerosol | | |
| active ingredient used according to the invention | 0.250 mg | 0.32 |
| Stabilizer | 0.038 mg | 0.05 |
| HFC 227 | 79.180 mg | 99.63 |

In the examples a) and b) the micronized active ingredient is, after previous dispersion in a small amount of the stabilizer, placed in a suspension vessel in which the bulk amount of propellant gas solution is found. The corresponding suspension is dispersed by means of a suitable stirring system (for example high performance mixer or ultrasound mixer) until an ultra-fine dispersion results. The suspension is then continuously held in flux in a filling apparatus suitable for cold propellants or pressure fillings.

Alternatively, the suspension can also be produced in a suitable cooled stabilizer solution in HFC 134a/227.

The examples c) to d) describe the composition and production of dosage dry powder formulations.

| | mg/dose |
|---|---|
| c) Dosage-Dry Powder Formulation | |
| active ingredient used according to the invention | 0.500 mg |
| d) Dosage-Dry Powder Formulation | |
| active ingredient used according to the invention | 0.500 mg |
| lactose Ph.Eur. | to 2.5 mg or to 5.0 mg |
| e) Dosage-Dry Powder Formulation | |
| active ingredient used according to the invention | 0.250 mg |
| lactose Ph.Eur. | to 2.5 mg or to 5.0 mg |

In example c) the active ingredient is formulated after micronization under addition of steam as pellets with an MMAD between 0,1 and 0,3 mm diameter and brought to use in a multi-dose powder applicator.

In the examples d) and e) the active ingredient is micronized, thereafter, bulk material is mixed with the lactose in the given amounts, and subsequently, filled in a multi-dose powder inhalator.

In all of the examples set forth above, the active ingredient or the medicinal agent in the form of the respective suitable pharmaceutical acceptable salt and/or acid addition salts can be present, insofar as the base is not preferred in each case.

Pharmaceutical Experimental Section

1. Growth Inhibition of Human Tumor Cells

The tumor growth inhibiting activity of the substances was determined on human tumor cells in standardized in vitro test systems. In the screening tests, the substances gave $IC_{50}$-values in a concentration range of 0.1 nM to 10 μM.

Example 1

HepG2 cells derived from a human liver carcinoma plated at a density of 20,000 cells/ml in 12-well plastic dishes. Cultivation occurred in Richters IMEM-ZO nutrient medium with 5% foetal calf serum (FCS) in a tissue culture incubator with a gas mixture of 5% $CO_2$ and 95% air at a temperature of 37° C. One day after plating, the culture medium was aspirated from the cells and replaced by fresh medium which contained the respective concentrations of the test substances. For the individual concentrations and the controls without test substances, three-fold batches were done for each. Three days after the beginning of treatment, the medium was again renewed with the test compounds. After six days of substance incubation, the test was ended and the protein amount in the individual wells was determined with the sulforhodamin-B-method (according to P. Skehan et al.: New Colorimetric Cytotoxicity Assay for Anticancer-Drug Screening. J. Natl. Cancer Inst. 82: 1107–1112, 1990). The $IC_{50}$-values (defined as that concentration in which the cell growth was inhibited by 50%) was taken from the dose-response curves and given as a comparative measurement for the activity of the test compounds.

The following results were obtained:

| Test substance No. | $IC_{50}$-value [μM] |
| --- | --- |
| 12 | 0.5 |
| 28 | 0.2 |
| 38 | 0.6 |
| 43 | 0.0002 |
| 92 | 0.04 |
| 189 | 0.8 |
| 196 | 10 |
| 278 | 0.3 |

Example 2

A549 cells derived from a human lung carcinoma plated at a density of 20,000 cells/ml in 12-well plastic dishes. Cultivation occurred in Richters IMEM-ZO nutrient medium with 5% foetal calf serum (FCS) in a tissue culture incubator with a gas mixture Of 5% $CO_2$ and 95% air at a temperature of 37° C. One day after plating, the culture medium was aspirated from the cells and replaced by fresh medium which contained the respective concentrations of the test substances. For the individual concentrations and the controls without test substances, three-fold batches were done for each. Three days after the beginning of treatment, the medium was again renewed with the test compounds. After four days of substance incubation, the test was ended and the protein amount in the individual wells was determined with the sulforhodamin-B-method (according to P. Skehan et al.: New Colorimetric Cytotoxicity Assay for Anticancer-Drug Screening. J. Natl. Cancer Inst. 82: 1107–1112, 1990). The $IC_{50}$-values (defined as that concentration in which the cell growth was inhibited by 50%) was taken from the dose-response curves and given as a comparative measurement for the activity of the test compounds.

The following results were obtained:

| Test substance No. | $IC_{50}$-value [μM] |
| --- | --- |
| 16 | 2 |
| 40 | 0.003 |
| 43 | 0.0003 |
| 58 | 0.04 |
| 88 | 0.2 |
| 119 | 2 |
| 145 | 0.2 |
| 204 | 0.03 |
| 226 | 0.7 |

Example 3

HT-29 cells derived from a human colon carcinoma plated at a density of 20,000 cells/ml in 12-well plastic dishes. Cultivation occurred in Richters IMEM-ZO nutrient medium with 5% foetal calf serum (FCS) in a tissue culture incubator with a gas mixture of 5% $CO_2$ and 95% air at a temperature of 37° C. One day after plating, the culture medium was aspirated from the cells and replaced by fresh medium which contained the respective concentrations of the test substances. For the individual concentrations and the controls without test substances, three-fold batches were done for each. Three days after the beginning of treatment, the medium was again renewed with the test compounds. After four days of substance incubation, the test was ended and the protein amount in the individual wells was determined with the sulforhodamin-B-method (according to P. Skehan et al.: New Colorimetric Cytotoxicity Assay for Anticancer-Drug Screening. J. Natl. Cancer Inst. 82: 1107–1112, 1990). The $IC_{50}$-values (defined as that concentration in which the cell growth was inhibited by 50%) was taken from the dose-response curves and given as a comparative measurement for the activity of the test compounds as follows:

| Test substance No. | $IC_{50}$-value [μM] |
| --- | --- |
| 195 | 0.005 |

Example 4

THP-1 cells derived from a human monocytic leukemia plated at a density of 200,000 cells/ml in 96-well plastic dishes. Cultivation occurred in RPMI 1640 nutrient medium with 10% foetal calf serum (FCS) in a tissue culture incubator with a gas mixture of 5% $CO_2$ and 95% air at a temperature of 37° C. For the individual concentrations and the controls without test substances as well as for the background with nutrient medium but without cells, threefold batches were done for each. After four days of substance incubation 20 μl WST-1 reagent (Boehringer Mannheim) was respectfully pipetted in each individual well. After 30 to 60 minute incubation in the tissue culture incubator at 37° C. and 5 $CO_2$, the light extinction was measured in an ELISA reader at 450 nm wave length. The backgrounds were each subtracted from the typical measured valves. (The $IC_{50}$-values (defined as that concentration in which the cell growth was inhibited by 50%) was taken from the dose-response curves and given as a comparative measurement for the activity of the test compounds.

The following results were obtained:

| Test substance No. | $IC_{50}$-value [μM] |
|---|---|
| 23 | 0.004 |
| 43 | 0.0002 |
| 195 | 0.001 |
| 204 | 0.005 |

2. Indications

The compounds of formula (I) and their salts permit a therapeutic use in malignant illnesses of humans and animals through their excellent inhibition of the growth of tumor cells. The anti-neoplastic activity of the described substances can be used for prophylactic, adjunct, palliative, and curative treatment of solid tumors, leukemic illnesses and lymphomas as well as for decreasing or preventing metastasis formation in humans and animals. The therapeutic use is possible in the following illnesses for example: gynaecological tumors, ovarian carcinomas, testicle tumors, prostate carcinomas, skin cancer, kidney cancer, bladder tumors, oesophagus carcinomas, stomach cancer, rectal carcinomas, pancreas carcinomas, thyroid cancer, adrenal tumors, leukemia and lymphomas, Hodgkin's disease, tumor illnesses of the CNS, soft-tissue sarcomas, bone sarcomas, benign and malignant mesotheliomas, but especially intestine cancer, liver cancer, breast cancer, bronchial and lung carcinomas, melanomas, acute and chronic leukemias. Benign papillomatosis tumors can also be limited in their growth with the named substances. The broad effectiveness of the new compounds were tested for example in very different human tumor cells in vitro according to the methods described in point 1. Thereby, the following $IC_{50}$ valves were obtained for the compound Nr. 195 for example:

| Cell line | Source | $IC_{50}$-values [mM] |
|---|---|---|
| HT-29 | colon carcinoma | 0.005 |
| A549 | lung carcinoma | 0.008 |
| HepG2 | hepatocelluar carcinoma | 0.04 |
| THP-1 | monocytic leukemia | 0.001 |

The novelty of the compounds can be expected to have an independent activity profile in the effectiveness against the various tumor types. Thus, tumors which are resistant to customary cytostatic agents, for example, can respond entirely to these substances. In addition, based on the independent characteristics, combinations of the new compounds with known pharmaceuticals used in chemotherapy are promising as long as their properties are complimented in a suitable manner. The integration of the new structures in a therapy scheme could be successful with one or more substances from the following classes for example: antimetabolites (for example cytarabine, 5-fluorouracil, 6-mercaptopurine, methotrexate), alkylating agents (for example busulfane, carmustine, cisplatin, carboplatin, cyclophosphamide, dacarbazine, melphalane, thiotepa), DNA-intercalating substances and topoisomerase inhibitors (for example actinomycin D, daunorubicin, doxorubicin, mitomycin C, mitoxantrone, etoposide, teniposide, topotecane, irinotecane), spindle poisons (for example vincristine, navelbine, taxol, taxoter), hormonally active agents (for example tamoxifene, flutamide, formestane, gosereline) or other cytostatic agents with complex modes of action (for example L-asparaginase, bleomycin, hydroxyurea). Resistant tumor cells can be made sensitive again for example by interaction of the new compounds with a mechanism of resistance for common cytostatic agents (for example P-glycoprotein, MRP, glutathione-S-transferase, metallothionein).

3. Immuno Suppressing Activity

Many anti-tumor agents have not only a cytotoxic effect on tumor cells, but also on the blood cell system. This leads to a weakening of the immune defence, which can, in turn, be specifically employed to suppress the rejection reaction after an organ transplantation for example. Also use of the main compounds, optionally in combination with other immunological diseases (for example, psoriasis or autoimmune diseases) seems likely. In order to test the possibility for a therapeutic use in illnesses of this type, the substance activity was tested on freshly isolated lymphocytes as follows:

The spleen of a Swiss mouse served as a lymphocyte source. The lymphocyte population was isolated from the spleen cell suspension over a ficoll gradient and taken up in IMEM-ZO culture medium with 0.1% dextran 70,000 and 2% foetal calf serum. The cells were plated at a density of ca. 500,000 cells/well/ml in a 12-well plate, 1 ml doubly concentrated test substance solution was pipetted per well and this was subsequently incubated in a tissue culture incubator at 37° C. and 5% $CO_2$. After 2 days, a 1 ml-aliquot with 5 μl of the fluorescent dye solutions propidium iodide (8 mg/ml) and 3,3'-dihexyloxacarbocyanin iodide (40 μg/ml) each was added per well, and incubated for 3 minutes at room temperature. Subsequently, 10,000 cells per each sample were measured on a flow-through cytometer and the percentage amount of vital cells in the population was determined. By means of the dose-response curves, $IC_{50}$-values were calculated which were also employed in the following Tables for the characterization of the individual substances:

| Test Substance No. | $IC_{50}$ value [μM] |
|---|---|
| 12 | 0.06 |
| 23 | 0.04 |
| 40 | 0.0006 |
| 43 | 0.0003 |
| 88 | 0.09 |
| 92 | 0.08 |
| 119 | 1 |
| 195 | 0.001 |

The independent structural class of the compounds can also be expected to be successful for an efficient combination with known immunosuppressive agents such as for example cyclosporin A, tacrolimus, rapamycin, azathioprine and glucocorticoids.

The invention claimed is:

1. An imide-substituted pyridylalkane, alkene and alkine acid amide of formula (I)

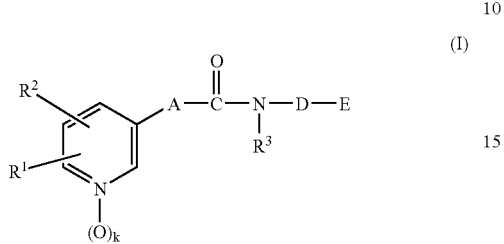

wherein the substituents have the following meanings:

$R^1$ is selected from
hydrogen, halogen, cyano, alkyl, alkenyl, alkinyl, trifluoromethyl, cycloalkyl, hydroxyalkyl, hydroxy, alkoxy, cycloalkyloxy, aralkyloxy, alkanoyloxy, alkylthio, alkoxycarbonyl, aminocarbonyl, alkylaminocarbonyl, dialkylaminocarbonyl, carboxy, aryl, aryloxy, arylthio, heteroaryloxy, heteroarylthio, and $NR^4R^5$, whereby $R^4$ and $R^5$ are selected independently from each other from hydrogen, alkyl, alkenyl, alkinyl, aralkyl and aryl;

$R^2$ is selected from
hydrogen, halogen, cyano, alkyl, trifluoromethyl, hydroxy, alkoxy and aralkyloxy;

$R^3$ is selected from
hydrogen, alkyl, alkenyl, alkinyl, hydroxy, alkoxy and aryloxy;

k is 0 or 1,

A is selected from
alkylene, optionally substituted one to three-fold by alkyl, hydroxy, alkoxy, fluorine, or aryl,
alkylene, wherein a methylene unit is isosterically replaced by O, S, $NR^6$, CO, SO or $SO_2$, whereby, with the exception of CO, the isosteric substitution cannot be adjacent to the amine group and $R^6$ is selected from hydrogen, alkyl, alkenyl, acyl and alkanesulfonyl;
1,2-cyclopropylene;
alkenylene, optionally substituted once or twice by alkyl, hydroxy, alkoxy, fluorine, cyano or aryl;
alkadienylene, optionally substituted once or twice by alkyl, fluorine, cyano or aryl;
hexatrienylene, optionally substituted by $C_1$–$C_3$-alkyl, fluorine, cyano or phenyl; and
ethinylene;

D is selected from
alkylene, optionally substituted once or twice by alkyl, hydroxy, or alkoxy;
alkenylene, optionally substituted once or twice by alkyl, hydroxy, or alkoxy;
alkinylene, optionally substituted once or twice by alkyl, hydroxy, or alkoxy; and
alkylene, alkenylene or alkinylene, in which one to three methylene units is isosterically replaced by O, S, $NR^7$, CO, SO or $SO_2$, wherein $R^7$ is synonymous with $R^6$, but is selected independently thereof;

E is a cyclic imide of the formula

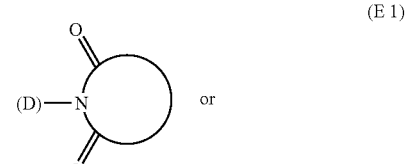

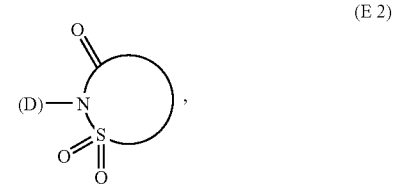

bound over the imide nitrogen atom to D selected from
saturated or unsaturated monocyclic imides with 5 to 7 ring atoms, whereby, aside from the essential imide nitrogen atom, one or two further hetero-atoms can be present selected from N and/or S and/or O in this imide ring;
saturated, unsaturated or aromatic anellated bi-, tri- or tetracyclic imides with 8 to 18 ring atoms of which, aside from the essential imide nitrogen atom, one to three further hetero-atoms can be present selected from N and/or S and/or O;
saturated or unsaturated, bridged bi-, tri- tetra- or pentacyclic imides with 8 to 22 ring atoms of which, aside from the essential imide nitrogen atom, one to three further hetero-atoms can be present selected from N and/or S and/or O;
saturated or unsaturated spirocyclic imides, optionally anellated once or twice and with a total of 9 to 23 ring atoms of which, aside from the essential imide nitrogen atom, one to three further hetero-atoms can be present selected from N and/or S and/or O;
whereby these cyclic imides can be substituted by one to five of the same or different groups selected independently from each other from
halogen, cyano, alkyl, alkylidene, trifluoromethyl, cycloalkyl, cycloalkylidene, phenylalkyl, phenylalkylidene, diphenylalkyl, diphenylalkylidene, triphenylmethyl, aryl, hydroxy, hydroxyalkyl, alkoxy, alkoxy entirely or partially substituted by fluorine, aralkyloxy, aryloxy, naphthyloxy, mercapto, alkylthio, arylthio, heteroarylthio, alkanesulfonyl, arylsulfonyl, heteroarylsulfonyl, sulfo, carboxy, carboxyalkyl, carboxyalkenyl, alkoxycarbonyl, aralkyloxycarbonyl, nitro, amino, aminoalkyl, mono-alkylamino, di-(alkyl)amino, arylamino, arylalkylamino, heteroarylamino,
saturated or unsaturated, four- to seven-membered heterocycles which can contain one or two hetero-atoms selected from N and/or S and/or O and are either bound directly or bound over a methylene group or a methine group,
monocyclic aromatic five- or six-membered heterocycles which can contain one to three hetero-atoms selected from N and/or S and/or O and are either bound directly or bound over a methylene group or a methine group,
anellated bicyclic, aromatic or partially hydrogenated carbocyclic ring systems with 8 to 12 ring atoms which are either bound directly or bound over a methylene or a methine group, anellated bicyclic aromatic or partially hydrogenated heterocyclic ring systems with 8 to 12 ring atoms, whereby one to three ring atoms can be selected from N and/or S and/or O and are either bound directly or bound over a methylene or a methine group, and whereby aryl and heteroaryl residues as substituents of the cyclic imides can be substituted themselves by one to three of the same or different groups selected from halogen, cyano, alkyl, trifluoromethyl, cycloalkyl, aralkyl, aryl, hydroxy, hydroxyalkyl, alkoxy, alkoxy entirely or partially substituted by fluorine, aralkyloxy, aryloxy, mercapto, alkylthio, arylthio, carboxy, carboxyalkyl, carboxyalkenyl, alkoxycarbonyl, aralkyloxycarbonyl, nitro, amino, aminoalkyl, mono-alkylamino, di-(alkyl)amino and, for two adjacent residues, methylenedioxy;

the cis- and trans-isomer, E- and Z-isomer of the above defined compound, the enantiomer, diastereomer and other isomer of the above defined compound, and their racemic and/or non-racemic mixtures, and the pure endo- and/or exo-isomers of the above defined compound in the case that the imide ring system is bicyclic, and their mixture;

the tautomeric compound in the optional case that E contains a heterocyclic aromatic ring with simultaneous substitution by free hydroxy, mercapto or amino groups; or the acid addition salt, hydrate or solvate of the above defined compound.

2. An imide-substituted pyridylalkane, pyridylalkene and pyridylalkine acid amide of formula (I)

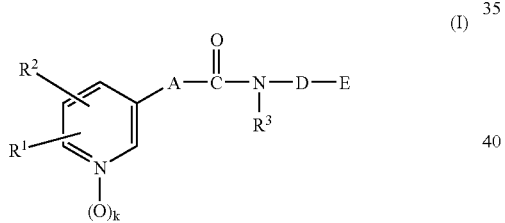
(I)

wherein the substituents have the following meanings:

$R^1$ is selected from hydrogen, halogen, cyano, $C_1$–$C_6$-alkyl, $C_3$–$C_6$-alkenyl, $C_2$–$C_6$-alkinyl, trifluoromethyl, $C_3$–$C_8$-cycloalkyl, $C_1$–$C_6$-hydroxyalkyl, hydroxy, $C_1$–$C_6$-alkoxy, $C_3$–$C_8$-cycloalkyloxy, benzyloxy, $C_1$–$C_7$-alkanoyloxy, $C_1$–$C_6$-alkylthio, $C_2$–$C_7$-alkoxycarbonyl, aminocarbonyl, $C_2$–$C_7$-alkylaminocarbonyl, $C_3$–$C_{13}$-dialkylaminocarbonyl, carboxy, phenyl, phenoxy, phenylthio, pyridyloxy, pyridylthio, and $NR^4R^5$, whereby $R^4$ and $R^5$ are selected independently from each other from hydrogen, $C_1$–$C_6$-alkyl, $C_3$–$C_6$-alkenyl, $C_3$–$C_6$-alkinyl, benzyl and phenyl;

$R^2$ is selected from hydrogen, halogen, cyano, $C_1$–$C_6$-alkyl, trifluoromethyl, hydroxy, $C_1$–$C_6$-alkoxy and benzyloxy;

$R^3$ is selected from hydrogen, $C_1$–$C_6$-alkyl, $C_3$–$C_6$-alkenyl, $C_3$–$C_6$-alkinyl, hydroxy, $C_1$–$C_6$-alkoxy and benzyloxy;

k is 0 or 1,

A is selected from $C_1$–$C_6$-alkylene, optionally substituted one to threefold by $C_1$–$C_3$-alkyl, hydroxy, $C_1$–$C_3$-alkoxy, fluorine, or phenyl;

$C_2$–$C_6$-alkylene, in which a methylene unit is isosterically replaced by O, S, $NR^6$, CO, SO or $SO_2$, whereby, with the exception of CO, the isosteric substitution cannot be adjacent to the amide group and $R^6$ is selected from hydrogen, $C_1$–$C_6$-alkyl, $C_3$–$C_6$-alkenyl, $C_1$–$C_6$-acyl or $C_1$–$C_6$-alkanesulfonyl;

1,2-cyclopropylene;

$C_2$–$C_6$-alkenylene, optionally substituted once or twice by $C_1$–$C_3$-alkyl, hydroxy, $C_1$–$C_3$-alkoxy, fluorine, cyano or phenyl;

$C_4$–$C_6$-alkadienylene, optionally substituted once to twice by $C_1$–$C_3$-alkyl, fluorine, cyano or phenyl;

1,3,5-hexatrienylene, optionally substituted by $C_1$–$C_3$-alkyl, fluorine, cyano or phenyl; and ethinylene;

D is selected from $C_2$–$C_{10}$-alkylene, optionally substituted once or twice by $C_1$–$C_6$-alkyl, hydroxy, or $C_1$–$C_6$-alkoxy;

$C_4$–$C_{10}$-alkenylene, optionally substituted once or twice by $C_1$–$C_6$-alkyl, hydroxy, or $C_1$–$C_6$-alkoxy;

$C_4$–$C_{10}$-alkinylene, optionally substituted once or twice by $C_1$–$C_6$-alkyl, hydroxy, or $C_1$–$C_6$-alkoxy; and $C_2$–$C_{10}$-alkylene, $C_4$–$C_{10}$-alkenylene or $C_4$–$C_{10}$-alkinylene, in which one to three methylene units is isosterically replaced by O, S, $NR^7$, CO, SO or $SO_2$, whereby $R^7$ is synonymous with $R^6$, but is selected independently thereof;

E is a cyclic imide of the formula

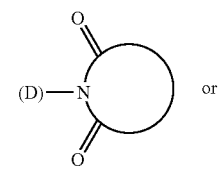
(E 1)

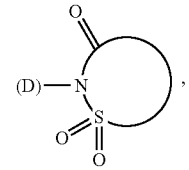
(E 2)

bound over the imide nitrogen atom to D selected from saturated or unsaturated monocyclic imides with 5 to 7 ring atoms of which, aside from the essential imide nitrogen atom, one or two further hetero-atoms can be present selected from N and/or S and/or O;

saturated, unsaturated or aromatic anellated, bi-, tri- or tetracyclic imides with 8 to 18 ring atoms of which, aside from the essential imide nitrogen atom, one to three further hetero-atoms can be present selected from N and/or S and/or O;

saturated or unsaturated, bridged bi-, tri- tetra- or pentacyclic imides with 8 to 22 ring atoms of which, aside from the essential imide nitrogen atom, one to three further hetero-atoms can be present selected from N and/or S and/or O;

saturated or unsaturated spirocyclic imides, optionally anellated once or twice and with a total of 9 to 23 ring atoms of which, aside from the essential imide nitrogen atom, one to three further hetero-atoms can be present selected from N and/or S and/or O;

whereby these cyclic imides can be substituted by one to five of the same or different groups selected independently from each other from halogen, cyano, $C_1$–$C_6$-alkyl, $C_1$–$C_6$-alkylidene, trifluoromethyl, $C_3$–$C_8$-cycloalkyl, $C_3$–$C_8$-cycloalkylidene, phenyl-$C_1$–$C_3$-alkyl, phenyl-$C_1$–$C_3$-alkylidene, diphenyl-$C_1$–$C_3$-alkyl, diphenyl-$C_1$–$C_3$-alkylidene, triphenylmethyl, phenyl, hydroxy, $C_1$–$C_6$-hydroxyalkyl, $C_1$–$C_6$-alkoxy, $C_1$–$C_6$-alkoxy entirely or partially substituted by fluorine, benzyloxy, phenoxy, naphthyloxy, mercapto, $C_1$–$C_6$-alkylthio, phenylthio, naphthylthio, pyridylthio, $C_1$–$C_6$-alkanesulfonyl, phenylsulfonyl, naphthylsulfonyl, pyridylsulfonyl, sulfo, carboxy, $C_2$–$C_7$-carboxyalkyl, $C_2$–$C_7$-carboxyalkenyl, $C_2$–$C_7$-alkoxycarbonyl, benzyloxycarbonyl, nitro, amino, $C_1$–$C_6$-aminoalkyl, mono-$C_1$–$C_6$-alkylamino, di-($C_1$–$C_6$-alkyl)amino, phenylamino, phenyl-$C_1$–$C_3$-alkylamino, pyridylamino, saturated or unsaturated, four- to seven-membered heterocycles which can contain one or two hetero-atoms selected from N and/or S and/or O and are either bound directly or bound over a methylene group or a methine group, monocyclic aromatic five- or six-membered heterocycles which can contain one to three hetero-atoms selected from N and/or S and/or O and are either bound directly or bound over a methylene group or a methine group, anellated bicyclic, aromatic or partial hydrogenated carbocyclic ring systems with 8 to 12 ring atoms which are either bound directly or bound over a methylene or a methine group, anellated bicyclic aromatic or partially hydrogenated heterocyclic ring systems with 8 to 12 ring atoms, whereby one to three ring atoms can be selected from N and/or S and/or O and are either bound directly or bound over a methylene or a methine group, and whereby aryl and heteroaryl residues as substituents of the cyclic imides can be substituted themselves by one to three of the same or different groups selected from halogen, cyano, $C_1$–$C_6$-alkyl, trifluoromethyl, $C_3$–$C_8$-cycloalkyl, benzyl, phenyl, hydroxy, $C_1$–$C_6$-hydroxyalkyl, $C_1$–$C_6$-alkoxy, $C_1$–$C_6$-alkoxy entirely or partially substituted by fluorine, benzyloxy, phenoxy, mercapto, $C_1$–$C_6$-alkylthio, phenylthio, carboxy, $C_2$–$C_7$-carboxyalkyl, $C_2$–$C_7$-carboxyalkenyl, $C_2$–$C_7$-alkoxycarbonyl, benzyloxycarbonyl, nitro, amino, $C_1$–$C_6$-aminoalkyl, mono-$C_1$–$C_6$-alkylamino, di-($C_1$–$C_6$-alkyl)amino and, for two adjacent residues, methylenedioxy;

the cis- and trans-isomer, E- and Z-isomer of the above defined compound, the enantiomer, diastereomer and other isomer of the above defined compound, and the racemic and/or non-racemic mixture, and the pure endo- and/or exo-isomers of the above defined compound in the case that the imide ring system is bicyclic, and the mixture;

the tautomeric compound in the optional case that E contains a heterocyclic aromatic ring with simultaneous substitution by free hydroxy, mercapto or amino groups; or a acid addition salt, hydrate or solvates of the above defined compounds.

3. The compound according to claim 1 or 2, wherein the substituents have the following meanings:

$R^1$ is selected from
hydrogen, halogen, cyano, $C_1$–$C_6$-alkyl, trifluoromethyl, ethinyl, hydroxy, $C_1$–$C_4$-alkoxy, benzyloxy, $C_1$–$C_4$-alkylthio, $C_2$–$C_5$-alkoxycarbonyl, aminocarbonyl, $C_3$–$C_9$-dialkyl-aminocarbonyl, carboxy, phenoxy, phenylthio and pyridyloxy;

$R^2$ is selected from
hydrogen, fluorine, chlorine, bromine, $C_1$–$C_4$-alkyl, trifluoromethyl, hydroxy, $C_1$–$C_4$-alkoxy;

$R^3$ is selected from
hydrogen, $C_1$–$C_3$-alkyl, allyl, hydroxy, $C_1$–$C_3$-alkoxy and benzyloxy;

k is 0 or 1,

A is selected from
$C_1$–$C_6$-alkylene, optionally substituted once or twice by $C_1$–$C_3$-alkyl, hydroxy, fluorine or phenyl;
$C_2$–$C_6$-alkylene, wherein a methylene unit is isosterically replaced by O, S, NH, N(CH$_3$) or CO, whereby, with the exception of CO, the isosteric substitution cannot be adjacent to the amide group; and
1,2-cyclopropylene;
$C_2$–$C_6$-alkenylene, optionally substituted once or twice by $C_1$–$C_3$-alkyl, phenyl, hydroxy and/or fluorine;
$C_4$–$C_6$-alkadienylene, optionally substituted once to twice by methyl or fluorine;
1,3,5-hexatrienylene, optionally substituted by methyl or fluorine; and
ethinylene D is selected from
$C_2$–$C_8$-alkylene, optionally substituted once or twice by $C_1$–$C_3$-alkyl or hydroxy;
$C_4$–$C_8$-alkenylene, optionally substituted once or twice by $C_1$–$C_3$-alkyl or hydroxy;
$C_4$–$C_8$-alkinylene, optionally substituted once or twice by $C_1$–$C_3$-alkyl or hydroxy; and
$C_2$–$C_8$-alkylene, $C_4$–$C_8$-alkenylene or $C_4$–$C_8$-alkinylene, wherein one to three methylene units are isosterically replaced by O, S, NH, N(CH$_3$), N(COCH$_3$), N(SO$_2$CH$_3$), CO or SO$_2$;

E is selected from saturated or unsaturated monocyclic imides with 5 to 7 ring atoms,
saturated, unsaturated or aromatic anellated bicyclic imides,
unsaturated or aromatic anellated tricyclic imides
unsaturated or aromatic anellated tetracyclic imides,
saturated or unsaturated, bridged bi-, tri-, tetra- or pentacyclic imides, and
saturated or unsaturated spirocyclic imides which are optionally benzoanellated once or twice,
whereby these cyclic imides can be substituted by one to five of the same or different groups selected independently from each other from halogen, cyano, $C_1$–$C_4$-alkyl, $C_1$–$C_4$-alkylidene, trifluoromethyl, $C_3$–$C_8$-cycloalkyl, phenyl-$C_1$–$C_3$-alkyl, phenyl-$C_1$–$C_3$-alkylidene, diphenyl-$C_1$–$C_3$-alkyl, diphenyl-$C_1$–$C_3$-alkylidene, triphenylmethyl, phenyl, hydroxy, $C_1$–$C_4$-hydroxyalkyl, $C_1$–$C_4$-alkoxy, $C_1$–$C_4$-alkoxy entirely or partially substituted by fluorine, benzyloxy, phenoxy, naphthyloxy, mercapto, $C_1$–$C_4$-alkylthio, phenylthio, pyridylthio, $C_1$–$C_4$-alkanesulfonyl, phenylsulfonyl, naphthylsulfonyl, pyridylsulfonyl, sulfo, carboxy, $C_2$–$C_7$-carboxyalkyl, $C_2$–$C_7$-carboxyalkenyl, $C_2$–$C_7$-alkoxycarbonyl, benzyloxycarbonyl, nitro, amino, $C_1$–$C_4$-aminoalkyl, mono-$C_1$–$C_4$-alkylamino, di-($C_1$–$C_4$-alkyl)amino, phenylamino, phenyl-$C_1$–$C_3$-alkylamino, pyridylamino, saturated or unsaturated, four- to seven-membered heterocycles which can contain one or two hetero-atoms selected from N and/or S and/or O, monocyclic aromatic five- or six-membered heterocycles, which can contain one to three hetero-atoms selected from N and/or S and/or O and are either bound directly or bound over a methylene group or a methine group, anellated bicyclic, aromatic or partially hydrogenated carbocyclic ring systems with 8 to 11 ring atoms which are either bound directly or bound over a methylene group or a methine group, anellated bicyclic aromatic or partially hydrogenated heterocyclic rings systems with 8 to 11 rings atoms, whereby one to three ring atoms can be selected from N and/or S and/or O and are either bound directly or bound over a methylene group or a methine group, and whereby aryl and heteroaryl residues as substituents of the cyclic imides can be substituted themselves by one to three of the same or different groups selected from halogen, cyano, $C_1$–$C_6$-alkyl, trifluoromethyl, $C_3$–$C_8$-cycloalkyl, benzyl, phenyl, hydroxy, $C_1$–$C_6$-hydroxyalkyl, $C_1$–$C_6$-alkoxy, $C_1$–$C_6$-alkoxy entirely or partially substituted by fluorine, benzyloxy, phenoxy, mercapto, $C_1$–$C_6$-alkylthio, phenylthio, carboxy, $C_2$–$C_7$-carboxyalkyl, $C_2$–$C_7$-carboxyalkenyl, $C_2$–$C_7$-alkoxycarbonyl, benzyloxycarbonyl, nitro, amino, $C_1$–$C_6$-aminoalkyl, mono-$C_1$–$C_6$-alkylamino, di-($C_1$–$C_6$-alkyl)amino and, for two adjacent residues, methylenedioxy.

4. The compound according to claim 1 or 2, wherein the substituents have the following meanings:

$R^1$ is selected from
hydrogen, fluorine, chlorine, bromine, methyl, ethyl, trifluoromethyl, hydroxy, $C_1$–$C_4$-alkoxy, phenoxy, methylthio, ethylthio, methoxycarbonyl, aminocarbonyl and carboxy;

$R^2$ is selected from
hydrogen, chlorine, methyl, hydroxy and methoxy;

$R^3$ is hydrogen;

k is 0,

A is selected from
$C_2$–$C_6$-alkylene, optionally substituted once or twice by hydroxy or fluorine;

$C_2$–$C_6$-alkylene, in which a methylene unit is isosterically replaced by O, S, or CO, whereby, with the exception of CO, the isosteric substitution cannot be adjacent to the amide group;

$C_2$–$C_6$-alkenylene, optionally substituted by methyl and/or fluorine;

$C_4$–$C_6$-alkadienylene, optionally substituted by methyl; ethinylene;

D is selected from
$C_2$–$C_8$-alkylene, optionally substituted by methyl or hydroxy;

$C_4$–$C_8$-alkenylene, optionally substituted by methyl or hydroxy;

$C_4$–$C_8$-alkinylene, optionally substituted by hydroxy;

$C_2$–$C_8$-alkylene, $C_4$–$C_8$-alkenylene or $C_4$–$C_8$-alkinylene, in which a methylene unit is isosterically replaced by O, NH, N($CH_3$), or CO, or an ethylene group is isosterically replaced by a group NH—CO and/or CO—NH, or a propylene group is isosterically replaced by a group NH—CO—NH or NH—CO—O and/or O—CO—NH;

E is selected from
monocyclic imides, anellated bicyclic imides, anellated tricyclic imides, anellated tetracyclic imides, bridged polycyclic imides and spirocyclic imides, whereby these cyclic imides can be substituted by one to five of the same or different groups selected independently from each other from halogen, cyano, $C_1$–$C_4$-alkyl, trifluoromethyl, $C_3$–$C_8$-cycloalkyl, hydroxy, $C_1$–$C_4$-hydroxyalkyl, $C_1$–$C_4$-alkoxy, $C_1$–$C_4$-alkoxy entirely or partially substituted by fluorine, benzyloxy, phenoxy, naphthyloxy, $C_1$–$C_4$-alkylthio, phenylthio, pyridylthio, $C_1$–$C_4$-alkanesulfonyl, phenylsulfonyl, naphthylsulfonyl, pyridylsulfonyl, sulfo, carboxy, $C_2$–$C_7$-carboxyalkyl, $C_2$–$C_7$-carboxyalkenyl, $C_2$–$C_7$-alkoxycarbonyl, benzyloxycarbonyl, nitro, amino, $C_1$–$C_4$-aminoalkyl, di-($C_1$–$C_4$-alkyl)amino, phenylamino, pyridylamino;

benzyl, benzylidene, phenylethyl, phenylethylidene, phenylpropyl, diphenylmethyl, diphenylmethylene, diphenylethyl, triphenylmethyl;

phenyl, indanyl, indenyl, indenylmethyl, naphthyl, naphthyl-methyl, tetrahydronaphthyl, benzocycloheptenyl, tetrahydrobenzocycloheptenyl;

pyrrolidinyl, piperidinyl, morpholinyl, thiomorpholinyl, piperazinyl, hexahydroazepinyl, hexahydrodiazepinyl;

furyl, furylmethyl, thienyl, thienylmethyl, oxazolyl, isoxazolyl, thiazolyl, thiazolylmethyl, imidazolyl, oxadiazolyl, pyridyl, pyridylmethyl, pyrazinyl, pyrimidinyl;

benzofuryl, benzofurylmethyl, benzothienyl, benzothienylmethyl, indolyl, indolylmethyl, indolinyl, oxoindolinyl, dioxoindolinyl, benzooxazolyl, oxobenzooxazolinyl, benzothiazolyl, benzothiazolylmethyl, oxobenzothiazolinyl, benzoimidazolyl, benzoimidazolylmethyl, oxobenzoimidazolinyl, indazolyl, oxoindazolinyl, benzotriazolyl, oxazolopyridyl, oxazolopyridylmethyl, oxodihydrooxazolopyridyl, thiazolopyridyl, oxodihydrothiazolopyridyl, imidazopyridyl, oxodihydroimidazopyridyl, chromanyl, chromanonyl, oxazolopyridyl, oxazolopyridylmethyl, isoquinolinyl, oxodihydroquinolinyl, tetrahydroquinolinyl, oxotetrahydroquinolinyl, benzodioxanyl, quinazolinyl, benzoazepinyl, tetrahydrobenzoazepinyl, benzodiazepinyl, tetrahydrobenzodiazepinyl, benzooxazepinyl, benzothiazepinyl;

and whereby aryl and heteroaryl residues as substituents of the cyclic imides can be substituted themselves by one to three of the same or different groups selected from halogen, cyano, $C_1$–$C_6$-alkyl, trifluoromethyl, $C_3$–$C_8$-cycloalkyl, benzyl, phenyl, hydroxy, $C_1$–$C_6$-hydroxyalkyl, $C_1$–$C_6$-alkoxy, $C_1$–$C_6$-alkoxy entirely or partially substituted by fluorine, benzyloxy, phenoxy, mercapto, $C_1$–$C_6$-alkylthio, phenylthio, carboxy, $C_2$–$C_7$-carboxyalkyl, $C_2$–$C_7$-carboxyalkenyl, $C_2$–$C_7$-alkoxycarbonyl, benzyloxycarbonyl, nitro, amino, $C_1$–$C_6$-aminoalkyl, mono-$C_1$–$C_6$-alkylamino, di-($C_1$–$C_6$-alkyl)amino and, for two adjacent residues, and methylenedioxy.

5. The compound according to claim 1 or 2,
wherein the substituents have the following meanings:

$R^1$ is selected from
hydrogen, fluorine, methyl, trifluoromethyl, ethylthio;

$R^2$ is hydrogen;

$R^3$ is hydrogen;

k is 0,

A is selected from
  ethylene or butylene, optionally substituted by hydroxy or one or two fluorine atoms, or
  OCH$_2$, SCH$_2$,
  ethenylene or 1,3-butadienylene;
D is selected from
  C$_4$–C$_6$-alkylene, optionally substituted by hydroxy;
  C$_4$–C$_6$-alkenylene;
  C$_4$–C$_6$-alkinylene; or
  C$_4$–C$_6$-alkylene, C$_4$–C$_6$-alkenylene or C$_4$–C$_6$-alkinylene, wherein one or two methylene units is isosterically replaced by O, NH or CO;
E is selected from
  monocyclic imides,
  anellated bicyclic imides,
  anellated tricyclic imides,
  anellated tetracyclic imides,
  bridged polycyclic imides, and
  spirocyclic imides,
  whereby these cyclic imides can be substituted by one to four of the same or different groups selected independently from each other from
  halogen, C$_1$–C$_4$-Alkyl, trifluoromethyl, hydroxy, hydroxymethyl, methoxy, ethoxy, tert-butoxy, trifluoromethoxy, benzyloxy, phenoxy, phenylthio, pyridylthio, phenylsulfonyl, sulfo, carboxy, C$_2$–C$_7$-carboxyalkyl, C$_2$–C$_7$-carboxyalkenyl, C$_2$–C$_7$-alkoxycarbonyl, benzyloxycarbonyl, nitro, amino, aminomethyl, dimethylamino, diethylamino, phenylamino, pyridylamino;
  benzyl, benzylidene, phenylethyl, naphthylmethyl, diphenylmethyl, diphenylmethylene, triphenylmethyl, phenyl, naphthyl;
  pyrrolidinyl, piperidinyl, morpholinyl, thiomorpholinyl, piperazinyl, hexahydroazepinyl, hexahydrodiazepinyl;
  furyl, furylmethyl, thienyl, thienylmethyl, thiazolyl, thiazolylmethyl, pyridyl, pyridylmethyl;
  benzofuryl, benzothienyl, indolyl, indolylmethyl, oxodihydro-indolyl, benzoimidazolyl, benzoimidazolylmethyl, oxodihydrobenzoimidazolyl, benzooxazolyl, oxodihydrobenzooxazolyl, benzothiazolyl, oxodihydrobenzothiazolyl, quinolinyl, quinolinylmethyl, oxodihydroquinolinyl, isoquinolinyl, oxodihydroisoquinolinyl,
  and whereby aryl and heteroaryl residues as substituents of the cyclic imides can be substituted themselves by one to three of the same or different groups selected from
  halogen, cyano, C$_1$–C$_6$-Alkyl, trifluoromethyl, C$_3$–C$_8$-cycloalkyl, benzyl, phenyl, hydroxy, C$_1$–C$_6$-hydroxyalkyl, C$_1$–C$_6$-alkoxy, C$_1$–C$_6$-alkoxy entirely or partially substituted by fluorine, benzyloxy, phenoxy, mercapto, C$_1$–C$_6$-alkylthio, phenylthio, carboxy, C$_2$–C$_7$-carboxyalkyl, C$_2$—C$_7$-carboxyalkenyl, C$_2$–C$_7$-alkoxycarbonyl, benzyloxycarbonyl, nitro, amino, C$_1$–C$_6$-aminoalkyl, mono-C$_1$–C$_6$-alkylamino, di-(C$_1$–C$_6$-alkyl)amino and, for two adjacent residues, methylenedioxy.

6. The compound according to claim 1, which is selected from the group consisting of:
N-[4-(2,5-dioxo-3,4-diphenyl-2,5-dihydro-pyrrol-1-yl)-butyl]-3-pyridin-3-yl-acrylamide,
N-[4-(2,6-dioxo-4-phenyl-piperidin-1-yl)-butyl]-3-pyridin-3-yl-acrylamide,
N-[4-(1,3-dioxo-4,5,6,7-tetraphenyl-1,3-dihydro-isoindol-2-yl)-butyl]-3-pyridin-3-yl-acrylamide,
N-[4-(3-benzyl-2,4,5-trioxo-imidazolidin-1-yl)-butyl]-3-pyri-din-3-yl-acrylamide,
N-[4-(1,3,10-trioxo-1,4,5,6,10,10a-hexahydro-acenaphtho[1,8a-c]pyrrol-2-yl)-butyl]-3-pyridin-3-yl-acrylamide,
N-[4-(2,5-dioxo-4,4-diphenyl-imidazolidin-1-yl)-butyl-3-pyri-din-3-yl-acrylamide,
N-[4-(2,5-dioxo-3-phenyl-2,5-dihydro-pyrrol-1-yl)-butyl]-3-pyridin-3-yl-acrylamide,
N-[3-(2,5-dioxo-3,4-diphenyl-2,5-dihydro-pyrrol-1-yl)-propyl]-3-pyridin-3-yl-acrylamide,
N-[4-(3-pyridin-3-yl-acroylamino)-butyl]-2,3:5,6-dibenzobicyc-lo[2.2.2]octan-7,8-dicarboximide,
N-[4-(5-benzyliden-2,4-dioxo-thiazolidin-3-yl)-butyl]-3-pyridin-3-yl-acrylamide,
N-[4-(4-benzyl-2,6-dioxo-piperazin-1-yl)-butyl]-3-pyridin-3-yl-acrylamide,
N-[6-(2,5-dioxo-3,4-diphenyl-2,5-dihydro-pyrrol-1-yl)-hexyl]-3-pyridin-3-yl-acrylamide,
N-[4-(2,5-dioxo-3,4-diphenyl-2,5-dihydro-pyrrol-1-yl)-butyl]-3-pyridin-3-yl-propionamide,
N-[4-(1,3-dioxo-1,3-dihydro-isoindol-2-yl)-butyl]-3-pyridin-3-yl-acrylamide,
N-[4-(1,3-dioxo-1H,3H-benzo[de]isoquinolin-2-yl)-butyl]-3-(1-oxidopyridin-3-yl)-acrylamide,
N-[6-(1,3-dioxo-1H,3H-benzo[de]isoquinolin-2-yl)-hexyl]-3-pyridin-3-yl-acrylamide,
N-[2-(1,3-dioxo-1H,3H-benzo[de]isoquinolin-2-yl)-ethyl]-3-pyridin-3-yl-acrylamide, and
N-[4-(1,3-dioxo-1H,3H-benzo[de]isoquinolin-2-yl)-butyl]-3-pyridin-3-yl-acrylamide.

7. Method for the production of compounds according to claim 1 or 2, wherein compounds of formula (I) are synthesized according to method (A) in such a manner that carboxylic acids of formula (II)

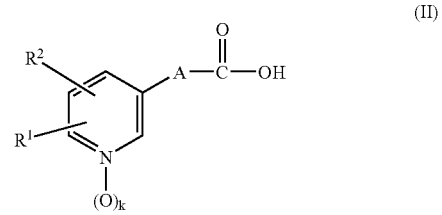

(II)

wherein R$^1$, R$^2$, A and k have the meanings according to claim 1 or 2 or their reactive derivatives, especially in form of their activated esters, anhydrides, acid halides (preferably acid chlorides) or simple lower alkyl esters, are reacted with compounds of formula (III)

(III)

wherein D, E, and R$^3$ have the meanings according to claim 1 or 2, in form of their free bases or acid addition salts, in a suitable solvent, or a mixture of one or more different solvents, at a temperature of −40° C. and 180° C., optionally in the presence of condensation agents and/or presence of an auxiliary base, or according to the variant pursuant to method (B), compounds of formula (I) are produced in that starting compounds of formula (IV)

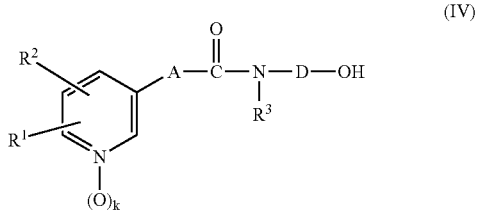

wherein $R^1$, $R^2$, $R^3$, A, D and k have the meaning according to claim 1 or 2 which were obtained by reacting carboxylic acids of formula (II) with amino alcohols of formula (VI),

wherein $R^3$ and D have the meaning according to claim 1 or 2 under conditions as they are described for method (A), are reacted with imides of the formula (V)

as starting compounds, wherein E is as defined in claim 1 or 2,
under the conditions of the Mitsunobu-reaction in which both starting compounds (IV) and (V), are combined by means of an organophosphor$^{III}$ compound and an aliphatic azo compound in a redox condensation, preferably in one or more aprotic solvents, especially tetrahydrofuran, and under inert gas with formal emergence of water whereby depending on the reactivity of the components, the reaction temperature varies in the range of –20° C. to 120° C.

8. A pharmaceutical composition comprising one or more of the compounds according to claim 1 or 2 as active ingredient(s) optionally in connection with a pharmaceutically acceptable carrier, next to toxicologically safe adjuvants, optionally in combination with other active ingredients.

9. A pharmaceutical composition comprising one or more of the compounds according to claim 1 or 2 as active ingredient, optionally in connection with a pharmaceutically acceptable carrier next to toxicologically safe adjuvants, optionally in combination with other active ingredients, wherein it is present in a solid, peroral administrable form as a tablet, capsule, coated tablet, optionally as sustained action and/or gastric fluid-resistant preparation or as a liquid, peroral administrable solution, suspension, effervescent tablet, in the form of tabs or sachets, optionally in sustained action form.

10. A pharmaceutical composition comprising one or more of the compounds according to claim 1 or 2 as active ingredient, optionally in connection with a pharmaceutically acceptable carrier next to toxicologically safe adjuvants, optionally in combination with other active ingredients, wherein it is present in the form of a suitable injection or infusion preparation together with suitable pharmaceutically acceptable carriers and adjuvants, optionally in sustained action form and/or as a parenteral depot medicinal form or implant or is used in the form of a concentrate, powder or lyophilisate and the parenteral dilution agent is optionally manufactured in the packaging separately therefrom, such that the mixing of the compounds contained therein with a common parenterally applicable dilution agent is possible immediately before use.

11. A pharmaceutical composition comprising one or more of the compounds according to claim 1 or 2 as active ingredient, optionally in connection with a pharmaceutically acceptable carrier next to toxicologically safe adjuvants, optionally in combination with other active ingredients, wherein it is present in the form of an inhalation therapeutic agentoptionally together with suitable pharmaceutically acceptable propellants, carriers and adjuvants.

12. A pharmaceutical composition comprising one or more of the compounds according to claim 1 or 2 as active ingredient, optionally in connection with a pharmaceutically acceptable carrier next to toxicologically safe adjuvants, optionally in combination with other active ingredients, wherein it is present in the form of a transdermal therapeutic system for systemic treatment.

13. A pharmaceutical composition comprising one or more of the compounds according to claim 1 or 2 as active ingredient, optionally in connection with a pharmaceutically acceptable carrier next to toxicologically safe adjuvants, optionally in combination with other active ingredients, wherein it is present in the form of a gastrointestinal therapeutic system (GITS) for systemic treatment.

14. A pharmaceutical composition comprising one or more of the compounds according to claim 1 or 2 as active ingredient, optionally in connection with a pharmaceutically acceptable carrier next to toxicologically safe adjuvants, optionally in combination with other active ingredients, wherein it is present in the form of a salve, suspension, emulsion, a balm or plaster or in the form of an externally applicable solution.

15. A pharmaceutical composition comprising one or more of the compounds according to claim 1 or 2 as active ingredient(s) optionally in connection with a pharmaceutically acceptable carrier, next to toxicology safe adjuvants, optionally in combination with other active ingredients, wherein it is present in the form of an inhalation therapeutic agent, optionally together with suitable pharmaceutically acceptable propellants, carriers and adjuvants for administration by means of a controlled dosage aerosol or in the form of a dry powder dosage formulation.

16. The pharmaceutical composition according to claim 8, wherein it is present in the form of a rectal, genital, or transurethral administrable emulsions, a solution, a liposomal solution, an implant, suppository or a capsule.

17. A pharmaceutical composition comprising one or more of the compounds according to claim 1 or 2 as active ingredient, optionally in connection with a pharmaceutically acceptable carrier next to toxicologically safe adjuvants, optionally in combination with other active ingredients, wherein it is present in the form of a composition capable of being applied nasally, otologically or ophthalmologically.

18. A pharmaceutical composition comprising one or more of the compounds according to claim 1 or 2 as active ingredient, optionally in connection with a pharmaceutically acceptable carrier next to toxicologically safe adjuvants, optionally in combination with other active ingredients, wherein it is present in the form of a buccally applicable form.

19. A pharmaceutical composition comprising one or more of the compounds according to claim 1 or 2 as active ingredient, optionally in connection with a pharmaceutically acceptable carrier next to toxicologically safe adjuvants, optionally in combination with other active ingredients, wherein a dosage unit for administration contains 0.001 to 1000, 2000, 3000, 4000 or 5000 mg single dose active ingredient according to claim 1 or 2.

20. A pharmaceutical composition comprising one or more of the compounds according to claim 1 or 2 as active ingredient(s) optionally in connection with a pharmaceutically acceptable carrier, next to toxicology safe adjuvants, optionally in combination with other active ingredients, wherein it is present in the form of an inhalation therapeutic agent, optionally together with suitable pharmaceutically acceptable propellants, carriers and adjuvants, wherein the pharmaceutically acceptable carrier and/or diluent is a propellant aerosol.

21. The pharmaceutical composition according to claim 11, wherein the propellant aerosol is tetrafluoroethane and/or heptafluoropropane and/or propane, butane, or dimethyl ether or mixtures thereof.

22. The pharmaceutical composition according to claim 11, wherein the propellant aerosol contains surface active adjuvants.

23. A pharmaceutical composition comprising one or more of the compounds according to claim 1 or 2 as active ingredient(s) optionally in connection with a pharmaceutically acceptable carrier, next to toxicology safe adjuvants, optionally in combination with other active ingredients, wherein it is present in the form of an inhalation therapeutic agent, optionally together with suitable pharmaceutically acceptable propellants, carriers and adjuvants, wherein it contains glucose and/or lactose as a dry powder dosage formulation.

24. A pharmaceutical composition comprising one or more of the compounds according to claim 1 or 2 as cytostatic agent or immunosuppressive agent, in combination with a further cytostatic agent or immunosuppressive agent which is not a compound according to claim 1 or 2, wherein it is present in combination with a further cytostatic agent or immunosuppressive agent, optionally in the form of separate dosage units in the pharmaceutical package.

* * * * *